US012241083B2

(12) United States Patent
Meyer et al.

(10) Patent No.: US 12,241,083 B2
(45) Date of Patent: *Mar. 4, 2025

(54) MACS-BASED PURIFICATION OF STEM CELL-DERIVED RETINAL PIGMENT EPITHELIUM

(71) Applicant: FUJIFILM Cellular Dynamics, Inc., Madison, WI (US)

(72) Inventors: Nathan Meyer, Madison, WI (US); Lucas Chase, Madison, WI (US); Casey Stankewicz, Madison, WI (US)

(73) Assignee: FUJIFILM Cellular Dynamics, Inc., Madison, WI (US)

( * ) Notice: Subject to any disclaimer, the term of this patent is extended or adjusted under 35 U.S.C. 154(b) by 702 days.

This patent is subject to a terminal disclaimer.

(21) Appl. No.: 17/493,533

(22) Filed: Oct. 4, 2021

(65) Prior Publication Data

US 2022/0033770 A1 Feb. 3, 2022

Related U.S. Application Data

(63) Continuation of application No. 15/258,744, filed on Sep. 7, 2016, now Pat. No. 11,162,070.

(60) Provisional application No. 62/215,272, filed on Sep. 8, 2015.

(51) Int. Cl.
*C12N 5/00* (2006.01)
*C12N 5/079* (2010.01)

(52) U.S. Cl.
CPC ......... *C12N 5/0081* (2013.01); *C12N 5/0621* (2013.01); *C12N 2506/03* (2013.01)

(58) Field of Classification Search
CPC .................................................. C12N 5/0081
See application file for complete search history.

(56) References Cited

U.S. PATENT DOCUMENTS

| | | | |
|---|---|---|---|
| 6,482,926 B1 | 11/2002 | Thomas et al. | |
| 7,259,011 B2 | 8/2007 | Lucas et al. | |
| 8,323,966 B2 | 12/2012 | Lebkowski et al. | |
| 9,040,039 B2 | 5/2015 | Klimanskaya et al. | |
| 9,040,770 B2 | 5/2015 | Klimanskaya et al. | |
| 2008/0299095 A1 | 12/2008 | Humphries et al. | |
| 2010/0105137 A1 | 4/2010 | Takahashi et al. | |
| 2013/0149284 A1 | 6/2013 | Malcuit et al. | |
| 2013/0196369 A1 | 8/2013 | Hikita et al. | |
| 2013/0224156 A1 | 8/2013 | Takahashi et al. | |
| 2013/0280809 A1 | 10/2013 | Efe et al. | |
| 2014/0220681 A1 | 8/2014 | Valamehr et al. | |
| 2015/0086512 A1 | 3/2015 | Malciut et al. | |
| 2015/0159134 A1 | 6/2015 | Choudhary et al. | |
| 2015/0175964 A1 | 6/2015 | Clegg et al. | |
| 2016/0264936 A1 | 9/2016 | Nakano et al. | |
| 2017/0067017 A1 | 3/2017 | Bharti et al. | |
| 2017/0107492 A1 | 4/2017 | Yu et al. | |
| 2018/0258388 A1 | 9/2018 | Ando et al. | |
| 2019/0169569 A1 | 6/2019 | Bharti et al. | |

FOREIGN PATENT DOCUMENTS

| | | |
|---|---|---|
| JP | 2014-168482 | 9/2014 |
| WO | WO 2009-051671 | 4/2009 |
| WO | WO 2011-028524 | 3/2011 |
| WO | WO 2011-063005 | 5/2011 |
| WO | WO 2012-109208 | 8/2012 |
| WO | WO 2013-039792 | 3/2013 |
| WO | WO 2013-114360 | 8/2013 |
| WO | WO 2014-121077 | 8/2014 |
| WO | WO 2014-153069 | 9/2014 |
| WO | WO 2014-188436 | 11/2014 |
| WO | WO 2015-054526 | 4/2015 |
| WO | WO 2015-087231 | 6/2015 |

OTHER PUBLICATIONS

"What is the difference between positive and negative cell separation?" Blog located at https://www.akadeum.com/blog/what-is-the-difference-beween-positive-and-negative-cell-separation/, Mar. 2020.
Amendola et al., "Coordinate dual-gene transgenesis by lentiviral vectors carrying synthetic bidirectional promoters," *Nature Biotechnology*, 23(1):108-116, 2005.
Batta et al., "Direct Reprogramming of Murine Fibroblasts to Hematopoietic Progenitor Cells," *Cell. Rep.*, 9(5):1871-1884, 2014.
Bharti et al., "The new paradigm: retinal pigment epithelium cells generated from embryonic or induced pluripotent stem cells," *Pigment Cell Melanoma Res.*, 24(1):21-34, 2011.
Bharti et al., U.S. Appl. No. 61/759,988, entitled "Method for generating retinal pigment epithelium (RPE) cells from induced pluripotent stem cells (IPSCs)," filed Feb. 1, 2013.
Brandl et al., "In-Depth characterisation of retinal pigment epithelium (RPE) cells derived from human induced pluripotent stem cells (hiPSC)," *Neuromol Med.*, 16:551-564, 2014.
Buchholz et al., "Derivation of functional retinal pigmented epithelium from induced pluripotent stem cells," *Stem Cells*, 27:2427-2434, 2009.
Byrne et al., "Producing primate embryonic stem cells by somatic cell nuclear transfer," *Nature*, 450(7169):497-502, 2007.
Cd59, Cell Atlas, located at https://www.proteinatlas.org/ENSG00000085063-CD59/cell, The Human Protein Atlas, downloaded Jul. 23, 2020.
Clontech, "Tet-off® advanced inducible gene expression system user manual," pp. 1-27, 2007.
Dodge et al., "Diverse chemical scaffolds support direct inhibition of the membrane-bound O-acyltransferase porcupine," *The Journal of Biological Chemistry*, 287(27):23246-23254, 2012.
Doulatov et al., "Induction of multipotential hematopoietic progenitors from human pluripotent stem cells via respecification of lineage-restricted precursors," *Cell Stem Cell*, 13(4):459-470, 2013.
Ebina et al., "Transcription factor-mediated reprogramming toward hematopoietic stem cells," *EMBO Journal*, 34(6):694-709, 2015.
Elcheva et al., "Direct induction of haematoendothelial programs in human pluripotent stem cells by transcriptional regulators," *Nat Commun*, 5:4372, 2014.

(Continued)

*Primary Examiner* — Valarie E Bertoglio
(74) *Attorney, Agent, or Firm* — Parker Highlander PLLC

(57) ABSTRACT

Provided herein are methods of enriching a retinal pigment epithelium (RPE) cell population derived from stem cells. Such a method may comprise removing contaminating cells through the depletion of CD24 positive cells, CD56 positive cells, and/or CD90 positive cells from a starting population of RPE cells.

19 Claims, 22 Drawing Sheets

(56) References Cited

OTHER PUBLICATIONS

Extended European Search Report issued in European Application No. 21204608.0, mailed Apr. 14, 2022.
Gonzalez et al., "Generation of mouse-induced pluripotent stem cells by transient expression of a single nonviral polycistronic vector," PNAS, 106(22):8918-8922, 2009.
Hirami et al., "Generation of retinal cells from mouse and human induced pluripotent stem cells," Neurosci. Lett., 458(3):126-131, 2009.
Kitajima et al., "In vitro generation of HSC-like cells from murine ESCs/iPSCs by enforced expression of LIM-homeobox transcription factor Lhx2," Blood, 117(14):3748-3758, 2011.
Klimanskaya et al., "Derivation and comparative assessment of retinal pigment epithelium from human embryonic stem cells using transcriptomics," Cloning and Stem Cells, 6(3):217-245, 2004.
Kyba et al., "HoxB4 confers definitive lymphoid-myeloid engraftment potential on embryonic stem cell and yolk sac hematopoietic progenitors," Cell, 109(1):29-37, 2002.
Lakowski et al., "Effective transplantation of photoreceptor precursor cells selected via cell surface antigen expression," Stem Cells, 29(9):1391-1404, 2011.
Mandai et al., "Use of lectins to enrich mouse ES-derived retinal progenitor cells for the purpose of transplantation therapy," Cell Transplantation, 19(1):9-19, 2010.
Maruotti et al., "," Proceedings of the National Academy of Sciences, 112(35):10950-10955, 2015.
McIntosh et al., "Nonirradiated NOD,B6.SCID Il2rγ-/- Kit(W41/W41) (NBSGW) mice support multilineage engraftment of human hematopoietic cells," Stem Cell Reports, 4(2):171-180, 2015.
Minskaia and Ryan, "Protein coexpression using FMDV 2A: effect of "linker" residues," Biomed Research International, 2013. Article ID 291790 pp. 1-12, 2013.
Office Action issued in Australian Application No. 2016318774, mailed Aug. 24, 2021.
Office Action issued in Australian Application No. 2016318774, mailed Mar. 15, 2022.
Office Action issued in Canadian Application No. 2,997,763, mailed Oct. 27, 2022.
Office Action issued in Chinese Application No. 201680060869.2, mailed Jan. 28, 2021, and English translation thereof.
Office Action issued in Chinese Application No. 201680060869.2, mailed Aug. 30, 2021, and English translation thereof.
Office Action issued in European Application No. 16775018.1, mailed Mar. 22, 2019.
Office Action issued in European Application No. 16775018.1, mailed Apr. 22, 2020.
Office Action issued in Japanese Application No. 2018-531311, mailed Aug. 4, 2020.
Office Action issued in Japanese Application No. 2021-133999, mailed Aug. 23, 2022.
Office Action issued in U.S. Appl. No. 15/258,744, mailed Apr. 4, 2019.
Office Action issued in U.S. Appl. No. 15/258,744, mailed Aug. 30, 2018.
Office Action issued in U.S. Appl. No. 15/258,744, mailed Feb. 1, 2021.
Office Action issued in U.S. Appl. No. 15/258,744, mailed Feb. 28, 2020.
Office Action issued in U.S. Appl. No. 15/258,744, mailed Jun. 30, 2020.
Office Action issued in U.S. Appl. No. 15/258,744, mailed Mar. 12, 2018.
PCT International Search Report and Written Opinion issued in International Application No. PCT/US2016/050543, mailed Dec. 5, 2016.
PCT International Search Report and Written Opinion issued in International Application No. PCT/US2016/057893, mailed Dec. 6, 2016.
PCT International Search Report and Written Opinion issued in International Application No. PCT/US2016/050554, mailed Nov. 28, 2016.
Pereira et al., "Induction of a Hemogenic Program in Mouse Fibroblasts," Cell Stem Cell, 13(2):205-218, 2013.
Ramos-Mejia et al., "HOXA9 promotes hematopoietic commitment of human embryonic stem cells," Blood, 124(20):3065-3075, 2014.
Riddell et al., "Reprogramming committed murine blood cells to induced hematopoietic stem cells with defined factors," Cell, 157(3):549-564, 2014.
Rodin et al., "Clonal culturing of human embryonic stem cells on laminin-521/E-cadherin matrix in defined and xeno-free environment," Nature Communications, 5:3195, 2014.
Rowland et al., "Differentiation of human pluripotent stem cells to retinal pigmented epithelium in defined conditions using purified extracellular matrix proteins," Journal of Tissue Engineering and Regenerative Medicine, 7:642-653, 2013.
Sandler et al., "Reprogramming human endothelial cells to haematopoietic cells requires vascular induction," Nature, 511(7509):312-318, 2014.
SBI, "pCDH cDNA cloning and expression lentivectors user manual" pp. 1-20, 2013.
Schwartz et al., "Embryonic stem cell trials for macular degeneration: a preliminary report," The Lancet, 379:713-720, 2012.
Sonoda et al., "A protocol for the culture and differentiation of highly polarized human retinal pigment epithelial cells" Nature Protocols, 4(5):662-673, 2009.
Sundberg, "CD marker expression profiles of human embryonic stem cells and their neural derivatives, determined using flow-cytometric analysis, reveal a novel CD marker for exclusion of pluripotent stem cells," Stem Cell Research, 2:113-124, 2009.
Suzuki et al., "Generation of Engraftable Hematopoietic Stem Cells From Induced Pluripotent Stem Cells by Way of Teratoma Formation," Mol Ther., 21(7):1424-1431, 2013.
Takeda, et al., "NUP98-HOXA9 induces long-term proliferation and blocks differentiation of primary human CD34+ hematopoietic cells." Cancer research 66.13 (2006): 6628-6637.
Thomson et al., "Human embryonic stem cell and embryonic germ cell lines," Trends in Biotechnology 18(2):53-57, 2000.
Vacca et al., "CD34+ hematopoietic precursors are present in human decidua and differentiate into natural killer cells upon interaction with stromal cells," PNAS, 108(6):2402-2407, 2011.
Van der Jeught et al., "The combination of inhibitors of FGF/MEK/Erk and GSK3β signaling increases the number of OCT3/4-and NANOG-positive cells in the human inner cell mass, but does not improve stem cell derivation," Stem Cells and Development, 22(2):296-306, 2013.
Vo et al., "De novo generation of HSCs from somatic and pluripotent stem cell sources," Blood, 125(17):2641-2648, 2015.
Vugler et al., "Elucidating the phenomenon of HESC-derived RPE: anatomy of cell genesis, expansion and retinal transplantation," Experimental Neurology, 214:347-361, 2008.
Young et al., "Human pluripotent and progenitor cells display cell surface cluster differentiation markers CD10, CD13, CD56 and MHC class-I," Proceedings of the Society of Experimental Biology and Medicine, 221(1):63-71, 1999.

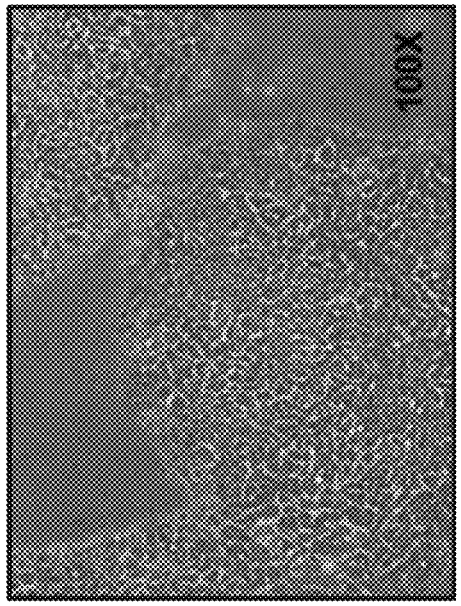
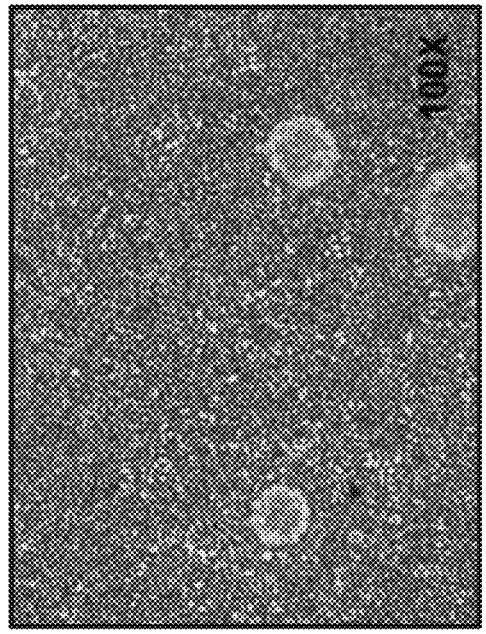
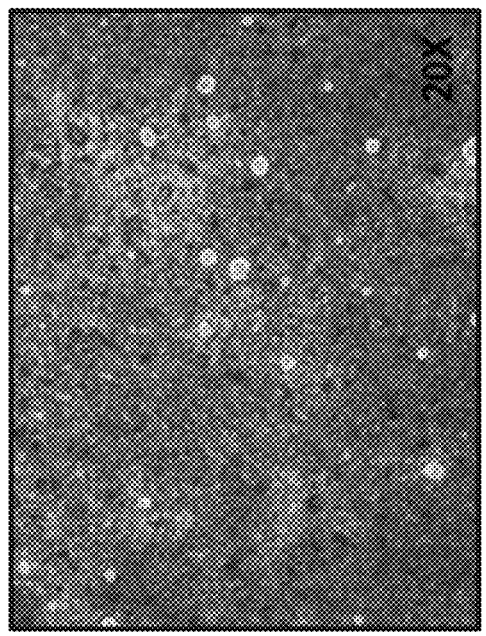
FIG. 1A
FIG. 1B

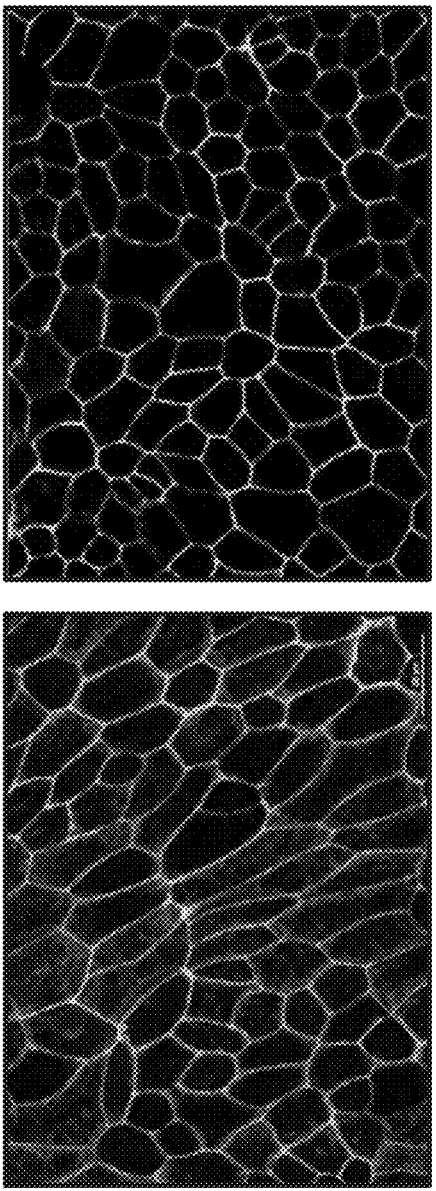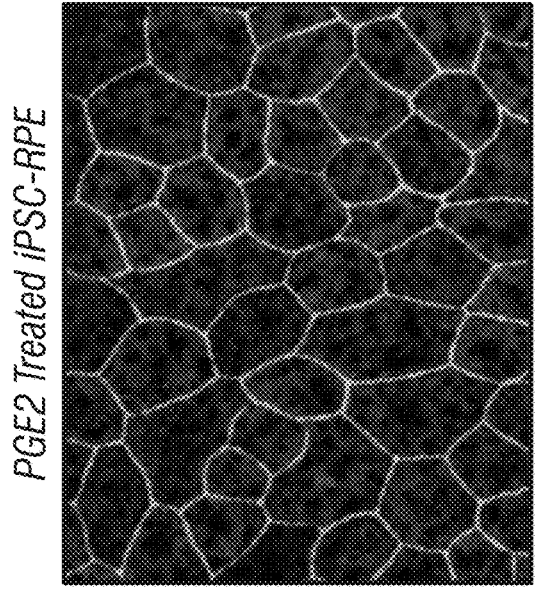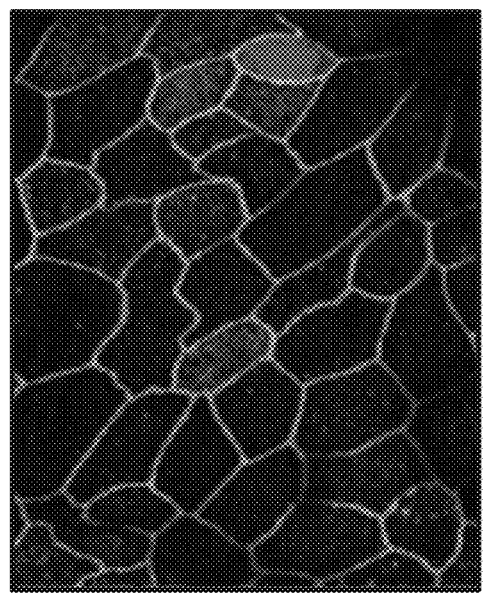

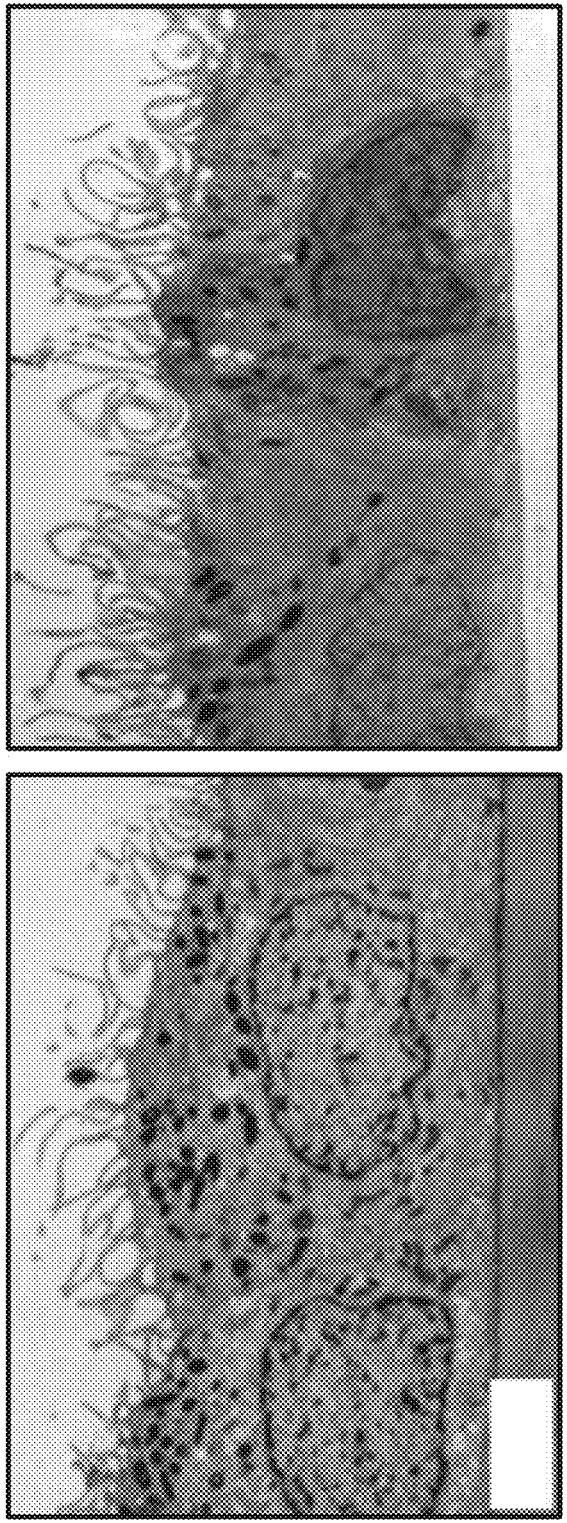
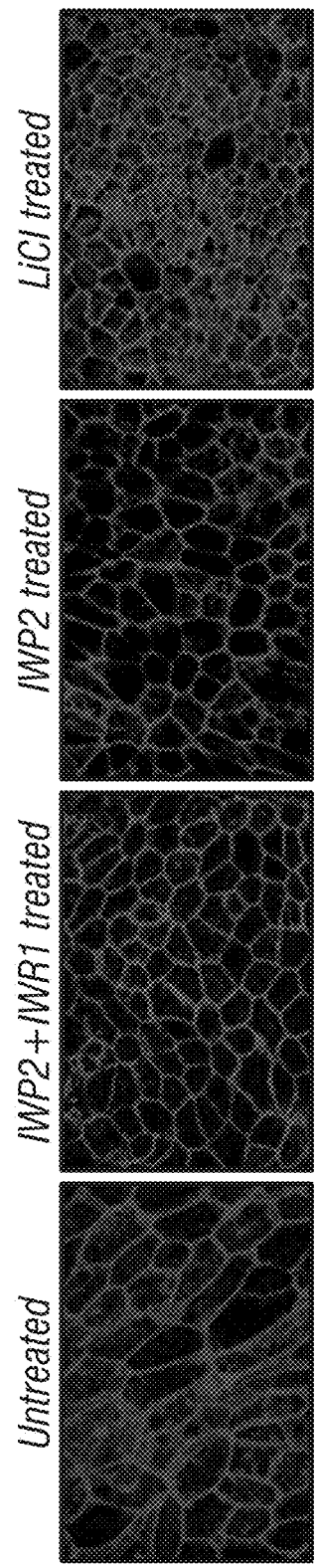
Transmission Electron Micrographs
FIG. 4D
BETA CATENIN
FIG. 5A

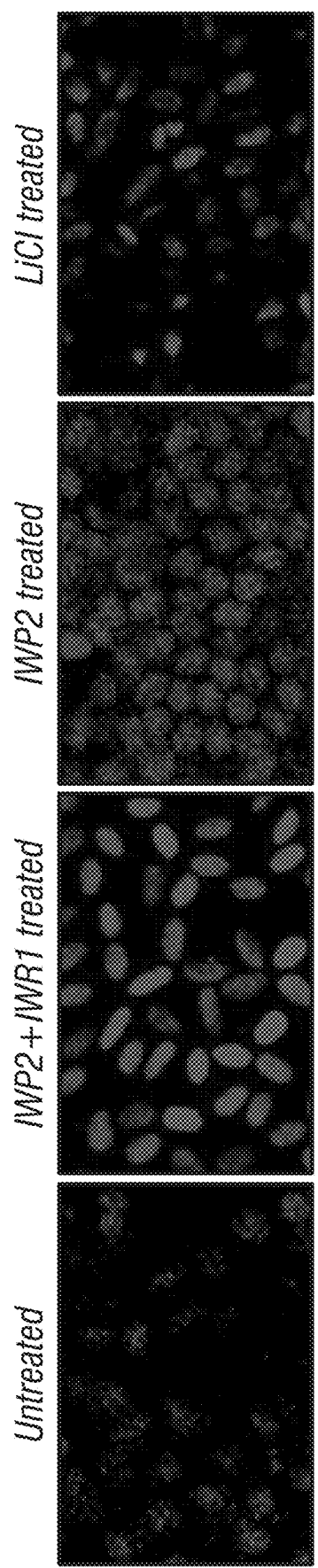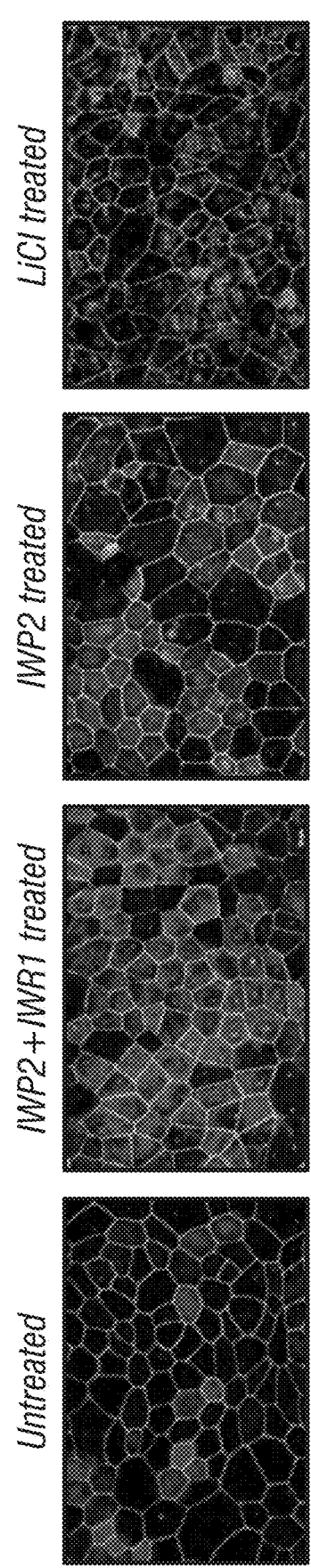
FIG. 5B  
FIG. 5C

TEM

MACS-BASED PURIFICATION OF STEM CELL-DERIVED RETINAL PIGMENT EPITHELIUM

The present application is a continuation of U.S. application Ser. No. 15/258,744, filed Sep. 7, 2016, which claims the priority benefit of U.S. provisional application No. 62/215,272, filed Sep. 8, 2015, the entire contents of each of which are incorporated herein by reference.

BACKGROUND OF THE INVENTION

1. Field of the Invention

The present invention relates generally to the field of stem cell biology. More particularly, it concerns methods of enriching stem cell-derived retinal pigment epithelial cell populations.

2. Description of Related Art

The retina is a light-sensitive layer of tissue that lines the inner surface of the eye. Photoreceptor cells, either rods or cones, in the retina are directly sensitive to light and transform chemical light signals into electrical events that trigger nerve impulses. The retinal pigment epithelium (RPE) is a layer of pigmented cells that forms the blood-retinal barrier. The RPE cells play important roles in the maintenance of visual function and the transport of ions, water, and metabolic end products from the subretinal space to the blood (Strauss et al., 2005). Further, RPE cells establish the immune privilege of the eye by secreting immunosuppressive factors. A disorder or injury to the RPE cells can result in degeneration of the retina, loss of visual function, and blindness. Several disorders of the retina, including acute and age-related macular degeneration and Best disease, involve degeneration of the RPE; therefore, cell replacement therapy is a possible therapeutic option for preservation of vision (Buchholz et al., 2009).

In general, stem cells are undifferentiated cells which can give rise to a succession of mature functional cells. For example, a hematopoietic stem cell may give rise to any of the different types of terminally differentiated blood cells. Embryonic stem (ES) cells are derived from the embryo and are pluripotent, thus possessing the capability of developing into any organ or tissue type, including RPE cells.

The production of induced pluripotent stem cells (iPSCs) from adult somatic mouse cells in 2006 provided an important breakthrough for stem cell research, drug development, models of disease, and cellular therapeutics (Takahashi et al., 2006). Human iPSCs can be differentiated to specialized cell types and have the potential for patient-specific, immune-matched cells for regenerative medicine (Yu et al., 2007).

iPSCs have been shown to give rise to ocular cells, including RPE cells (Hirami et al., 2009). However, the use of iPSC-derived RPE cells for therapeutics, screening assays, models of retinal disease, and RPE biology research requires the removal of contaminating cells from the differentiated RPE cell population and/or enrichment of the populations of interest.

SUMMARY OF THE INVENTION

The present embodiments overcome a major deficiency in the art by providing methods for obtaining a retinal pigment epithelial (RPE) cell-enriched population from a starting RPE cell population by the removal of CD24 positive cells, CD56 positive cells, and/or CD90 positive cells. In certain embodiments, the starting RPE cells population may be obtained from pluripotent stem cells such as, for example, embryonic stem cells or induced pluripotent stem cells.

In one embodiment, methods are provided for providing an enriched population of retinal pigment epithelial (RPE) cells comprising (a) obtaining a starting cell population comprising RPE cells and (b) enriching the cell population for RPE cells by removing therefrom cells that are positive for CD24, cells that are positive for CD56 and/or cells that are positive for CD90, thereby providing a RPE-enriched cell population that is enriched for RPE cells as compared to the starting cell population. In some aspects, the starting cell population is not genetically engineered or genetically modified. In some aspects, enriching the cell population does not comprise genetically engineering the cells. Thus, in certain aspects, the RPE-enriched cell population is not genetically engineered or genetically modified.

In some aspects, the methods may further comprise determining a level of enrichment of the RPE cells in the RPE-enriched population. In certain aspects, the level of enrichment is determined through the use of a retinal epithelial-specific marker. For example, the retinal epithelial-specific marker can be BEST1, CRALBP, TYRP1, PMEL17, or MITF. In a specific aspect, the RPE-enriched cell population is enriched for RPE cells as compared to the starting cell population as determined by BEST1 sorting.

In certain aspects, the RPE-enriched population is at least 95%, 96%, 97%, 98%, or 99% RPE cells. In other aspects, the RPE-enriched population is essentially pure RPE cells.

In certain aspects of the embodiments, the starting cell population is prepared from pluripotent stem cells. In further aspects, the pluripotent stem cells are induced pluripotent stem cells. For example, the RPE cells can be human RPE cells.

In certain aspects, the cells that are positive for CD24, cells that are positive for CD56 and/or cells that are positive for CD90 are removed. For example, the cells that are positive for CD24, cells that are positive for CD56 and/or cells that are positive for CD90 can be removed by magnetic bead-based sorting or fluorescence-based sorting. In certain aspects, the cells that are positive for CD24, cells that are positive for CD56 and/or cells that are positive for CD90 are removed using an antibody or an aptamer that recognizes CD24, CD56 and/or CD90.

In certain aspects, a cell population is enriched for RPE cells by removing therefrom cells that are positive for CD24. In other aspects, a cell population is enriched for RPE cells by removing therefrom cells that are positive for CD56. In yet another aspect, a cell population is enriched for RPE cells by removing therefrom cells that are positive for CD90. In a further aspect, a cell population is enriched for RPE cells by removing therefrom cells that are positive for CD90, cells that are positive of CD56 and cells that are positive for CD24.

The cell population provided herein may be essentially free of contaminating non-RPE cells such as fibroblasts or undifferentiated pluripotent stem cells. In a further aspect, the RPE cells are mouse or human RPE cells. In a particular aspect, the RPE cells may be cryopreserved RPE cells.

The RPE cells produced by the methods herein may be used in any methods and applications currently known in the art for RPE cells. For example, a method of assessing a compound may be provided, comprising assaying a pharmacological or toxicological property of the compound on the RPE cell. There may also be provided a method of assessing a compound for an effect on a RPE cell, comprising: a) contacting the RPE cells provided herein with the compound; and b) assaying an effect of the compound on the RPE cells.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-1D: A) Image of pre-confluent iPSCs. B) Example image for day 25 of RPE differentiation. C) Example image for day 40 of RPE differentiation. D) Example images at day 60 after a day 40 replate with culture in RPE-MM at 100× brightfield.

FIGS. 4A-4D: A) Beta catenin and F-Actin staining of iPSC-RPE untreated cells and iPSC-RPE cells treated with PGE2. Beta catenin staining is seen in the cytoplasm of the untreated cells and at the membrane in treated cells. B) pERM (Ezrin) and ZO1 staining of iPSC-RPE untreated cells and iPSC-RPE cells treated with PGE2. ERM staining is low in the cytoplasm of the untreated cells and high in the cytoplasm of the treated cells while ZO1 staining is seen at the tight junctions in the plasma membrane of both untreated and treated cells. C) RPE65 and ZO1 staining of iPSC-RPE untreated cells and iPSC-RPE cells treated with PGE2. RPE65 staining is low in the cytoplasm of the untreated cells and high in the cytoplasm of the treated cells. D) Transmission electron micrographs of iPSC-RPE untreated cells and iPSC-RPE cells treated with PGE2. Cells treated with PGE2 have more extensive apical processes.

FIGS. 5A-5D: A) Beta catenin staining of cells treated with IWP2+endo-IWR1, IWP2, or LiCl. Cells treated with IWP2 or IWP2+endo-IWR1 have beta catenin on cell membrane. Cell treated with LiCl have beta catenin in the nucleus and untreated cells have beta catenin in the cytoplasm. B) p27 staining of cells treated with IWP2+endo-IWR1, IWP2, or LiCl. Cells treated with IWP2 or IWP2+endo-IWR1 have higher p27 expression in the nucleus, suggesting that cells have exited cell cycle. Cells treated with LiCl or untreated cells have weak p27 expression in the nucleus. C) RPE65 and ZO1 tight junctions of cells treated with IWP2+IWR1, IWP2, or LiCl. RPE65 is high in the cytoplasm of the IWP2+IWR1 treated cells and IWP2 cells, low in the untreated cells and no staining is seen in the LiCl treated cells. D) Electron microscopy images of functional tight junctions of cells treated with IWP2+IWR1, IWP2, or LiCl.

DESCRIPTION OF ILLUSTRATIVE EMBODIMENTS

Figure 1C:
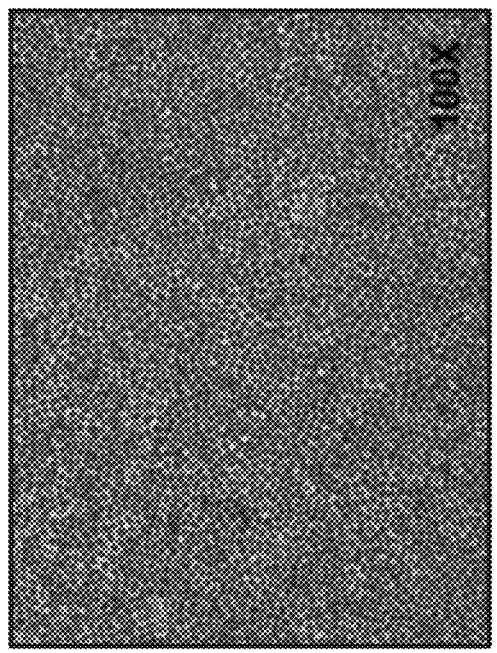

The present disclosure overcomes several major problems with current technologies by providing methods for enriching a stem cell-derived retinal pigment epithelial (RPE) cell population. RPE cells can be derived from pluripotent stem cells such as ES cells and iPS cells; however, even within a stem cell-derived RPE population using existing techniques, a certain amount of contaminating cells (e.g., undifferentiated stem cells) is found to be present. The present invention provides a method of separating and removing contaminating cells from a starting population of RPE cells. The cells that contaminate the RPE cell population have specific cell surface antigens which can be used for depleting contaminating non-RPE cells from the population such as CD24, CD56, and/or CD90. Therefore, removal of the cells positive for one or more of these specific cell surface markers can yield a RPE-enriched cell population that has a greater percentage of RPE cells than the starting population. Certain methodologies, such as Magnetic Activated Cell Sorting (MACS®), Fluorescent Activated Cell Sorting (FACS), or single cell sorting, and the like, are known in the art to separate various cell populations depending on their surface antigens. In preferred embodiments, the present disclosure comprises a method to use these sorting methodologies, preferably MACS, to deplete CD24, CD56, and/or CD90 positive cells from a starting RPE cell population to obtain a RPE-enriched cell population. Thus, the present methods may be more time and cost efficient and may enable manufacture of RPE-enriched cell populations for therapeutics from a renewable source, stem cells. Further embodiments and advantages of the present disclosure are described below.

I. Definitions

The term "purified" does not require absolute purity; rather, it is intended as a relative term. Thus, a purified population of cells is greater than about 90%, 91%, 92%, 93%, 94%, 95%, 96%, 97%, 98%, 99% or 100% pure, or, most preferably, essentially free other cell types.

As used herein, "essentially" or "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein in the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

The term "cell" is herein used to refer to a structural and functional unit of an organism that can replicate independently, is enclosed by a membrane, and contains biomolecules and genetic material. Cells used herein may be naturally-occurring cells or artificially modified cells (e.g., fusion cells, genetically modified cells, etc.).

The term "cell population" is used herein to refer to a group of cells, typically of a common type. The cell population can be derived from a common progenitor or may comprise more than one cell type. An "enriched" cell population refers to a cell population derived from a starting cell population (e.g., an unfractionated, heterogeneous cell population) that contains a greater percentage of a specific cell type than the percentage of that cell type in the starting population. The cell populations may be enriched for one or more cell types and depleted of one or more cell types.

The term "stem cell" refers herein to a cell that under suitable conditions is capable of differentiating into a diverse range of specialized cell types, while under other suitable conditions is capable of self-renewing and remaining in an essentially undifferentiated pluripotent state. The term "stem cell" also encompasses a pluripotent cell, multipotent cell, precursor cell and progenitor cell. Exemplary human stem cells can be obtained from hematopoietic or mesenchymal stem cells obtained from bone marrow tissue, embryonic stem cells obtained from embryonic tissue, or embryonic germ cells obtained from genital tissue of a fetus. Exemplary pluripotent stem cells can also produced from somatic cells by reprogramming them to a pluripotent state by the expression of certain transcription factors associated with pluripotency; these cells are called "induced pluripotent stem cells" or "iPSCs".

The term "pluripotent" refers to the property of a cell to differentiate into all other cell types in an organism, with the exception of extraembryonic, or placental, cells. Pluripotent stem cells are capable of differentiating to cell types of all three germ layers (e.g., ectodermal, mesodermal, and endodermal cell types) even after prolonged culture. A pluripotent stem cell is an embryonic stem cell derived from the inner cell mass of a blastocyst. In other embodiments, the pluripotent stem cell is an induced pluripotent stem cell derived by reprogramming somatic cells.

The term "differentiation" refers to the process by which an unspecialized cell becomes a more specialized type with changes in structural and/or functional properties. The mature cell typically has altered cellular structure and tissue-specific proteins. More specifically, in the context of the present methods indicates the process of a human stem cell acquiring the cell type of a retinal pigment epithelial (RPE) cell with features indicative that said RPE cell is a mature, terminally differentiated cell.

As used herein, "undifferentiated" refers to cells that display characteristic markers and morphological characteristics of undifferentiated cells that clearly distinguish them from terminally differentiated cells of embryo or adult origin.

"Embryoid bodies (EBs)" are aggregates of pluripotent stem cells that can undergo differentiation into cells of the endoderm, mesoderm, and ectoderm germ layers. The spheroid structures form when pluripotent stem cells aggregate and enable the non-adherent culture of EBs in suspension.

An "isolated" cell has been substantially separated or purified from others cells in an organism or culture. Isolated cells can be, for example, at least 99%, at least 98% pure, at least 95% pure or at least 90% pure.

An "embryo" refers to a cellular mass obtained by one or more divisions of a zygote or an activated oocyte with an artificially reprogrammed nucleus.

An "embryonic stem (ES) cell" is an undifferentiated pluripotent cell which is obtained from an embryo in an early stage, such as the inner cell mass at the blastocyst stage, or produced by artificial means (e.g. nuclear transfer) and can give rise to any differentiated cell type in an embryo or an adult, including germ cells (e.g. sperm and eggs).

"Induced pluripotent stem cells (iPSCs)" are cells generated by reprogramming a somatic cell by expressing or inducing expression of a combination of factors (herein referred to as reprogramming factors). iPSCs can be generated using fetal, postnatal, newborn, juvenile, or adult somatic cells. In certain embodiments, factors that can be used to reprogram somatic cells to pluripotent stem cells include, for example, Oct4 (sometimes referred to as Oct 3/4), Sox2, c-Myc, and Klf4, Nanog, and Lin28. In some embodiments, somatic cells are reprogrammed by expressing at least two reprogramming factors, at least three reprogramming factors, or four reprogramming factors to reprogram a somatic cell to a pluripotent stem cell.

An "allele" refers to one of two or more forms of a gene. Diploid organisms such as humans contain two copies of each chromosome, and thus carry one allele on each.

The term "homozygous" is defined as containing two of the same alleles at a particular locus. The term "heterozygous" refers to as containing two different alleles at a particular locus.

A "haplotype" refers to a combination of alleles at multiple loci along a single chromosome. A haplotype can be based upon a set of single-nucleotide polymorphisms (SNPs) on a single chromosome and/or the alleles in the major histocompatibility complex.

As used herein, the term "haplotype-matched" is defined as the cell (e.g. iPSC cell) and the subject being treated share one or more major histocompatibility locus haplotypes. The haplotype of the subject can be readily determined using assays well known in the art. The haplotype-matched iPSC cell can be autologous or allogeneic. The autologous cells which are grown in tissue culture and differentiated to RPE cells inherently are haplotype-matched to the subject.

"Substantially the same HLA type" indicates that the HLA type of donor matches with that of a patient to the extent that the transplanted cells, which have been obtained by inducing differentiation of iPSCs derived from the donor's somatic cells, can be engrafted when they are transplanted to the patient.

"Super donors" are referred to herein as individuals that are homozygous for certain MHC class I and II genes. These homozygous individuals can serve as super donors and their cells, including tissues and other materials comprising their cells, can be transplanted in individuals that are either homozygous or heterozygous for that haplotype. The super donor can be homozygous for the HLA-A, HLA-B, HLA-C, HLA-DR, HLA-DP or HLA-DQ locus/loci alleles, respectively.

"Feeder-free" or "feeder-independent" is used herein to refer to a culture supplemented with cytokines and growth factors (e.g., TGFβ, bFGF, LIF) as a replacement for the feeder cell layer. Thus, "feeder-free" or feeder-independent culture systems and media may be used to culture and maintain pluripotent cells in an undifferentiated and proliferative state. In some cases, feeder-free cultures utilize an animal-based matrix (e.g. MATRIGEL™) or are grown on a substrate such as fibronectin, collagen or vitronectin. These approaches allow human stem cells to remain in an essentially undifferentiated state without the need for mouse fibroblast "feeder layers."

"Feeder layers" are defined herein as a coating layer of cells such as on the bottom of a culture dish. The feeder cells can release nutrients into the culture medium and provide a surface to which other cells, such as pluripotent stem cells, can attach.

The term "defined" or "fully defined," when used in relation to a medium, an extracellular matrix, or a culture condition, refers to a medium, an extracellular matrix, or a culture condition in which the chemical composition and amounts of approximately all the components are known. For example, a defined medium does not contain undefined factors such as in fetal bovine serum, bovine serum albumin or human serum albumin. Generally, a defined medium comprises a basal media (e.g., Dulbecco's Modified Eagle's Medium (DMEM), F12, or Roswell Park Memorial Institute Medium (RPMI) 1640, containing amino acids, vitamins, inorganic salts, buffers, antioxidants and energy sources) which is supplemented with recombinant albumin, chemically defined lipids, and recombinant insulin. An exemplary fully defined medium is Essential 8™ medium.

The term "Xeno-Free (XF)" when used in relation to a medium, an extracellular matrix, or a culture condition, refers to a medium, an extracellular matrix, or a culture condition which is essentially free from heterogeneous animal-derived components. For culturing human cells, any proteins of a non-human animal, such as mouse, would be xeno components. In certain aspects, the Xeno-free matrix may be essentially free of any non-human animal-derived components, therefore excluding mouse feeder cells or MATRIGEL™. MATRIGEL™ is a solubilized basement membrane preparation extracted from the Engelbreth-Holm-Swarm (EHS) mouse sarcoma, a tumor rich in extracellular matrix proteins to include laminin (a major component), collagen IV, heparan sulfate proteoglycans, and entactin/nidogen.

"KNOCKOUT™ serum replacement," referred to herein as a serum-free formulation optimized to grow and maintain undifferentiated cells, such as stem cell, in culture.

"Pre-confluent" refers to a cell culture in which the proportion of the culture surface which is covered by cells is about 60-80%. Usually, pre-confluent refers to a culture in which about 70% of the culture surface is covered by cells.

The "retina" refers to a light-sensitive layer of tissue which lines the inner surface of the eye.

"Retinal pigment epithelium" refers to a monolayer of pigmented cells between the choroid, a layer filled with blood vessels, and the retina.

"Retinal lineage cells" herein refer to cells that can give rise or differentiate to RPE cells.

"Retinal Induction Medium (RIM)" refers herein to a growth media that comprises a WNT pathway inhibitor and a BMP pathway inhibitor and can result in the differentiation of PSCs to retinal lineage cells. The RIM also comprises a TGFβ pathway inhibitor.

The "Retinal Differentiation Medium (RDM)" is defined herein as a medium that comprises a WNT pathway inhibitor, a BMP pathway inhibitor and a MEK inhibitor and differentiates retinal cells. The RDM also comprises a TGFβ pathway inhibitor.

The "Retinal Medium (RM)" is defined as a growth medium for the culture of retinal cells comprising Activin A and Nicotinamide.

The "RPE-Maturation Medium (RPE-MM)" herein refers to a medium for the maturation of RPE cells comprising taurine and hydrocortisone. The RPE-MM also comprises triiodothyronine. The RPE-MM may also comprise PD0325901 or PGE2.

"Mature" RPE cells are referred to herein as RPE cells which have downregulated expression of immature RPE markers such as Pax6 and upregulated expression of mature RPE markers such as RPE65.

RPE cell "maturation" refers herein to the process by which RPE developmental pathways are modulated to generate mature RPE cells. For example, modulation of cilia function can result in RPE maturation.

A "therapeutically effective amount" used herein refers to the amount of a compound that, when administered to a subject for treatment of a disease or condition, is sufficient to effect such treatment.

"Inducer" is defined herein as a molecule that regulates gene expression such as activating genes within a cell. An inducer can bind to repressors or activators. Inducers functions by disabling repressors.

II. Pluripotent Stem Cells

A. Embryonic Stem Cells

ES cells are derived from the inner cell mass of blastocysts and have a high in vitro differentiating capability. ES cells can be isolated by removing the outer trophectoderm layer of a developing embryo, then culturing the inner mass cells on a feeder layer of non-growing cells. The replated cells can continue to proliferate and produce new colonies of ES cells which can be removed, dissociated, replated again and allowed to grow. This process of "subculturing" undifferentiated ES cells can be repeated a number of times to produce cell lines containing undifferentiated ES cells (U.S. Pat. Nos. 5,843,780; 6,200,806; 7,029,913). ES cells have the potential to proliferate while maintaining their pluripotency. For example, ES cells are useful in research on cells and on genes which control cell differentiation. The pluripotency of ES cells combined with genetic manipulation and selection can be used for gene analysis studies in vivo via the generation of transgenic, chimeric, and knockout mice.

Methods for producing mouse ES cells are well known. In one method, a preimplantation blastocyst from the 129 strain of mice is treated with mouse antiserum to remove the trophoectoderm, and the inner cell mass is cultured on a feeder cell layer of chemically inactivated mouse embryonic fibroblasts in medium containing fetal calf serum. Colonies of undifferentiated ES cells that develop are subcultured on mouse embryonic fibroblast feeder layers in the presence of fetal calf serum to produce populations of ES cells. In some methods, mouse ES cells can be grown in the absence of a feeder layer by adding the cytokine leukemia inhibitory factor (LIF) to serum-containing culture medium (Smith, 2000). In other methods, mouse ES cells can be grown in serum-free medium in the presence of bone morphogenetic protein and LIF (Ying et al., 2003).

Human ES cells can be produced or derived from a zygote or blastocyst-staged mammalian embryo produced by the fusion of a sperm and egg cell, nuclear transfer, pathogenesis, or the reprogramming of chromatin and subsequent incorporation of the reprogrammed chromatin into a plasma membrane to produce an embryonic cell by previously described methods (Thomson and Marshall, 1998; Reubinoff et al., 2000). In one method, human blastocysts are exposed to anti-human serum, and trophectoderm cells are lysed and removed from the inner cell mass which is cultured on a feeder layer of mouse embryonic fibroblasts. Further, clumps of cells derived from the inner cell mass are chemically or mechanically dissociated, replated, and colonies with undifferentiated morphology are selected by micropipette, dissociated, and replated (U.S. Pat. No. 6,833, 269). In some methods, human ES cells can be grown without serum by culturing the ES cells on a feeder layer of fibroblasts in the presence of basic fibroblast growth factor (Amit et al., 2000). In other methods, human ES cells can be grown without a feeder cell layer by culturing the cells on a protein matrix such as MATRIGEL™ or laminin in the presence of "conditioned" medium containing basic fibroblast growth factor (Xu et al., 2001).

ES cells can also be derived from other organisms including rhesus monkey and marmoset by previously described methods (Thomson, and Marshall, 1998; Thomson et al., 1995; Thomson and Odorico, 2000), as well as from established mouse and human cell lines. For example, established human ES cell lines include MAOI, MA09, ACT-4, HI, H7, H9, H13, H14 and ACT30. As a further example, mouse ES cell lines that have been established include the CGR8 cell line established from the inner cell mass of the mouse strain 129 embryos, and cultures of CGR8 cells can be grown in the presence of LIF without feeder layers.

ES stem cells can be detected by protein markers including transcription factor Oct4, alkaline phosphatase (AP), stage-specific embryonic antigen SSEA-1, stage-specific embryonic antigen SSEA-3, stage-specific embryonic antigen SSEA-4, transcription factor NANOG, tumor rejection antigen 1-60 (TRA-1-60), tumor rejection antigen 1-81 (TRA-1-81), SOX2, or REX1.

B. Induced Pluripotent Stem Cells

The induction of pluripotency was originally achieved in 2006 using mouse cells (Yamanaka et al. 2006) and in 2007 using human cells (Yu et al. 2007; Takahashi et al. 2007) by reprogramming of somatic cells via the introduction of transcription factors that are linked to pluripotency. Pluripotent stem cells can be maintained in an undifferentiated state and are capable of differentiating into almost any cell type. The use of iPSCs circumvents most of the ethical and practical problems associated with large-scale clinical use of ES cells, and patients with iPSC-derived autologous transplants may not require lifelong immunosuppressive treatments to prevent graft rejection.

With the exception of germ cells, any cell can be used as a starting point for iPSCs. For example, cell types could be keratinocytes, fibroblasts, hematopoietic cells, mesenchymal cells, liver cells, or stomach cells. T cells may also be used as a source of somatic cells for reprogramming (U.S. Pat. No. 8,741,648). There is no limitation on the degree of cell differentiation or the age of an animal from which cells are collected; even undifferentiated progenitor cells (including somatic stem cells) and finally differentiated mature cells can be used as sources of somatic cells in the methods disclosed herein. In one embodiment, the somatic cell is itself a RPE cells such as a human RPE cell. The RPE cell can be an adult or a fetal RPE cell. iPSCs can be grown under conditions that are known to differentiate human ES cells into specific cell types, and express human ES cell markers including: SSEA-1, SSEA-3, SSEA-4, TRA-1-60, and TRA-1-81.

Somatic cells can be reprogrammed to produce induced pluripotent stem cells (iPSCs) using methods known to one of skill in the art. One of skill in the art can readily produce induced pluripotent stem cells, see for example, Published U.S. Patent Application No. 20090246875, Published U.S. Patent Application No. 2010/0210014; Published U.S. Patent Application No. 20120276636; U.S. Pat. Nos. 8,058,065; 8,129,187; 8,278,620; PCT Publication NO. WO 2007/069666 A1, and U.S. Pat. No. 8,268,620, which are incorporated herein by reference. Generally, nuclear reprogramming factors are used to produce pluripotent stem cells from a somatic cell. In some embodiments, at least three, or at least four, of Klf4, c-Myc, Oct3/4, Sox2, Nanog, and Lin28 are utilized. In other embodiments, Oct3/4, Sox2, c-Myc and Klf4 are utilized.

The cells are treated with a nuclear reprogramming substance, which is generally one or more factor(s) capable of inducing an iPSC from a somatic cell or a nucleic acid that encodes these substances (including forms integrated in a vector). The nuclear reprogramming substances generally include at least Oct3/4, Klf4 and Sox2 or nucleic acids that encode these molecules. A functional inhibitor of p53, L-myc or a nucleic acid that encodes L-myc, and Lin28 or Lin28b or a nucleic acid that encodes Lin28 or Lin28b, can be utilized as additional nuclear reprogramming substances. Nanog can also be utilized for nuclear reprogramming. As disclosed in published U.S. Patent Application No. 20120196360, exemplary reprogramming factors for the production of iPSCs include (1) Oct3/4, Klf4, Sox2, L-Myc (Sox2 can be replaced with Sox1, Sox3, Sox15, Sox17 or Sox18; Klf4 is replaceable with Klf1, Klf2 or Klf5); (2) Oct3/4, Klf4, Sox2, L-Myc, TERT, SV40 Large T antigen (SV40LT); (3) Oct3/4, Klf4, Sox2, L-Myc, TERT, human papilloma virus (HPV)16 E6; (4) Oct3/4, Klf4, Sox2, L-Myc, TERT, HPV16 E7 (5) Oct3/4, Klf4, Sox2, L-Myc, TERT, HPV16 E6, HPV16 E7; (6) Oct3/4, Klf4, Sox2, L-Myc, TERT, Bmil; (7) Oct3/4, Klf4, Sox2, L-Myc, Lin28; (8) Oct3/4, Klf4, Sox2, L-Myc, Lin28, SV40LT; (9) Oct3/4, Klf4, Sox2, L-Myc, Lin28, TERT, SV40LT; (10) Oct3/4, Klf4, Sox2, L-Myc, SV40LT; (11) Oct3/4, Esrrb, Sox2, L-Myc (Esrrb is replaceable with Esrrg); (12) Oct3/4, Klf4, Sox2; (13) Oct3/4, Klf4, Sox2, TERT, SV40LT; (14) Oct3/4, Klf4, Sox2, TERT, HP VI 6 E6; (15) Oct3/4, Klf4, Sox2, TERT, HPV16 E7; (16) Oct3/4, Klf4, Sox2, TERT, HPV16 E6, HPV16 E7; (17) Oct3/4, Klf4, Sox2, TERT, Bmil; (18) Oct3/4, Klf4, Sox2, Lin28 (19) Oct3/4, Klf4, Sox2, Lin28, SV40LT; (20) Oct3/4, Klf4, Sox2, Lin28, TERT, SV40LT; (21) Oct3/4, Klf4, Sox2, SV40LT; or (22) Oct3/4, Esrrb, Sox2 (Esrrb is replaceable with Esrrg). In one non-limiting example, Oct3/4, Klf4, Sox2, and c-Myc are utilized. In other embodiments, Oct4, Nanog, and Sox2 are utilized, see for example, U.S. Pat. No. 7,682,828, which is incorporated herein by reference. These factors include, but are not limited to, Oct3/4, Klf4 and Sox2. In other examples, the factors include, but are not limited to Oct 3/4, Klf4 and Myc. In some non-limiting examples, Oct3/4, Klf4, c-Myc, and Sox2 are utilized. In other non-limiting examples, Oct3/4, Klf4, Sox2 and Sal 4 are utilized. Factors like Nanog, Lin28, Klf4, or c-Myc can increase reprogramming efficiency and can be expressed from several different expression vectors. For example, an integrating vector such as the EBV element-based system can be used (U.S. Pat. No. 8,546,140). In a further aspect, reprogramming proteins could be introduced directly into somatic cells by protein transduction. Reprogramming may further comprise contacting the cells with one or more signaling receptors including glycogen synthase kinase 3 (GSK-3) inhibitor, a mitogen-activated protein kinase kinase (MEK) inhibitor, a transforming growth factor beta (TGF-β) receptor inhibitor or signaling inhibitor, leukemia inhibitory factor (LIF), a p53 inhibitor, an NF-kappa B inhibitor, or a combination thereof. Those regulators may include small molecules, inhibitory nucleotides, expression cassettes, or protein factors. It is anticipated that virtually any iPS cells or cell lines may be used.

Mouse and human cDNA sequences of these nuclear reprogramming substances are available with reference to the NCBI accession numbers mentioned in WO 2007/069666, which is incorporated herein by reference. Methods for introducing one or more reprogramming substances, or nucleic acids encoding these reprogramming substances, are known in the art, and disclosed for example, in published U.S. Patent Application No. 2012/0196360 and U.S. Pat. No. 8,071,369, which both are incorporated herein by reference.

Once derived, iPSCs can be cultured in a medium sufficient to maintain pluripotency. The iPSCs may be used with various media and techniques developed to culture pluripotent stem cells, more specifically, embryonic stem cells, as described in U.S. Pat. No. 7,442,548 and U.S. Patent Pub. No. 2003/0211603. In the case of mouse cells, the culture is carried out with the addition of Leukemia Inhibitory Factor (LIF) as a differentiation suppression factor to an ordinary medium. In the case of human cells, it is desirable that basic fibroblast growth factor (bFGF) be added in place of LIF.

Other methods for the culture and maintenance of iPSCs, as would be known to one of skill in the art, may be used.

In certain embodiments, undefined conditions may be used; for example, pluripotent cells may be cultured on fibroblast feeder cells or a medium that has been exposed to fibroblast feeder cells in order to maintain the stem cells in an undifferentiated state. In some embodiments, the cell is cultured in the co-presence of mouse embryonic fibroblasts treated with radiation or an antibiotic to terminate the cell division, as feeder cells. Alternately, pluripotent cells may be cultured and maintained in an essentially undifferentiated state using a defined, feeder-independent culture system, such as a TESR™ medium (Ludwig et al., 2006a; Ludwig et al., 2006b) or E8™ medium (Chen et al., 2011).

In some embodiments, the iPSC can be modified to express exogenous nucleic acids, such as to include a tyrosinase enhancer operaby linked to a promoter and a nucleic acid sequence encoding a first marker. The tyrosinase gene is disclosed, for example, in GENBANK® Accession No. 22173, as available on Jan. 1, 2013. This sequence aligns to chromosome 7 of mouse strain C57BL/6 location 5286971-5291691 (invert orientation). A 4721 base pair sequence is sufficient for expression in RPE cells, see Murisier et al., Dev. Biol. 303: 838-847, 2007, which is incorporated herein by reference. This construct is expressed in retinal pigment epithelial cells. Other enhancers can be utilized. Other RPE-specific enhancers include D-MITF, DCT, TYRP1, RPE65, VMD2, MERTK, MYRIP, and RAB27A. Suitable promoters include, but are not limited to, any promoter expressed in retinal pigment epithelial cells including the tyrosinase promoter. The construct can also include other elements, such as a ribosome binding site for translational initiation (internal ribosomal binding sequences), and a transcription/translation terminator. Generally, it is advantageous to transfect cells with the construct. Suitable vectors for stable transfection include, but are not limited to retroviral vectors, lentiviral vectors and Sendai virus.

Plasmids have been designed with a number of goals in mind, such as achieving regulated high copy number and avoiding potential causes of plasmid instability in bacteria, and providing means for plasmid selection that are compatible with use in mammalian cells, including human cells. Particular attention has been paid to the dual requirements of plasmids for use in human cells. First, they are suitable for maintenance and fermentation in *E. coli*, so that large amounts of DNA can be produced and purified. Second, they are safe and suitable for use in human patients and animals. The first requirement calls for high copy number plasmids that can be selected for and stably maintained relatively easily during bacterial fermentation. The second requirement calls for attention to elements such as selectable markers and other coding sequences. In some embodiments plasmids that encode a marker are composed of: (1) a high copy number replication origin, (2) a selectable marker, such as, but not limited to, the neo gene for antibiotic selection with kanamycin, (3) transcription termination sequences, including the tyrosinase enhancer and (4) a multicloning site for incorporation of various nucleic acid cassettes; and (5) a nucleic acid sequence encoding a marker operably linked to the tyrosinase promoter. There are numerous plasmid vectors that are known in the art for inducing a nucleic acid encoding a protein. These include, but are not limited to, the vectors disclosed in U.S. Pat. Nos. 6,103,470; 7,598,364; 7,989,425; and 6,416,998, which are incorporated herein by reference.

A viral gene delivery system can be an RNA-based or DNA-based viral vector. An episomal gene delivery system can be a plasmid, an Epstein-Barr virus (EBV)-based episomal vector, a yeast-based vector, an adenovirus-based vector, a simian virus 40 (SV40)-based episomal vector, a bovine papilloma virus (BPV)-based vector, or a lentiviral vector.

Markers include, but are not limited to, fluorescence proteins (for example, green fluorescent protein or red fluorescent protein), enzymes (for example, horse radish peroxidase or alkaline phosphatase or firefly/renilla luciferase or nanoluc), or other proteins. A marker may be a protein (including secreted, cell surface, or internal proteins; either synthesized or taken up by the cell); a nucleic acid (such as an mRNA, or enzymatically active nucleic acid molecule) or a polysaccharide. Included are determinants of any such cell components that are detectable by antibody, lectin, probe or nucleic acid amplification reaction that are specific for the marker of the cell type of interest. The markers can also be identified by a biochemical or enzyme assay or biological response that depends on the function of the gene product. Nucleic acid sequences encoding these markers can be operably linked to the tyrosinase enhancer. In addition, other genes can be included, such as genes that may influence stem cell to RPE differentiation, or RPE function, or physiology, or pathology. Thus, in some embodiments, a nucleic acid is included that encodes one or more of MITF, PAX6, TFEC, OTX2, LHX2, VMD2, CFTR, RPE65, MFRP, CTRP5, CFH, C3, C2B, APOE, APOB, mTOR, FOXO, AMPK, SIRT1-6, HTRP1, ABCA4, TIMP3, VEGFA, CFI, TLR3, TLR4, APP, CD46, BACE1, ELOLV4, ADAM 10, CD55, CD59, and ARMS2.

1. MHC Haplotype Matching

Major Histocompatibility Complex is the main cause of immune-rejection of allogeneic organ transplants. There are three major class I MHC haplotypes (A, B, and C) and three major MHC class II haplotypes (DR, DP, and DQ). The HLA loci are highly polymorphic and are distributed over 4 Mb on chromosome 6. The ability to haplotype the HLA genes within the region is clinically important since this region is associated with autoimmune and infectious diseases and the compatibility of HLA haplotypes between donor and recipient can influence the clinical outcomes of transplantation. HLAs corresponding to MHC class I present peptides from inside the cell and HLAs corresponding to MHC class II present antigens from outside of the cell to T-lymphocytes. Incompatibility of MHC haplotypes between the graft and the host triggers an immune response against the graft and leads to its rejection. Thus, a patient can be treated with an immunosuppressant to prevent rejection. HLA-matched stem cell lines may overcome the risk of immune rejection.

Because of the importance of HLA in transplantation, the HLA loci are usually typed by serology and PCR for identifying favorable donor-recipient pairs. Serological detection of HLA class I and II antigens can be accomplished using a complement mediated lymphocytotoxicity test with purified T or B lymphocytes. This procedure is predominantly used for matching HLA-A and -B loci. Molecular-based tissue typing can often be more accurate than serologic testing. Low resolution molecular methods such as SSOP (sequence specific oligonucleotide probes) methods, in which PCR products are tested against a series of oligonucleotide probes, can be used to identify HLA antigens, and currently these methods are the most common methods used for Class II-HLA typing. High resolution techniques such as SSP (sequence specific primer) methods which utilize allele specific primers for PCR amplification can identify specific MHC alleles.

MHC compatibility between a donor and a recipient increases significantly if the donor cells are HLA homozygous, i.e. contain identical alleles for each antigen-presenting protein. Most individuals are heterozygous for MHC class I and II genes, but certain individuals are homozygous for these genes. These homozygous individuals can serve as super donors and grafts generated from their cells can be transplanted in all individuals that are either homozygous or heterozygous for that haplotype. Furthermore, if homozygous donor cells have a haplotype found in high frequency in a population, these cells may have application in transplantation therapies for a large number of individuals.

Accordingly, iPSCs can be produced from somatic cells of the subject to be treated, or another subject with the same or substantially the same HLA type as that of the patient. In one case, the major HLAs (e.g., the three major loci of HLA-A, HLA-B and HLA-DR) of the donor are identical to the major HLAs of the recipient. In some cases, the somatic cell donor may be a super donor; thus, iPSCs derived from a MHC homozygous super donor may be used to generate RPE cells. Thus, the iPSCs derived from a super donor may be transplanted in subjects that are either homozygous or heterozygous for that haplotype. For example, the iPSCs can be homozygous at two HLA alleles such as HLA-A and HLA-B. As such, iPSCs produced from super donors can be used in the methods disclosed herein, to produce RPE cells that can potentially "match" a large number of potential recipients.

2. Episomal Vectors

In certain aspects, reprogramming factors are expressed from expression cassettes comprised in one or more exogenous episomal genetic elements (see U.S. Patent Publication 2010/0003757, incorporated herein by reference). Thus, iPSCs can be essentially free of exogenous genetic elements, such as from retroviral or lentiviral vector elements. These iPSCs are prepared by the use of extra-chromosomally replicating vectors (i.e., episomal vectors), which are vectors capable of replicating episomally to make iPSCs essentially free of exogenous vector or viral elements (see U.S. Pat. No. 8,546,140, incorporated herein by reference; Yu et al., 2009). A number of DNA viruses, such as adenoviruses, Simian vacuolating virus 40 (SV40) or bovine papilloma virus (BPV), or budding yeast ARS (Autonomously Replicating Sequences)-containing plasmids replicate extra-chromosomally or episomally in mammalian cells. These episomal plasmids are intrinsically free from all these disadvantages (Bode et al., 2001) associated with integrating vectors. For example, a lymphotrophic herpes virus-based including or Epstein Barr Virus (EBV) as defined above may replicate extra-chromosomally and help deliver reprogramming genes to somatic cells. Useful EBV elements are OriP and EBNA-1, or their variants or functional equivalents. An additional advantage of episomal vectors is that the exogenous elements will be lost with time after being introduced into cells, leading to self-sustained iPSCs essentially free of these elements.

Other extra-chromosomal vectors include other lymphotrophic herpes virus-based vectors. Lymphotrophic herpes virus is a herpes virus that replicates in a lymphoblast (e.g., a human B lymphoblast) and becomes a plasmid for a part of its natural life-cycle. Herpes simplex virus (HSV) is not a "lymphotrophic" herpes virus. Exemplary lymphotrophic herpes viruses include, but are not limited to EBV, Kaposi's sarcoma herpes virus (KSHV); Herpes virus saimiri (HS)

and Marek's disease virus (MDV). Also other sources of episome-based vectors are contemplated, such as yeast ARS, adenovirus, SV40, or BPV.

C. Somatic Cell Nuclear Transfer

Pluripotent stem cells can be prepared through the method of somatic cell nuclear transfer. Somatic cell nuclear transfer involves the transfer of a donor nucleus into a spindle-free oocyte. In one method, donor fibroblast nuclei from skin fibroblasts of a rhesus macaque are introduced into the cytoplasm of spindle-free, mature metaphase II rhesus macaque ooctyes by electrofusion (Byrne et al., 2007). The fused oocytes are activated by exposure to ionomycin, and then incubated until the blastocyst stage. The inner cell mass of selected blastocysts are then cultured to produce embryonic stem cell lines. The embryonic stem cell lines show normal ES cell morphology, express various ES cell markers, and differentiate into multiple cell types both in vitro and in vivo.

III. Retinal Pigment Epithelial Cells

RPE cells are produced in the methods disclosed herein. The cells in the retina that are directly sensitive to light are the photoreceptor cells. Photoreceptors are photosensitive neurons in the outer part of the retina and can be either rods or cones. In the process of phototransduction, the photoreceptor cells convert incident light energy focused by the lens to electric signals which are then sent via the optic nerve to the brain. Vertebrates have two types of photoreceptor cells including cones and rods. Cones are adapted to detect fine detail, central and color vision and function well in bright light. Rods are responsible for peripheral and dim light vision. Neural signals from the rods and cones undergo processing by other neurons of the retina.

The retinal pigment epithelium acts as a barrier between the bloodstream and the retina and closely interacts with photoreceptors in the maintenance of visual function. The retinal pigment epithelium is composed of a single layer of hexagonal cells that are densely packed with granules of melanin that absorbs light energy that arrives to the retina. The main functions of the specialized RPE cells include: transport of nutrients such as glucose, retinol, and fatty acids from the blood to the photoreceptors; transport of water, metabolic end products, and ions from the subretinal space to the blood; absorption of light and protection against photooxidation; reisomerization of all-trans-retinol into 11-cis-retinal; phagocytosis of shed photoreceptor membranes; and secretion of various essential factors for the structural integrity of the retina.

The retinal pigment epithelium expresses markers such as cellular retinaldehyde-binding protein (CRALBP), RPE65, best vitelliform macular dystrophy gene (VMD2), and pigment epithelium derived factor (PEDF). Malfunction of the retinal pigment epithelium is associated with a number of vision-altering conditions, such as retinal pigment epithelium detachment, dysplasia, atrophy, retinopathy, retinitis pigmentosa, macular dystrophy, or degeneration.

Retinal pigment epithelial (RPE) cells can be characterized based upon their pigmentation, epithelial morphology, and apical-basal polarity. Differentiated RPE cells can be visually recognized by their cobblestone morphology and the initial appearance of pigment. In addition, differentiated RPE cells have transepithelial resistance/TER, and transepithelial potential/TEP across the monolayer (TER>100 ohms. cm2; TEP>2 mV), transport fluid and $CO_2$ from the apical to basal side, and regulate a polarized secretion of cytokines.

RPE cells express several proteins that can serve as markers for detection by the use of methodologies, such as immunocytochemistry, Western blot analysis, flow cytometry, and enzyme-linked immunoassay (ELISA). For example, RPE-specific markers may include: cellular retinaldehyde binding protein (CRALBP), microphthalmia-associated transcription factor (MITF), tyrosinase-related protein 1 (TYRP-1), retinal pigment epithelium-specific 65 kDa protein (RPE65), premelanosome protein (PMEL17), bestrophin 1 (BEST1), and c-mer proto-oncogene tyrosine kinase (MERTK). RPE cells do not express (at any detectable level) the embryonic stem cells markers Oct-4, nanog or Rex-2. Specifically, expression of these genes is approximately 100-1000 fold lower in RPE cells than in ES cells or iPSC cells, when assessed by quantitative RT-PCR.

RPE cell markers may be detected at the mRNA level, for example, by reverse transcriptase polymerase chain reaction (RT-PCR), Northern blot analysis, or dot-blot hybridization analysis using sequence-specific primers in standard amplification methods using publicly available sequence data (GENBANK®). Expression of tissue-specific markers as detected at the protein or mRNA level is considered positive if the level is at least or about 2-, 3-, 4-, 5-, 6-, 7-, 8-, or 9-fold, and more particularly more than 10-, 20-, 30, 40-, 50-fold or higher above that of a control cell, such as an undifferentiated pluripotent stem cell or other unrelated cell type.

Dysfunction, injury, and loss of RPE cells are factors of many eye diseases and disorders including age-related macular degeneration (AMD), hereditary macular degenerations including Best disease, and retinitis pigmentosa. A potential treatment for such diseases is the transplantation of RPE cells into the retina of those in need of such treatment. It is speculated that the replenishment of RPE cells by their transplantation may delay, halt or reverse degradation, improve retinal function and prevent blindness stemming from such conditions. However, obtaining RPE cells directly from human donors and embryos is a challenge.

A. Derivation of RPE Cells from Embryoid Bodies of PSCs iPSCs reprogrammed using well-known reprogramming factors can give rise to ocular cells of neuronal lineage, including RPE cells (Hirami et al., 2009). PCT Publication No. 2014/121077, incorporated by reference herein in its entirety, discloses methods wherein embryoid bodies (EBs) produced from iPSCs are treated with Wnt and Nodal antagonists in suspension culture to induce expression of markers of retinal progenitor cells. This publication discloses methods wherein RPE cells are derived from iPSCs through a process of differentiation of EBs of the iPSCs into cultures highly enriched for RPE cells. For example, embryoid bodies are produced from iPSCs by the addition of a rho-associated coiled-coil kinase (ROCK) inhibitor and cultured in a first medium comprising two WNT pathway inhibitors and a Nodal pathway inhibitor. Further, the EBs are plated on a MATRIGEL™ coated tissue culture in a second medium that does not comprise basic fibroblast growth factor (bFGF), comprises a Nodal pathway inhibitor, comprises about 20 ng to about 90 ng of Noggin, and comprises about 1 to about 5% knock out serum replacement to form differentiating RPE cells. The differentiating RPE cells are cultured in a third medium comprising ACTIVIN and WNT3a. The RPE cells are then cultured in RPE medium that includes about 5% fetal serum, a canonical WNT inhibitor, a non-canonical WNT inhibitor, and inhibitors of the Sonic Hedgehog and FGF pathways to produce human RPE cells.

There are several disadvantages in the use of EBs for the production of differentiated cell type. For example, the production of EBs is a non-consistent and non-reproducible process as the efficiency varies. The size and shape of EBs produced from iPSCs or ES cells is not homogenous, and the production of EBS also involves a rate-limiting centrifugation treatment. The present disclosure provides methods that allow large-scale production of iPSC- or ES-derived cells needed for clinical, research or therapeutic applications that are independent of EBs.

B. Derivation of RPE Cells from Essentially Single Cell PSCs

In some embodiments, methods are provided for producing RPE cells from an essentially single cell suspension of pluripotent stem cells (PSCs) such as human iPSCs. In some embodiments, the PSCs are cultured to pre-confluency to prevent any cell aggregates. In certain aspects, the PSCs are dissociated by incubation with a cell dissociation enzyme, such as exemplified by TRYPSIN™ or TRYPLE™. PSCs can also be dissociated into an essentially single cell suspension by pipetting. In addition, Blebbistatin (e.g., about 2.5 µM) can be added to the medium to increase PSC survival after dissociation into single cells while the cells are not adhered to a culture vessel. A ROCK inhibitor instead of Blebbistatin may alternatively used to increase PSC survival after dissociated into single cells.

In order to efficiently differentiate RPE cells from the single cell PSCs, an accurate count of the input density can increase RPE differentiation efficiency. Thus, the single cell suspension of PSCs is generally counted before seeding. For example, the single cell suspension of PSCs is counted by a hemocytometer or an automated cell counter, such as VICELL® or TC20. The cells may be diluted to a cell density of about 10,000 to about 500,000 cells/mL, about 50,000 to about 200,000 cells/mL, or about 75,000 to about 150,000 cells/mL. In a non-limiting example, the single cell suspension of PSCs is diluted to a density of about 100,000 cells/mL in a fully defined cultured medium such as ESSENTIAL 8™ (E8™) medium.

Once a single cell suspension of PSCs is obtained at a known cell density, the cells are generally seeded in an appropriate culture vessel, such as a tissue culture plate, such as a flask, 6-well, 24-well, or 96-well plate. A culture vessel used for culturing the cell(s) can include, but is particularly not limited to: flask, flask for tissue culture, dish, petri dish, dish for tissue culture, multi dish, micro plate, micro-well plate, multi plate, multi-well plate, micro slide, chamber slide, tube, tray, CELLSTACK® Chambers, culture bag, and roller bottle, as long as it is capable of culturing the stem cells therein. The cells may be cultured in a volume of at least or about 0.2, 0.5, 1, 2, 5, 10, 20, 30, 40, 50 ml, 100 ml, 150 ml, 200 ml, 250 ml, 300 ml, 350 ml, 400 ml, 450 ml, 500 ml, 550 ml, 600 ml, 800 ml, 1000 ml, 1500 ml, or any range derivable therein, depending on the needs of the culture. In a certain embodiment, the culture vessel may be a bioreactor, which may refer to any device or system ex vivo that supports a biologically active environment such that cells can be propagated. The bioreactor may have a volume of at least or about 2, 4, 5, 6, 8, 10, 15, 20, 25, 50, 75, 100, 150, 200, 500 liters, 1, 2, 4, 6, 8, 10, 15 cubic meters, or any range derivable therein.

In certain aspects, the PSCs, such as iPSCs, are plated at a cell density appropriate for efficient differentiation. Generally, the cells are plated at a cell density of about 1,000 to about 75,000 cells/cm$^2$, such as of about 5,000 to about 40,000 cells/cm$^2$. In a 6 well plate, the cells may be seeded at a cell density of about 50,000 to about 400,000 cells per well. In exemplary methods, the cells are seeded at a cell density of about 100,000, about 150,00, about 200,000, about 250,000, about 300,000 or about 350,000 cells per well, such as about 200,00 cells per well.

The PSCs, such as iPSCs, are generally cultured on culture plates coated by one or more cellular adhesion proteins to promote cellular adhesion while maintaining cell viability. For example, preferred cellular adhesion proteins include extracellular matrix proteins such as vitronectin, laminin, collagen and/or fibronectin which may be used to coat a culturing surface as a means of providing a solid support for pluripotent cell growth. The term "extracellular matrix" is recognized in the art. Its components include one or more of the following proteins: fibronectin, laminin, vitronectin, tenascin, entactin, thrombospondin, elastin, gelatin, collagen, fibrillin, merosin, anchorin, chondronectin, link protein, bone sialoprotein, osteocalcin, osteopontin, epinectin, hyaluronectin, undulin, epiligrin, and kalinin. In exemplary methods, the PSCs are grown on culture plates coated with vitronectin or fibronectin. In some embodiments, the cellular adhesion proteins are human proteins.

The extracellular matrix (ECM) proteins may be of natural origin and purified from human or animal tissues or, alternatively, the ECM proteins may be genetically engineered recombinant proteins or synthetic in nature. The ECM proteins may be a whole protein or in the form of peptide fragments, native or engineered. Examples of ECM protein that may be useful in the matrix for cell culture include laminin, collagen I, collagen IV, fibronectin and vitronectin. In some embodiments, the matrix composition includes synthetically generated peptide fragments of fibronectin or recombinant fibronectin. In some embodiments, the matrix composition is xeno-free. For example, in the xeno-free matrix to culture human cells, matrix components of human origin may be used, wherein any non-human animal components may be excluded.

In some aspects, the total protein concentration in the matrix composition may be about 1 ng/mL to about 1 mg/mL. In some preferred embodiments, the total protein concentration in the matrix composition is about 1 µg/mL to about 300 µg/mL. In more preferred embodiments, the total protein concentration in the matrix composition is about 5 µg/mL to about 200 µg/mL.

Cells, such as RPE cells or PSC, can be cultured with the nutrients necessary to support the growth of each specific population of cells. Generally, the cells are cultured in growth media including a carbon source, a nitrogen source and a buffer to maintain pH. The medium can also contain fatty acids or lipids, amino acids (such as non-essential amino acids), vitamin(s), growth factors, cytokines, antioxidant substances, pyruvic acid, buffering agents, and inorganic salts. An exemplary growth medium contains a minimal essential media, such as Dulbecco's Modified Eagle's medium (DMEM) or ESSENTIAL 8™ (E8™) medium, supplemented with various nutrients, such as non-essential amino acids and vitamins, to enhance stem cell growth. Examples of minimal essential media include, but are not limited to, Minimal Essential Medium Eagle (MEM) Alpha medium, Dulbecco's modified Eagle medium (DMEM), RPMI-1640 medium, 199 medium, and F12 medium. Additionally, the minimal essential media may be supplemented with additives such as horse, calf or fetal bovine serum. Alternatively, the medium can be serum free. In other cases, the growth media may contain "knockout serum replacement," referred to herein as a serum-free formulation optimized to grow and maintain undifferentiated cells, such as stem cell, in culture. KNOCKOUT™ serum replacement is disclosed, for example, in U.S. Patent Application No. 2002/0076747, which is incorporated herein by reference. Preferably, the PSCs are cultured in a fully defined and feeder free media.

Accordingly, the single cell PSCs are generally cultured in a fully defined culture medium after plating. In certain aspects, about 18-24 hours after seeding, the medium is aspirated and fresh medium, such as E8™ medium, is added to the culture. In certain aspects, the single cell PSCs are cultured in the fully defined culture medium for about 1, 2 or 3 days after plating. Preferably, the single cells PSCs are cultured in the fully defined culture medium for about 2 days before proceeding with the differentiation process.

In some embodiments, the medium may contain or may not contain any alternatives to serum. The alternatives to serum can include materials which appropriately contain albumin (such as lipid-rich albumin, albumin substitutes such as recombinant albumin, plant starch, dextrans and protein hydrolysates), transferrin (or other iron transporters), fatty acids, insulin, collagen precursors, trace elements, 2-mercaptoethanol, 3'-thiolglycerol, or equivalents thereto. The alternatives to serum can be prepared by the method disclosed in International Publication No. WO 98/30679, for example. Alternatively, any commercially available materials can be used for more convenience. The commercially available materials include KNOCKOUT™ Serum Replacement (KSR), Chemically-defined Lipid concentrated (Gibco), and GLUTAMAX™ (Gibco).

Other culturing conditions can be appropriately defined. For example, the culturing temperature can be about 30 to 40° C., for example, at least or about 31, 32, 33, 34, 35, 36, 37, 38, 39° C. but particularly not limited to them. In one embodiment, the cells are cultured at 37° C. The CO2 concentration can be about 1 to 10%, for example, about 2 to 5%, or any range derivable therein. The oxygen tension can be at least, up to, or about 1, 2, 3, 4, 5, 6, 7, 8, 9, 10, 20%, or any range derivable therein.

a. Differentiation Media

Retinal Induction Medium

After the single cell PSCs have adhered to the culture plate, the cells are preferably cultured in Retinal Induction Medium to start the differentiation process into retinal lineage cells. The Retinal Induction Medium (RIM) comprises a WNT pathway inhibitor and can result in the differentiation of PSCs to retinal lineage cells. The RIM additionally comprises a TGFβ pathway inhibitor and a BMP pathway inhibitor. One exemplary RIM medium is shown in Table 3.

The RIM can include DMEM and F12 at about a 1:1 ratio. In exemplary methods, a WNT pathway inhibitor is included in the RIM, such as CKI-7, a BMP pathway inhibitor is included, such as LDN193189, and the TGFβ pathway inhibitor is included, such as SB431542. For example, the RIM comprises about 5 nM to about 50 nM, such as about 10 nM, of LDN193189, about 0.1 μM to about 5 μM, such as about 0.5 μM, of CKI-7, and about 0.5 μM to about 10 μM, such as about 1 μM, of SB431542. Additionally, the RIM can include knockout serum replacement, such as about 1% to about 5%, MEM non-essential amino acids (NEAA), sodium pyruvate, N-2 supplement, B-27 supplement, ascorbic acid, and insulin growth factor 1 (IGF1). Preferably, the IGF1 is animal free IGF1 (AF-IGF1) and is comprised in the RIM from about 0.1 ng/mL to about 10 ng/mL, such as about 1 ng/mL. The media is such as aspirated each day and replaced with fresh RIM. The cells are generally cultured in the RIM for about 1 to about 5 days, such as about 1, 2, 3, 4 or 5 days, such as for about 2 days to produce retinal lineage cells.

Retinal Differentiation Medium

The retinal lineage cells can then be cultured in Retinal Differentiation Medium (RDM) for further differentiation. The RDM comprises a WNT pathway inhibitor, a BMP pathway inhibitor, a TGFβ pathway inhibitor and a MEK inhibitor. In one embodiment, the RDM comprises a WNT pathway inhibitor, such as CKI-7, a BMP pathway inhibitor, such as LDN193189, a TGFβ pathway inhibitor, such as SB431542, and a MEK inhibitor, such as PD0325901. Alternatively, the RDM can comprise a WNT pathway inhibitor, a BMP pathway inhibitor, a TGFβ pathway inhibitor and a bFGF inhibitor. Generally, the concentrations of the Wnt pathway inhibitor, BMP pathway inhibitor and TGFβ pathway inhibitor are higher in the RDM as compared to the RIM, such as about 9 to about 11 times higher, such as about 10 times higher. In exemplary methods, the RDM comprises about 50 nM to about 200 nM, such as about 100 nM of LDN193189, about 1 μM to about 10 μM, such as about 5 μM, of CKI-7, about 1 μM to about 50 μM, such as about 10 μM, of SB431542, and about 0.1 μM to about 10 μM, such as about 1 μM, 2 μM, 3 μM, 4 μM, 5 μM, 6 μM, 7 μM, 8 μM, or 9 μM of PD0325901. One exemplary RDM medium is shown in Table 3.

Generally, the RDM comprises DMEM and F12 at about a 1:1 ratio, knockout serum replacement (e.g., about 1% to about 5%, such as about 1.5%), MEM NEAA, sodium pyruvate, N-2 supplement, B-27 supplement, ascorbic acid and IGF1 (e.g., about 1 ng/mL to about 50 ng/mL, such as about 10 ng/mL). In particular methods, the cells are given fresh RDM each day after aspiration of the media from the previous day. Generally, the cells are cultured in the RDM for about 2, 3, 4, 5, 6, 7, 8, 9, 10, 11, 12, 13, 14, 15, or 16 days, such as for about 7 days to derive differentiated retinal cells.

Retinal Medium

Next, the differentiated retinal cells can be even further differentiated by culturing the cells in Retinal Medium (RM). The Retinal Medium comprises Activin A and can additionally comprise Nicotinamide. The RM can comprise about 50 to about 200 ng/mL, such as about 100 ng/mL, of ACTIVIN A, and about 1 mM to about 50 mM, such as about 10 mM, of nicotinamide. Alternatively, the RM can comprise other TGF-β pathway activators such as GDF1 and/or WNT pathway activators such as WAY-316606, IQ1, QS11, SB-216763, BIO (6-bromoindirubin-3'-oxime), or 2-amino-4-[3,4-(methylenedioxy)benzyl-amino]-6-(3-methoxyphenyl) pyrimidine. Alternatively, the RM can additionally comprise WNT3a. One exemplary RM medium is shown in Table 3.

The RM can include DMEM and F12 at about a 1:1 ratio, knockout serum replacement at about 1% to about 5%, such as about 1.5%, MEM non-essential amino acids (NEAA), sodium pyruvate, N-2 supplement, B-27 supplement, and ascorbic acid. The medium can be changed daily with room temperature RM. The cells are generally cultured in the RM for about 8, 9, 10, 11, 12, 13, 14, 15, 16 or 17 days, such as for about 10 days to derive differentiating RPE cells.

RPE-Maturation Medium

For further differentiation of the RPE cells, the cells are preferably cultured in RPE Maturation Medium (RPE-MM). Exemplary RPE-MM media are shown in Table 3. The RPE-Maturation Medium can comprise about 100 μg/mL to about 300 μg/mL, such as about 250 μg/mL, of taurine, about 10 μg/L to about 30 μg/L, such as about 20 μg/L, of hydrocortisone and about 0.001 μg/L to about 0.1 μg/L, such as about 0.013 µg/L, of triiodothyronine. Additionally, the RPE-MM can comprise MEM Alpha, N-2 supplement, MEM non-essential amino acids (NEAA), and sodium pyruvate, and fetal bovine serum (e.g., about 0.5% to about 10%, such as about 1% to about 5%). The medium can be changed every other day with room temperature RPE-MM. The cells are generally cultured in RPE-MM for about 5 to about 10 days, such as about 5 days. The cells can then be dissociated, such as with a cell dissociation enzyme, reseeded, and cultured for an additional period of time, such as an additional about 5 to about 30 days, such as about 15 to 20 days, for further differentiation into RPE cells. In further embodiments, the RPE-MM does not include a WNT pathway inhibitor. RPE cells can be cryopreserved at this stage.

b. Maturation of RPE Cells

The RPE cells can then be cultured in the RPE-MM for a continued period of time for maturation. In some embodiments, the RPE cells are grown in wells, such as a 6-well, 12-well, 24-well, or 10 cm plate. The RPE cells can be maintained in RPE medium for about four to about ten weeks, such as for about six to eight weeks, such as for six, seven, or eight weeks. In exemplary methods for the continued maturation of the RPE cells, the cells can be dissociated in a cell dissociated enzyme such as TRYPLE™ and reseeded on a degradable scaffold assembly such as in a specialized SNAPWELL™ design for about one to two weeks in RPE-MM with a MEK inhibitor such as PD0325901. Alternatively, the RPE-MM can comprise a bFGF inhibitor instead of the MEK inhibitor. The methods for culturing RPE cells on a degradable scaffold are taught and described in PCT Publication No. WO 2014/121077, which is incorporated herein by reference in its entirety. Briefly, the main components of this method are a CORNING® COSTAR® SNAPWELL™ plate, a bioinert 0-ring, and a biodegradable scaffold. SNAPWELL™ plates provide the structure and platform for the biodegradable scaffolds. The microporous membrane that creates an apical and basal side is ideal for providing support to the scaffold as well as isolating the distinct sides of the polarized layer of cells. The ability of the SNAPWELL™ insert to detach the membrane allows the support ring of the insert to be used an anchor for the scaffold. The resulting differentiated, polarized, and confluent monolayers of functional RPE cells can be cryopreserved at this stage (e.g., in xenofree CS10 medium).

In some embodiment, mature RPE cells can be further developed into functional RPE cell monolayers that behave as intact RPE tissue by continued culture in the RPE-MM with additional chemicals or small molecules that promote RPE maturation. For example, these small molecules are primary cilium inducers such as prostaglandin E2 (PGE2) or aphidicolin. The PGE2 may be added to the medium at a concentration of about 25 µM to about 250 µM, such as about 50 µM to about 100 µM. Alternatively, the RPE-MM can comprise canonical WNT pathway inhibitors. Exemplary canonical WNT pathway inhibitors are N-(6-Methyl-2-benzothiazolyl)-2-[(3,4,6,7-tetrahydro-4-oxo-3-phenylthieno[3,2-d]pyrimidin-2-yl)thio]-acetamide (IWP2) or 4-(1,3,3a,4,7,7a-Hexahydro-1,3-dioxo-4,7-methano-2H-isoindol-2-yl)-N-8-quinolinyl-Benzamide (endo-IWR1). The cells are can be cultured in this medium for an additional period of time, such as an additional about one week to about five weeks, such as about another two to four weeks to obtain mature and functional RPE cell monolayers. Thus, the presently disclosed methods provide mature RPE cells from single cell suspensions of pluripotent cells that can be consistently reproduced at a large scale for clinical applications.

c. Cryopreservation of RPE Cells

The retinal pigment epithelial cells produced by the methods disclosed herein can be cryopreserved, see for example, PCT Publication No. 2012/149484 A2, which is incorporated by reference herein. The cells can be cryopreserved with or without a substrate. In several embodiments, the storage temperature ranges from about −50° C. to about −60° C., about −60° C. to about −70° C., about −70° C. to about −80° C., about −80° C. to about −90° C., about −90° C. to about −100° C., and overlapping ranges thereof. In some embodiments, lower temperatures are used for the storage (e.g., maintenance) of the cryopreserved cells. In several embodiments, liquid nitrogen (or other similar liquid coolant) is used to store the cells. In further embodiments, the cells are stored for greater than about 6 hours. In additional embodiments, the cells are stored about 72 hours. In several embodiments, the cells are stored 48 hours to about one week. In yet other embodiments, the cells are stored for about 1, 2, 3, 4, 5, 6, 7, or 8 weeks. In further embodiments, the cells are stored for 1, 2, 3, 4, 5, 67, 8, 9, 10, 11 or 12 months. The cells can also be stored for longer times. The cells can be cryopreserved separately or on a substrate, such as any of the substrates disclosed herein.

In some embodiments, additional cryoprotectants can be used. For example, the cells can be cryopreserved in a cryopreservation solution comprising one or more cryoprotectants, such as DM80, serum albumin, such as human or bovine serum albumin. In certain embodiments, the solution comprises about 1%, about 1.5%, about 2%, about 2.5%, about 3%, about 4%, about 5%, about 6%, about 7%, about 8%, about 9%, or about 10% DMSO. In other embodiments, the solution comprises about 1% to about 3%, about 2% to about 4%, about 3% to about 5%, about 4% to about 6%, about 5% to about 7%, about 6% to about 8%, about 7% to about 9%, or about 8% to about 10% dimethylsulfoxide (DMSO) or albumin. In a specific embodiment, the solution comprises 2.5% DMSO. In another specific embodiment, the solution comprises 10% DMSO.

Cells may be cooled, for example, at about 1° C. minute during cryopreservation. In some embodiments, the cryopreservation temperature is about −80° C. to about −180° C., or about −125° C. to about −140° C. In some embodiments, the cells are cooled to 4° C. prior to cooling at about 1° C./minute. Cryopreserved cells can be transferred to vapor phase of liquid nitrogen prior to thawing for use. In some embodiments, for example, once the cells have reached about −80° C., they are transferred to a liquid nitrogen storage area. Cryopreservation can also be done using a controlled-rate freezer. Cryopreserved cells may be thawed, e.g., at a temperature of about 25° C. to about 40° C., and typically at a temperature of about 37° C.

d. Inhibitors

WNT Pathway Inhibitors

WNT is a family of highly conserved secreted signaling molecules that regulate cell-to-cell interactions and are related to the *Drosophila* segment polarity gene, wingless. In humans, the WNT family of genes encodes 38 to 43 kDa cysteine rich glycoproteins. The WNT proteins have a hydrophobic signal sequence, a conserved asparagine-linked oligosaccharide consensus sequence (see e.g., Shimizu et al Cell Growth Differ 8: 1349-1358 (1997)) and 22 conserved cysteine residues. Because of their ability to promote stabilization of cytoplasmic beta-catenin, WNT proteins can act as transcriptional activators and inhibit apoptosis. Overexpression of particular WNT proteins has been shown to be associated with certain cancers.

A WNT inhibitor herein refers to WNT inhibitors in general. Thus, a WNT inhibitor refers to any inhibitor of a member of the WNT family proteins including Wnt1, Wnt2, Wnt2b, Wnt3, Wnt4, Wnt5A, Wnt6, Wnt7A, Wnt7B, Wnt8A, Wnt9A, Wnt10a, Wnt11, and Wnt16. Certain embodiments of the present methods concern a WNT inhibitor in the differentiation medium. Examples of suitable WNT inhibitors, already known in the art, include N-(2-Aminoethyl)-5-chloroisoquinoline-8-sulphonamide dihydrochloride (CKI-7), N-(6-Methyl-2-benzothiazolyl)-2-[(3,4,6,7-tetrahydro-4-oxo-3-phenylthieno[3,2-d]pyrimidin-2-yl)thio]-acetamide (IWP2), N-(6-Methyl-2-benzothiazolyl)-2-[(3,4,6,7-tetrahydro-3-(2-methoxyphenyl)-4-oxothieno[3,2-d]pyrimidin-2-yl)thio]-acetamide (IWP4), 2-Phenoxybenzoic acid-[(5-methyl-2-furanyl)methylene] hydrazide (PNU 74654) 2,4-diamino-quinazoline, quercetin, 3,5,7,8-Tetrahydro-2-[4-(trifluoromethyl)phenyl]-4H-thiopyrano[4,3-d]pyrimidin-4-one (XAV939), 2,5-Dichloro-N-(2-methyl-4-nitrophenyl)benzenesulfonamide (FH 535), N-[4-[2-Ethyl-4-(3-methylphenyl)-5-thiazolyl]-2-pyridinyl] benzamide (TAK 715), Dickkopf-related protein one (DKK1), and Secreted frizzled-related protein (SFRP1) 1. In addition, inhibitors of WNT can include antibodies to, dominant negative variants of, and siRNA and antisense nucleic acids that suppress expression of WNT. Inhibition of WNT can also be achieved using RNA-mediated interference (RNAi).

BMP Pathway Inhibitors

Bone morphogenic proteins (BMPs) are multi-functional growth factors that belong to the transforming growth factor beta (TGFβ) superfamily. BMPs are considered to constitute a group of pivotal morphogenetic signals, orchestrating architecture through the body. The important functioning of BMP signals in physiology is emphasized by the multitude of roles for dysregulated BMP signaling in pathological processes.

BMP pathway inhibitors may include inhibitors of BMP signaling in general or inhibitors specific for BMP1, BMP2, BMP3, BMP4, BMP5, BMP6, BMP7, BMP8a, BMP8b, BMP10 or BMP15. Exemplary BMP inhibitors include 4-(6-(4-(piperazin-1-yl)phenyl)pyrazolo[1,5-a]pyrimidin-3-yl)quinoline hydrochloride (LDN193189), 6-[4-[2-(1-Piperidinyl)ethoxy]phenyl]-3-(4-pyridinyl)-pyrazolo[1,5-a]pyrimidine dihydrochloride (Dorsomorphin), 4-[6-[4-(1-Methylethoxy)phenyl]pyrazolo[1,5-a]pyrimidin-3-yl]-quinoline (DMH1), 4-[6-[4-[2-(4-Morpholinyl)ethoxy] phenyl]pyrazolo[1,5-a]pyrimidin-3-yl]quinoline (DMH-2), and 5-[6-(4-Methoxyphenyl)pyrazolo[1,5-a]pyrimidin-3-yl] quinoline (ML 347).

TGFβ Pathway Inhibitors

Transforming growth factor beta (TGFβ) is a secreted protein that controls proliferation, cellular differentiation, and other functions in most cells. It is a type of cytokine which plays a role in immunity, cancer, bronchial asthma, lung fibrosis, heart disease, diabetes, and multiple sclerosis. TGF-β exists in at least three isoforms called TGF-β1, TGF-β2 and TGF-β3. The TGF-β family is part of a superfamily of proteins known as the transforming growth factor beta superfamily, which includes inhibins, activin, anti-müllerian hormone, bone morphogenetic protein, decapentaplegic and Vg-1.

TGFβ pathway inhibitors may include any inhibitors of TGFβ signaling in general. For example, the TGFβ pathway inhibitor is 4-[4-(1,3-benzodioxol-5-yl)-5-(2-pyridinyl)-1H-imidazol-2-yl]benzamide (SB431542), 6-[2-(1,1-Dimethylethyl)-5-(6-methyl-2-pyridinyl)-1H-imidazol-4-yl]quinoxaline (SB525334), 2-(5-Benzo[1,3]dioxol-5-yl-2-tert-butyl-3H-imidazol-4-yl)-6-methylpyridine hydrochloride hydrate (SB-505124), 4-(5-Benzol[1,3]dioxol-5-yl-4-pyridin-2-yl-1H-imidazol-2-yl)-benzamide hydrate, 4-[4-(1,3-Benzodioxol-5-yl)-5-(2-pyridinyl)-1H-imidazol-2-yl]-benzamide hydrate, left-right determination factor (Lefty), 3-(6-Methyl-2-pyridinyl)-N-phenyl-4-(4-quinolinyl)-1H-pyrazole-1-carbothioamide (A 83-01), 4-[4-(2,3-Dihydro-1,4-benzodioxin-6-yl)-5-(2-pyridinyl)-1H-imidazol-2-yl]benzamide (D 4476), 4-[4-[3-(2-Pyridinyl)-1H-pyrazol-4-yl]-2-pyridinyl]-N-(tetrahydro-2H-pyran-4-yl)-benzamide (GW 788388), 4-[3-(2-Pyridinyl)-1H-pyrazol-4-yl]-quinoline (LY 364847), 4-[2-Fluoro-5-[3-(6-methyl-2-pyridinyl)-1H-pyrazol-4-yl] phenyl]-1H-pyrazole-1-ethanol (R 268712) or 2-(3-(6-Methylpyridine-2-yl)-1H-pyrazol-4-yl)-1,5-naphthyridine (RepSox).

MEK Inhibitors

A MEK inhibitor is a chemical or drug that inhibits the mitogen-activated protein kinase enzymes MEK1 or MEK2. They can be used to affect the MAPK/ERK pathway. For example, MEK inhibitors include N-[(2R)-2,3-Dihydroxypropoxy]-3,4-difluoro-2-[(2-fluoro-4-iodophenyl)amino]-benzamide (PD0325901), N-[3-[3-cyclopropyl-5-(2-fluoro-4-iodoanilino)-6,8-dimethyl-2,4,7-trioxopyrido[4,3-d] pyrimidin-1-yl]phenyl]acetamide (GSK1120212), 6-(4-bromo-2-fluoro anilino)-7-fluoro-N-(2-hydroxyethoxy)-3-methylbenzimidazole-5-carboxamide (MEK162), N-[3,4-difluoro-2-(2-fluoro-4-iodoanilino)-6-methoxyphenyl]-1-(2,3-dihydroxypropyl)cyclopropane-1-sulfonamide (RDEA119), and 6-(4-bromo-2-chloroanilino)-7-fluoro-N-(2-hydroxyethoxy)-3-methylbenzimidazole-5-carboxamide (AZD6244).

bFGF Inhibitors

Basic fibroblast growth factor (also known as bFGF, FGF2 or FGF-β) is a member of the fibroblast growth factor family. bFGF is present in basement membranes and in the subendothelial extracellular matrix of blood vessels. In addition, bFGF is a common component of human ESC culture medium in which it is necessary for the cells to remain in an undifferentiated state.

bFGF inhibitors herein refer to bFGF inhibitors in general. For example, bFGF inhibitors include, but are not limited to N-[2-[[4-(Diethylamino)butyl]amino-6-(3,5-dimethoxyphenyl)pyrido[2,3-d]pyrimidin-7-yl]-N'-(1,1-dimethylethyl)urea (PD173074), 2-(2-Amino-3-methoxyphenyl)-4H-1-benzopyran-4-one (PD 98059), 1-tert-Butyl-3-[6-(2,6-dichlorophenyl)-2-[[4-(diethylamino)butyl]amino] pyrido[2,3-d]pyrimidin-7-yl]urea (PD161570), 6-(2,6-Dichlorophenyl)-2-[[4-[2-(diethylamino)ethoxy]phenyl] amino]-8-methyl-pyrido[2,3-d]pyrimidin-7(8H)-one dihydrochloride hydrate (PD166285), N-[2-Amino-6-(3,5-dimethoxyphenyl)pyrido[2,3-d]pyrimidin-7-yl]-N'-(1,1-dimethylethyl)-urea (PD166866), and MK-2206.

IV. Use of Retinal Pigment Epithelial Cells

Certain aspects provide a method to produce an RPE or RPE-enriched cell population which can be used for a number of important research, development, and commercial purposes.

In some aspects, the methods disclosed herein result in a cell population of at least or about $10^6$, $10^7$, $10^8$, $5\times10^8$, $10^9$, $10^{10}$ cells (or any range derivable therein) comprising at least or about 90% (for example, at least or about 90%, 95%, 96%, 97%, 98%, 99%, 99.5%, or any range derivable therein) RPE cells.

In certain aspects, starting cells for the present methods may comprise the use of at least or about $10^4$, $10^5$, $10^6$, $10^7$, $10^8$, $10^9$, $10^{10}$, $10^{11}$, $10^{12}$, $10^{13}$ cells or any range derivable therein. The starting cell population may have a seeding density of at least or about 10, $10^1$, $10^2$, $10^3$, $10^4$, $10^5$, $10^6$, $10^7$, $10^8$ cells/ml, or any range derivable therein.

The RPE cells produced by the methods disclosed herein may be used in any methods and applications currently known in the art for RPE cells. For example, a method of assessing a compound may be provided, comprising assaying a pharmacological or toxicological property of the compound on the RPE cell. There may also be provided a method of assessing a compound for an effect on a RPE cell, comprising: a) contacting the RPE cells provided herein with the compound; and b) assaying an effect of the compound on the RPE cells.

A. Test Compound Screening

RPE cells can be used commercially to screen for factors (such as solvents, small molecule drugs, peptides, oligonucleotides) or environmental conditions (such as culture conditions or manipulation) that affect the characteristics of such cells and their various progeny. For example, test compounds may be chemical compounds, small molecules, polypeptides, growth factors, cytokines, or other biological agents.

In one embodiment, a method includes contacting a RPE cell with a test agent and determining if the test agent modulates activity or function of RPE cells within the population. In some applications, screening assays are used for the identification of agents that modulate RPE cell proliferation or alter RPE cell differentiation. Screening assays may be performed in vitro or in vivo. Methods of screening and identifying ocular agents or RPE agents include those suitable for high-throughput screening. For example, RPE cells can be positioned or placed on a culture dish, flask, roller bottle or plate (e.g., a single multi-well dish or dish such as 8, 16, 32, 64, 96, 384 and 1536 multi-well plate or dish), optionally at defined locations, for identification of potentially therapeutic molecules. Libraries that can be screened include, for example, small molecule libraries, siRNA libraries, and adenoviral transfection vector libraries.

Other screening applications relate to the testing of pharmaceutical compounds for their effect on retinal tissue maintenance or repair. Screening may be done either because the compound is designed to have a pharmacological effect on the cells, or because a compound designed to have effects elsewhere may have unintended side effects on cells of this tissue type.

B. Therapy and Transplantation

Other embodiments can also provide use of RPE cells to enhance ocular tissue maintenance and repair for any condition in need thereof, including retinal degeneration or significant injury.

To determine suitability of cell compositions for therapeutics administration, the cells can first be tested in a suitable animal model. In one aspect, the RPE cells are evaluated for their ability to survive and maintain their phenotype in vivo. Cell compositions are administered to immunodeficient animals (e.g., nude mice or animals rendered immunodeficient chemically or by irradiation). Tissues are harvested after a period of growth, and assessed as to whether the pluripotent stem cell-derived cells are still present.

A number of animals are available for testing of the suitability of the RPE cell compositions. For example, the Royal College of Surgeon's (RCS) rat is a well known model of retinal dystrophy (Lund et al., 2006). In addition, RPE cell suitability and survival can be determined by transplantation (e.g. subcutaneous or subretinal) in matrigel in immunodeficient animals such as NOG mice (Kanemura et al., 2014).

The human RPE cells described herein, or a pharmaceutical composition including these cells, can be used for the manufacture of a medicament to treat a condition in a patient in need thereof. The RPE cells can be previously cryopreserved. In certain aspects, the disclosed RPE cells are derived from iPSCs, and thus can be used to provide "personalized medicine" for patients with eye diseases. In some embodiments, somatic cells obtained from patients can be genetically engineered to correct the disease causing mutation, differentiated into RPE, and engineered to form an RPE tissue. This RPE tissue can be used to replace the endogenous degenerated RPE of the same patient. Alternatively, iPSCs generated from a healthy donor or from HLA homozygous "super-donors" can be used. RPE cells can be treated in vitro with certain factors, such as pigment epithelium-derived factor (PEDF), transforming growth factor (TGF)-beta, and/or retinoic acid to generate an anti-inflammatory and immunosuppressive environment in vivo.

Various eye conditions may be treated or prevented by the introduction of the RPE cells obtained using the methods disclosed herein. The conditions include retinal diseases or disorders generally associated with retinal dysfunction or degradation, retinal injury, and/or loss of retinal pigment epithelium. Conditions that can be treated include, without limitation, degenerative diseases of the retina, such as Stargardt's macular dystrophy, retinitis pigmentosa, macular degeneration (such as age related macular degeneration), glaucoma, and diabetic retinopathy. Additional conditions include Lebers congenital amaurosis, hereditary or acquired macular degeneration, Best disease, retinal detachment, gyrate atrophy, choroideremia, pattern dystrophy, other dystrophies of the RPE, and RPE and retinal damage due to damage caused by any one of photic, laser, inflammatory, infectious, radiation, neovascular or traumatic injury. In certain embodiments, methods are provided for treating or preventing a condition characterized by retinal degeneration, comprising administering to a subject in need thereof an effective amount of a composition comprising RPE cells. These methods can include selecting a subject with one or more of these conditions, and administering a therapeutically effective amount of the RPE cells sufficient to treat the condition and/or ameliorate symptoms of the condition. The RPE cells may be transplanted in various formats. For example, the RPE cells may be introduced into the target site in the form of cell suspension, or adhered onto a matrix, extracellular matrix or substrate such as a biodegradable polymer, as a monolayer, or a combination. The RPE cells may also be transplanted together (co-transplantation) with other retinal cells, such as with photoreceptors. In some embodiments, the RPE cells are produced from iPSCs from the subject to be treated, and thus are autologous. In other embodiments, the RPE cells are produced from an MHC-matched donor.

In some embodiment, the RPE cells can be used for autologous RPE grafts to those subjects suitable for receiving regenerative medicine. The RPE cells may be transplanted in combination with other retinal cells, such as with photoreceptors. Transplantation of the RPE cells produced by the disclosed methods can be performed by various techniques known in the art. For example, methods for performed RPE transplants are described in U.S. Pat. Nos. 5,962,027 and 6,045,791, each of which is incorporated herein by reference in its entirety. In accordance with one embodiment, the transplantation is performed via pars pana vitrectomy surgery followed by delivery of the cells through a small retinal opening into the sub-retinal space or by direct injection. The RPE cells can be introduced into the target site in the form of cell suspension, adhered onto a matrix, such as extracellular matrix, or provided on substrate such as a biodegradable polymer. The RPE cells can also be transplanted together (co-transplantation) with other cells, such as retinal cells with photoreceptors. Thus, a composition comprising RPE cells obtained by the methods disclosed herein is provided. In some embodiments, these RPE cells include a tyrosinase enhancer operably linked to a promoter and a nucleic acid encoding a marker. In other embodiments, the RPE cells also include a second constitutive promoter operably linked to a nucleic acid encoding a second marker.

Pharmaceutical compositions of the RPE cells produced by the methods disclosed herein. These composition can include at least about $1 \times 10^3$ RPE cells, about $1 \times 10^4$ RPE cells, about $1 \times 10^5$ RPE cells, about $1 \times 10^6$ RPE cells, about $1 \times 10^7$ RPE cells, about $1 \times 10^8$ RPE cells, or about $1 \times 10^9$ RPE cells. In certain embodiments, the compositions are substantially purified (with respect to non-RPE cells) preparations comprising differentiated RPE cells produced by the methods disclosed herein. Compositions are also provided that include a scaffold, such as a polymeric carrier and/or an extracellular matrix, and an effective amount of the RPE cells produced by the methods disclosed herein. For example, the cells are provided as a monolayer of cells. The matrix material if generally physiologically acceptable and suitable for use in in vivo applications. For example, the physiologically acceptable materials include, but are not limited to, solid matrix materials that are absorbable and/or non-absorbable, such as small intestine submucosa (SIS), crosslinked or non-crosslinked alginate, hydrocolloid, foams, collagen gel, collagen sponge, polyglycolic acid (PGA) mesh, fleeces and bioadhesives.

Suitable polymeric carriers also include porous meshes or sponges formed of synthethic or natural polymers, as well as polymer solutions. For example, the matrix is a polymeric mesh or sponge, or a polymeric hydrogel. Natural polymers that can be used include proteins such as collagen, albumin, and fibrin; and polysaccharides such as alginate and polymers of hyaluronic acid. Synthetic polymers include both biodegradable and non-biodegradable polymers. For example, biodegradable polymers include polymers of hydroxy acids such as polyactic acid (PLA), polyglycolic acid (PGA) and polylactic acid-glycolic acid (PGLA), polyorthoesters, polyanhydrides, polyphosphazenes, and combinations thereof. Non-biodegradable polymers include polyacrylates, polymethacrylates, ethylene vinyl acetate, and polyvinyl alcohols.

Polymers that can form ionic or covalently crosslinked hydrogels which are malleable can be used. A hydrogel is a substance formed when an organic polymer (natural or synthetic) is cross-linked via covalent, ionic, or hydrogen bonds to create a three-dimensional open-lattice structure which entraps water molecules to form a gel. Examples of materials which can be used to form a hydrogel include polysaccharides such as alginate, polyphosphazines, and polyacrylates, which are crosslinked ionically, or block copolymers such as PLURONICS™ or TETRONICS™, polyethylene oxide-polypropylene glycol block copolymers which are crosslinked by temperature or H, respectively. Other materials include proteins such as fibrin, polymers such as polyvinylpyrrolidone, hyaluronic acid and collagen.

The pharmaceutical compositions can be optionally packaged in a suitable container with written instructions for a desired purpose, such as the reconstitution of RPE cell function to improve a disease or abnormality of the retinal tissue. In some embodiments, the RPE cells produced by the disclosed methods may be engineered to form RPE, which can be used to replace degenerated RPE of a subject in need therein.

C. Distribution for Commercial, Therapeutic, and Research Purposes

In some embodiments, a reagent system is provided that includes a set or combination of cells comprising a RPE-enriched cell population that exists at any time during manufacture, distribution or use. The cell sets comprise any combination of the cell population described herein in combination with undifferentiated pluripotent stem cells or other differentiated cell types, often sharing the same genome. Each cell type may be packaged together, or in separate containers in the same facility, or at different locations, at the same or different times, under control of the same entity or different entities sharing a business relationship.

Pharmaceutical compositions may optionally be packaged in a suitable container with written instructions for a desired purpose, such as the reconstitution of RPE cell function to improve a disease or injury of the ocular tissue.

V. Kits

In some embodiments, a kit that can include, for example, one or more media and components for the production of RPE cells is provided. The reagent system may be packaged either in aqueous media or in lyophilized form, where appropriate. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The components of the kit may be provided as dried powder(s). When reagents and/or components are provided as a dry powder, the powder can be reconstituted by the addition of a suitable solvent. It is envisioned that the solvent may also be provided in another container means. The kits also will typically include a means for containing the kit component(s) in close confinement for commercial sale. Such containers may include injection or blow molded plastic containers into which the desired vials are retained. The kit can also include instructions for use, such as in printed or electronic format, such as digital format.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Preparation of Starting Pluripotent Stem Cell Population

A starting population of RPE cells can be derived from pluripotent stem cells such as ES cells and iPSCs. In exemplary methods, the RPE cells were derived from human iPSCs reprogrammed from somatic cells by methods known in the art such as U.S. Pat. Nos. 8,546,140, 8,741,648, 8,691,574, Published U.S. Patent Application No. 20090246875, Published U.S. Pat. No. 8,278,104, Published U.S. Pat. Nos. 9,005,967, 8,058,065, 8,129,187, PCT Publication NO. WO 2007/069666 A1, U.S. Pat. Nos. 8,183,038 and 8,268,620, which are incorporated herein by reference. For example, nuclear programming factors Oct4, Sox2, c-Myc and Klf4 were used to produce pluripotent stem cells from a somatic cell. In another exemplary method, nuclear programming factors Oct4, Sox2, Nanog, Lin28, L-Myc, and SV40 Large T-antigen were used to produce pluripotent stem cells from a somatic cell.

The iPSCs were grown without mouse or human feeder layers in fully defined-culture medium, such as ESSENTIAL 8™ (E8™) medium, on a plate coated by vitronectin. The vitronectin was diluted 1:200 in DPBS without calcium or magnesium and the culture plates were coated with the vitronectin and incubated at room temperature for about 1 hour. The iPSCs were split when they were pre-confluent and not allowed to overgrow to prevent unhealthy and/or differentiated cells (FIG. 1A).

In order to derive RPE cells, the iPSCs were dissociated into a single cell suspension to remove any aggregates or embryoid bodies. To obtain the single cell suspension, the cells were washed with DPBS and incubated in a cell dissociation enzyme such as TRYPLE™ for about 10 min at 37° C. The cells were then detached by pipetting with a serological pipet and the cell suspension was collected in a conical tube. If the cells did not detach with gently pipetting, the cultures were allowed to incubate longer, such as 2-3 additional minutes. To collect all of the cells, the culture vessel was washed with room temperature E8™ medium and the medium was then added to the tube containing the cell suspension. In addition, Blebbistatin (e.g. 2.5 µM) was added to the E8™ Medium to increase PSC survival after dissociation into single cells while the cells are not adhered to a culture vessel. To collect the cells, they were centrifuged at 400×g for about 5 minutes, the supernatant was aspirated and the cells were resuspended in an appropriate volume of E8™ medium.

In order to efficiently differentiate RPE cells from the single cell iPSCs, the input density of the single cell iPSCs was accurately counted by an automated cell counter such as VICELL™ and diluted to a cell suspension of about 1×10⁵ cells/mL in room temperature E8™ medium. Once the single cell suspension of iPSCs was obtained at a known cell density, the cells were plated in an appropriate culture vessel such as a 6-well plate coated with vitronectin. The cells were seeded at a cell density of about 200,000 cells per well and placed in a humidified incubator at 37° C. After about 18-24 hours, the medium was aspirated and fresh E8™ medium was added to the culture. The cells were cultured in the E8™ medium for about 2 days after seeding for proper adherence to the plate.

Example 2—Differentiation of iPSCs into RPE Cells

Once the single cell iPSCs seeded at the appropriate cells density were cultured for about 2 days as in Example 1, they were cultured in various differentiation media for deriving RPE cells. On day 3, the E8™ medium was aspirated and room temperature Retinal Induction Medium (RIM) (e.g., Table 3) was added. Briefly, the RIM comprised DMEM and F12 at about a 1:1 ratio, knockout serum replacement, MEM non-essential amino acids (NEAA), sodium pyruvate, N-2 supplement, B-27 supplement, and ascorbic acid. In addition, the RIM comprised a WNT pathway inhibitor, a BMP pathway inhibitor, a TGFβ pathway inhibitor and insulin growth factor 1 (IGF1). Each day the media was aspirated and fresh RIM was added to the cells. The cells were cultured in the RIM for about two to four days.

The cells were next cultured in Retinal Differentiation Medium (RDM) for about seven to fourteen days. Briefly, the RDM (Table 2) comprised DMEM and F12 at about a 1:1 ratio, knockout serum replacement, MEM NEAA, sodium pyruvate, N-2 supplement, B-27 supplement, and ascorbic acid. In addition, the RDM comprised a WNT pathway inhibitor (e.g., CKI-7), a BMP pathway inhibitor (e.g., LDN193189), a TGFβ pathway inhibitor (e.g., SB431542), and a MEK inhibitor (e.g., PD325901). The concentration of the Wnt pathway inhibitor, BMP pathway inhibitor and TGFβ pathway inhibitor was ten times higher in the RDM as compared to the RIM. Each day the media was aspirated and room temperature RDM was added to the cells to produce differentiated retinal cells.

To derive RPE cells, the cells were then cultured in Retinal Medium (RM) for seven to ten days. The RM comprised DMEM and F12 at about a 1:1 ratio, knockout serum replacement, MEM NEAA, sodium pyruvate, N-2 supplement, B-27 supplement and ascorbic acid. In addition, the RM comprised Nicotinamide and Activin A. The medium was changed daily with room temperature RM resulting in RPE cells.

For maturation of the RPE cells, the cells were cultured in RPE Maturation Medium (RPE-MM) for five to ten days. The RPE-MM (Table 2) comprised MEM Alpha, fetal bovine serum, N-2 supplement, MEM NEAA, and sodium pyruvate. In addition, the RPE-MM contained Taurine, Hydrocortisone and 3,3',5-Triiodo-L-thyronin (FIG. 1C). The medium was changed every other day with room temperature RPE-MM. The cells were then dissociated in a cell dissociation enzyme and reseeded on vitronectin coated plates. At this stage, the derived PRE cells can be cryopreserved in xenofree CS10 medium. To continue RPE maturation, plated cells are cultured for another approximately fifteen days.

Example 3—Maturation of RPE Cells

Figure 1D:
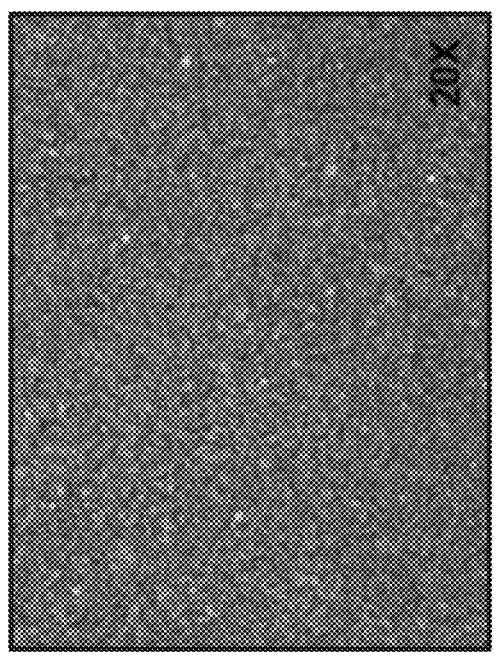
Figure 1D:
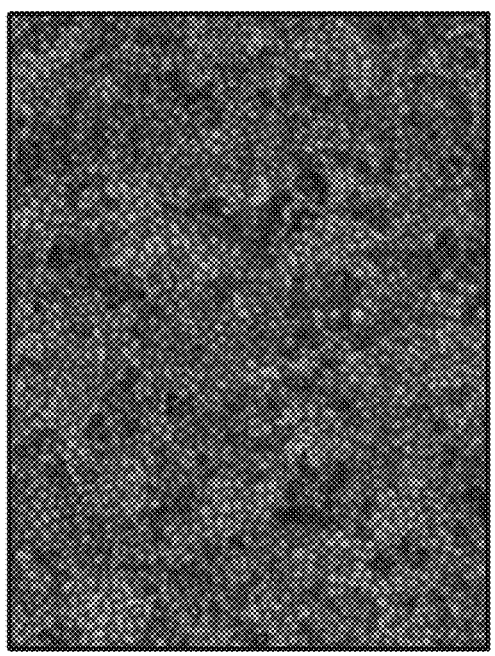

For continued maturation of the RPE cells produced in Example 2, the cells were dissociated in a cell dissociation enzyme such as TRYPLE™ and reseeded on a degradable scaffold assembly in a specialized SNAPWELL™ design for 1-2 weeks in the RPE-MM with a MEK inhibitor such as PD325901. This resulted in differentiated, polarized, and confluent monolayers of functional RPE cells (FIG. 1D) which can be cryopreserved at this stage in xenofree CS10 medium.

The mature RPE cells were further developed into functional RPE cell monolayers that function as an intact RPE tissue by continued culture in the RPE-MM with additional small molecules such as primary cilium inducers like PGE2 or aphidicolin. Without being bound by theory, these primary cilium inducers suppress the canonical WNT pathway, induce cell cycle exit in the cells, and induce apical-basal polarization in the RPE monolayer. RPE maturity can alternatively be induced by canonical WNT pathway inhibitors such as IWP2 and endo-IWR1 that also induce cell cycle exit in RPE cells to promote RPE maturation. The cells were cultured in this medium for another 2-3 weeks to obtain mature and functional RPE cell monolayers. Thus, the presently disclosed methods provide mature RPE cells from pluripotent cells that can be consistently reproduced at a large scale for clinical applications.

Example 4—Cryopreservation of RPE Cells

For the cryopreservation of the differentiated RPE cells of Example 2, the medium was aspirated and the cells were washed twice with Dulbecco's Phosphate-Buffered Saline (DPBS). The cells were then incubated with a cell dissociation enzyme and the cell suspension was pipetted into a conical tube. The cells were centrifuged, the supernatant aspirated and the cells resuspended in room temperature RPE-MM. The cell suspension was then filtered through a STERIFLIP® cell strainer and the cells were counted. Next, the cells were centrifuged and resuspended at an appropriate density (e.g. $1 \times 10^7$ cells/mL) in cold CryoStor® CS10. The cell suspension was aliquoted into pre-labeled cryovials which were placed in a cold freezing container and transferred to a −80° C. freezer for 12-24 hours. The vials were then transferred to liquid nitrogen for storage.

Example 5—MACS Depletion of Contaminating Non-RPE Cells and Enrichment of Starting Population of RPE Cells by CD24, CD56, and/or CD90 Depletion The population of RPE cells obtained in Example 2 or 3 can have residual contaminating non-RPE cells as well as immature RPE cells (collectively referred to as the "contaminating cells"), both of which can be separated and removed to yield a mature RPE-enriched cell population. The contaminating cells can be removed from the culture by various methodologies, such as, for example, Magnetic Activated Cell Sorting (MACS®), Fluorescent Activated Cell Sorting (FACS), or single cell sorting. The MACS® methodology, which is known in the art to separate various cell populations depending on their surface antigens, was used to separate the contaminating cells from the desired, more mature RPE cells.

The contaminating cells of the starting population of RPE cells have specific cell surface markers which can be used to separate contaminating cells from the desired mature RPE cells. For example, CD24, CD56, and/or CD90 are cell surface antigens expressed on (but not limited to) pluripotent stem cells and other neural cell types. CD24 is a glycoprotein expressed on the surface of pluripotent stem cells, some B lymphocytes and differentiating neuroblasts. CD56 or neural cell adhesion molecule (NCAM) is a glycoprotein expressed on the surface of neurons and natural killer cells. CD90 or Thy-1 is a marker expressed on the surface of a variety of stem cells as well as neurons. The expression of CD24, CD56 and/or CD90 is lost during differentiation of stem cells to many mature cell types including RPE cells. Therefore, removal of cells positive for CD24, CD56, and/or CD90 results in the depletion of the residual contaminating cells.

In order to carry out a separation technique, it is desirable to dissociate the starting population of RPE cells into a single cell suspension for sorting (e.g., MACS) to be performed. For cells that were previously cryopreserved, cells must be thawed and replated. To obtain a single cell suspension from cells in adherent culture, the cells were washed (e.g., DPBS) and a cell dissociation enzyme was added (e.g., TRYPLE™). After the cells were incubated at 37° C. for about 5 min, the vessel was tapped gently to detach the neuronal clusters. The cells were washed twice in DPBS and a cell dissociation enzyme was added (e.g., TRYPLE™). After the cells were incubated at 37° C. for about 30 min, the cell suspension was collected in RPE-MM Plating Medium and centrifuged at 400×g for 5 min. The cell pellet was resuspended in RPE-MM Plating Medium and the cell suspension was filtered through a cell strainer (e.g., 20 μM steriflip cell strainer) to dissociate any remaining cell clusters. The cell suspension was counted (e.g., using a ViCell counter) for viable cells to obtain a cell concentration. The counted cell suspension provided a single cell suspension that could be used for sorting or the flow cytometry purity assay.

To remove the contaminating cells from the starting population of RPE cells, MACS was used to deplete the CD24 positive cells, the CD56 positive cells, and/or the CD90 positive cells. After the cells from the starting population of RPE cells were dissociated into a single cell suspension, the cells were resuspended in MACS buffer such as at $1 \times 10^7$ cells/mL. An example MACS buffer is included in Table 3. Next, the cells were stained with an anti-CD24 antibody, an anti-CD56 antibody, and/or an anti-CD90 antibody (each diluted 1:500) and incubated at 4° C. for 20 min to allow the antibody to bind to the antigen on the cells. The antibodies used should be tagged with a label (e.g., FITC) that will bind to the secondary antibody. After incubation, 20 mL of MACS buffer was added and the cells were centrifuged at 400×g for 5 min. The cell pellet was resuspended in 20 mL MACS buffer, vigorously mixed, and centrifuged at 400×g for 5 min to remove any unbound antibody. The cell pellet was resuspended in MACS buffer (e.g., at $1.11 \times 10^8$ cells/mL), microbeads coated with the diluted (1:10) secondary antibody (e.g., anti-FITC) were added, and the cells were incubated at 4° C. for 20 min. After incubation, the cells were washed with MACS buffer to remove unbound microbeads and up to $1.25 \times 10^8$ cells were resuspended in 500 μL MACS buffer. The cell suspension was transferred to a LD column placed in a strong magnetic field and the cells expressing the antigen CD24, CD56, and/or CD90 attached to the microbeads remained in the column. The LD column was washed two times with MACS buffer. The unlabeled cells not expressing the antigens CD24, CD56, and/or CD90 were allowed to flow through and were collected. For further characterization and culture, the collected unlabeled cell suspension was centrifuged (400×g for 5 min) and replated in RPE-MM Plating Medium, and an aliquot of the cell suspension was used for the flow cytometry purity assay. Thus, the MACS cell sorting resulted in a RPE-enriched cell population depleted of cells positive for CD24, CD56, and/or CD90. It is noted that the use of this method is not limited to the starting population resulting from the method detailed in Example 2 and may be employed to remove contaminating cells from a RPE population produced by other methods such as, but not limited to, the methods described in U.S. application Ser. Nos. 12/523,444, and 14/405,730.

TABLE 1

MACS Cell Sorting Summary

| Marker | Pre-sort (%) | CD24 (%) | CD24/ CD56 (%) | CD24/ CD90 (%) | CD24/ CD56/ CD90 (%) |
|---|---|---|---|---|---|
| MITF+ | 94.5 | 99.1 | 99.2 | 99.1 | 99.5 |
| MAP2+/NES− | 0.4 | 0.2 | 0.1 | 0.1 | 0.2 |
| PMEL17 | 95.5 | 99.5 | 99.7 | 99.5 | 99.8 |

TABLE 1-continued

MACS Cell Sorting Summary

| Marker | Pre-sort (%) | CD24 (%) | CD24/ CD56 (%) | CD24/ CD90 (%) | CD24/ CD56/ CD90 (%) |
|---|---|---|---|---|---|
| TYRP1 | 95.9 | 99.4 | 99.8 | 99.6 | 99.8 |
| CRALBP | 89.3 | 98.2 | 99.4 | 98.8 | 99.8 |
| BEST1 | 78.6 | 95.0 | 98.6 | 95.9 | 99.0 |

The pre-sorting percentages of cells positive for the RPE-markers are those present in the starting population of RPE cells of Example 2. Depletion of the combination of CD24 positive cells and CD56 positive cells resulted in greater enrichment of RPE cells than the depletion of only CD24 positive cells. Depletion of CD24 positive cells, CD56 positive cells and CD90 positive cells resulted in more than 99% RPE cells in the cell population.

Figure 2B:
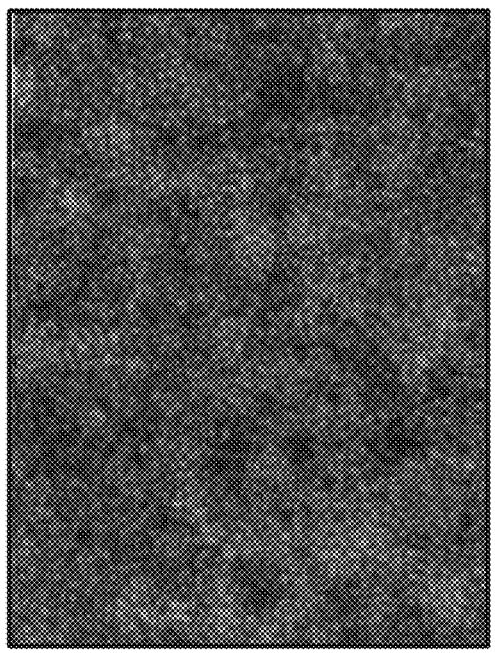
FIGS. 2A-2B: Flow-cytometry analysis of relevant markers including MAP2, NES, PAX6, MITF, PMEL17, TYRP1, CRALBP and BEST1 before cell sorting of iPSC-derived RPE cell population.
Figure 2A:
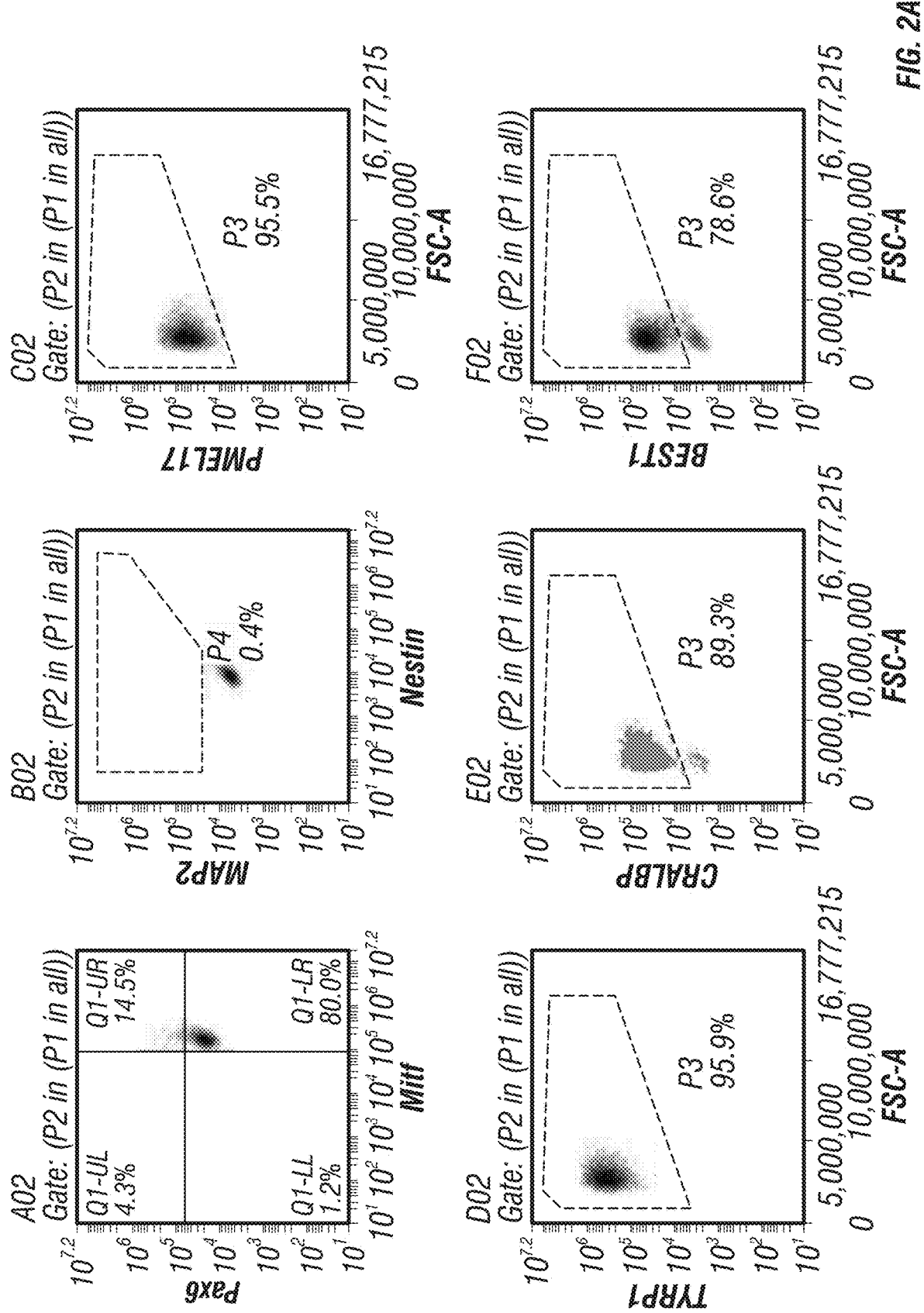
Figure 3A:
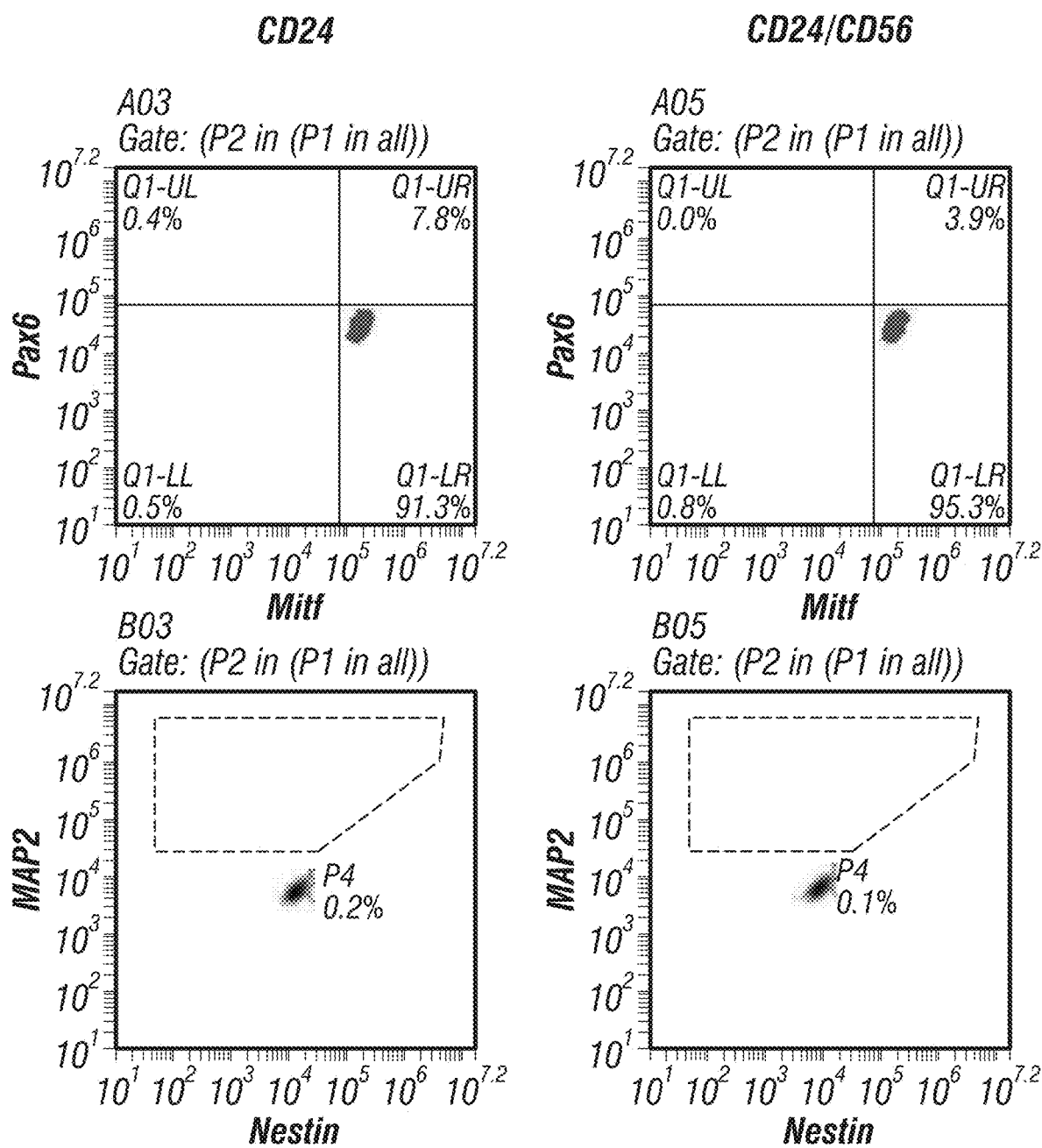
FIGS. 3A-3C: Flow-cytometry analysis of relevant markers including MAP2, NES, PAX6, MITF, PMEL17, TYRP1, CRALBP and BEST1 after cell sorting of an iPSC-derived RPE cell population to remove CD24 positive cells, CD24 positive and CD56 positive cells, CD24 positive and CD90 positive cells, and CD24 positive, CD56 positive, and CD90 positive cells.
Figure 3A:
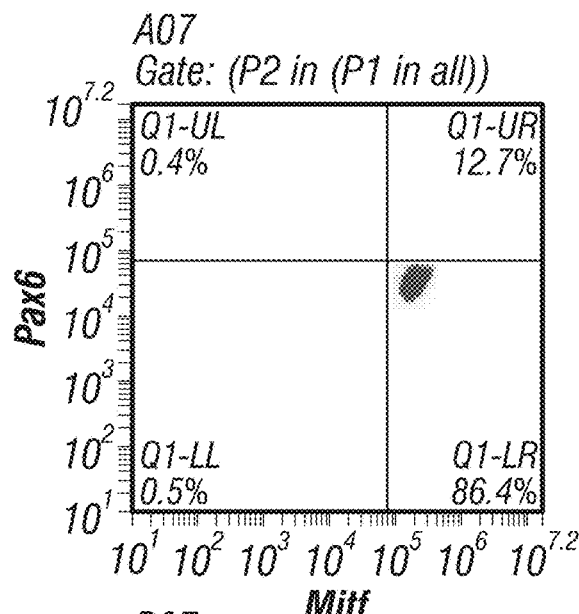
Figure 3A:
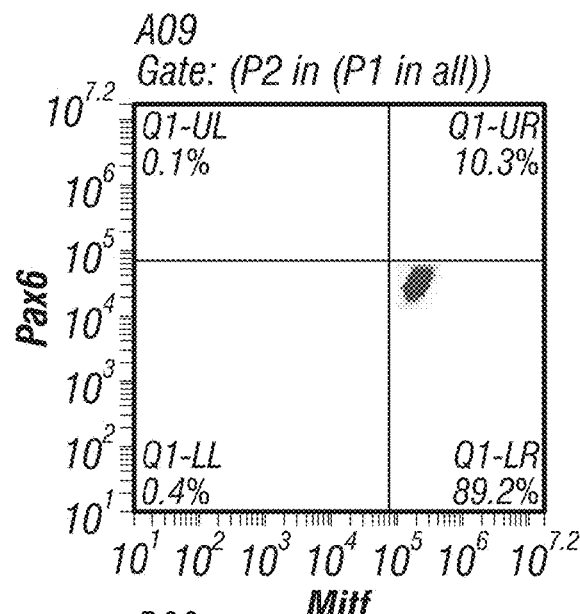
Figure 3A:
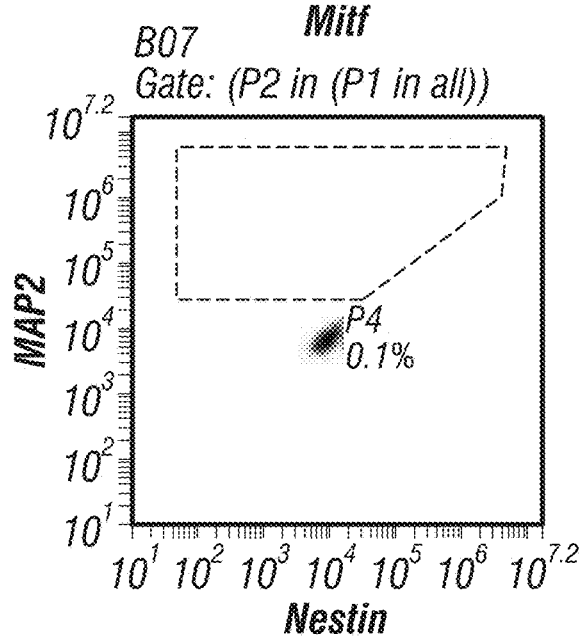
Figure 3A:
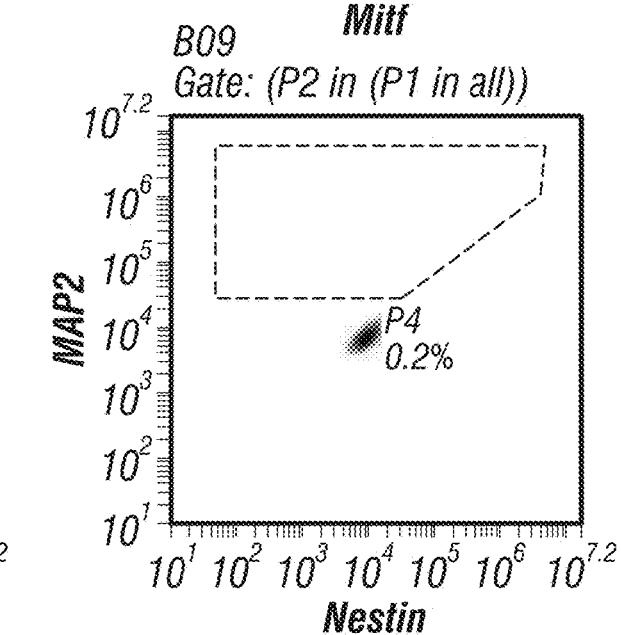
Figure 3B:
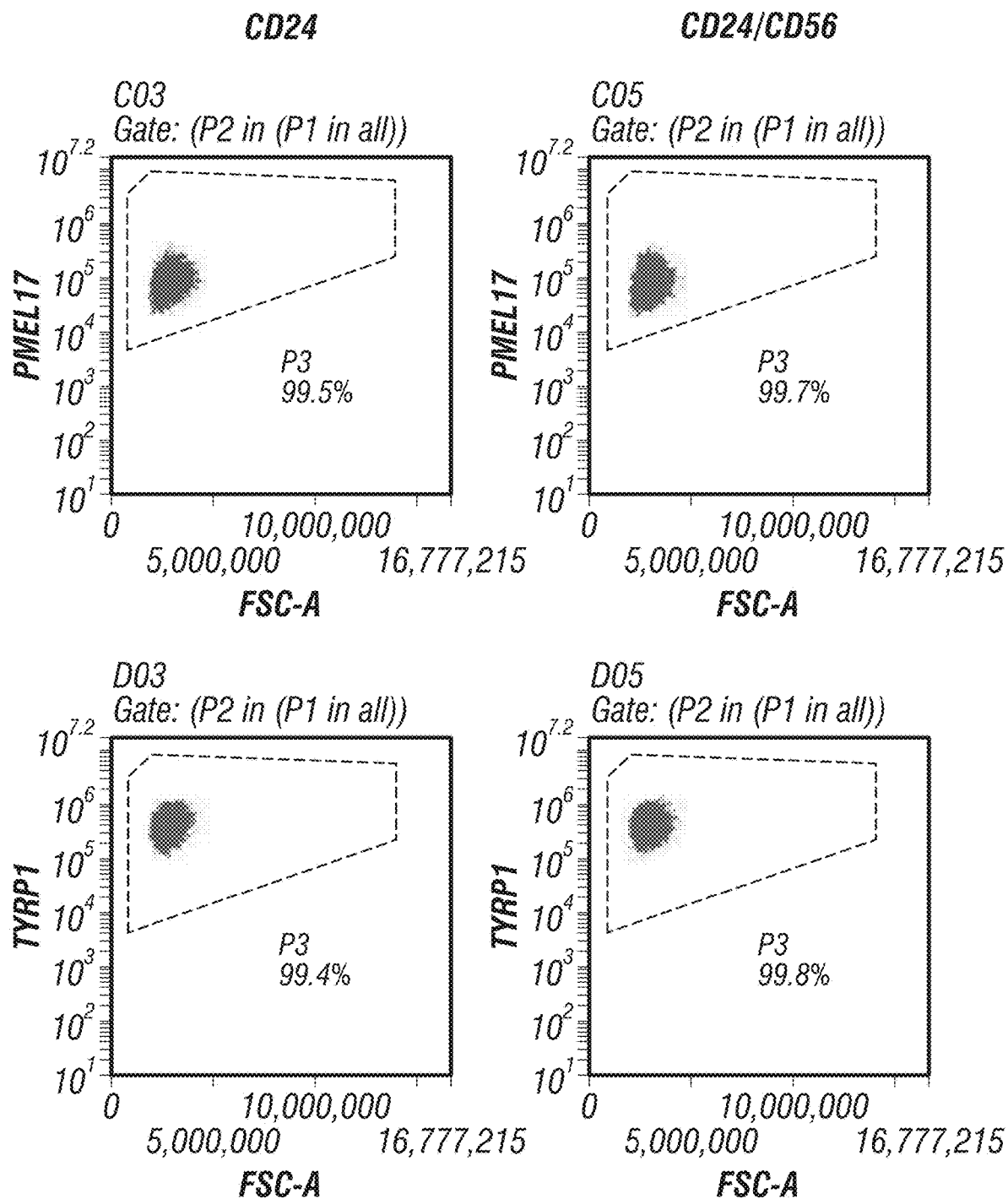
Figure 3B:
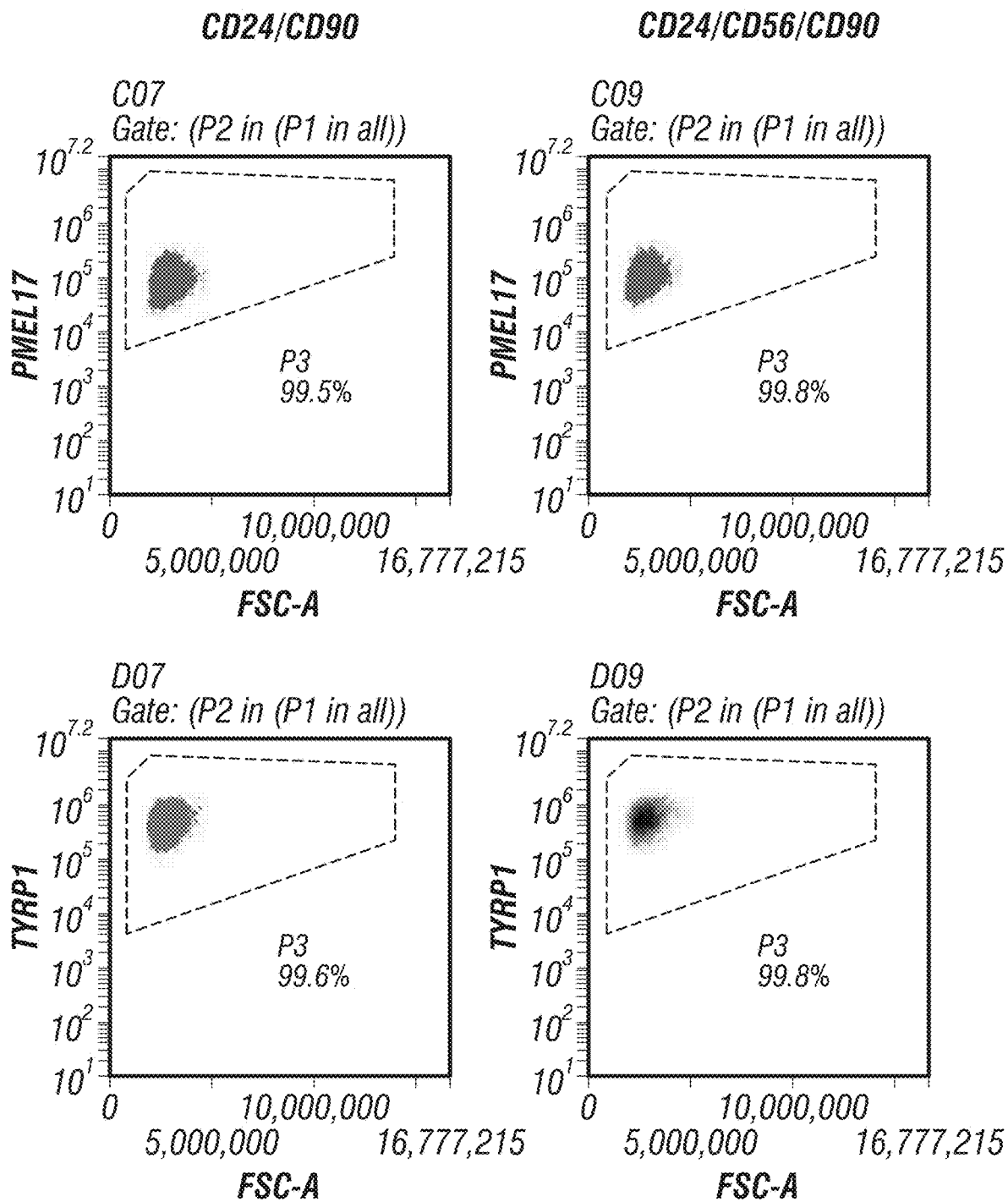
Figure 3C:
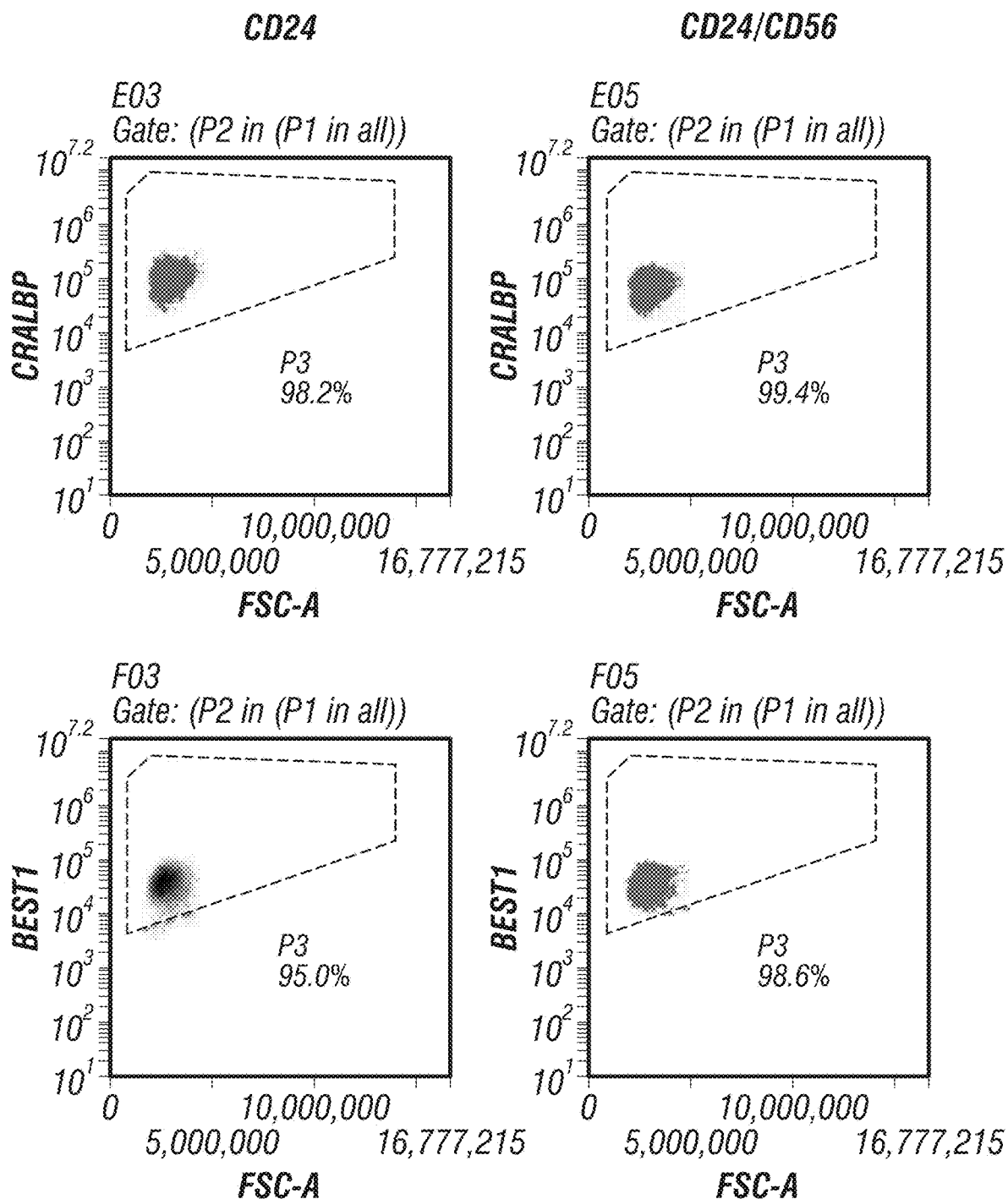
Figure 3C:
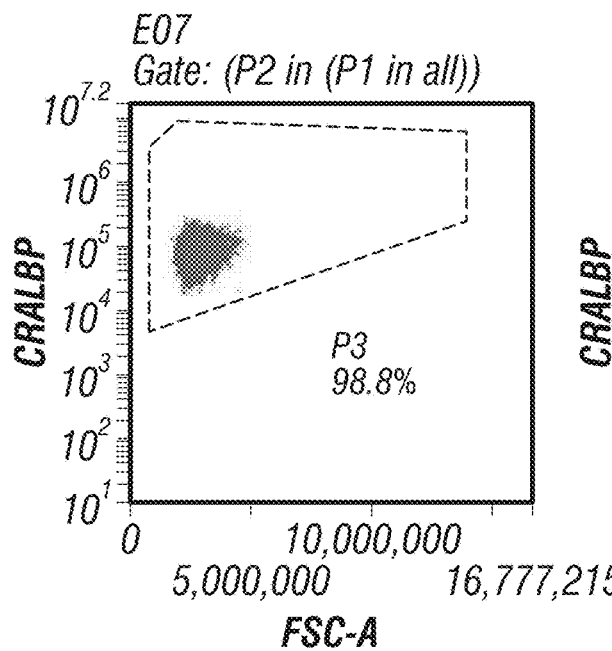
Figure 3C:
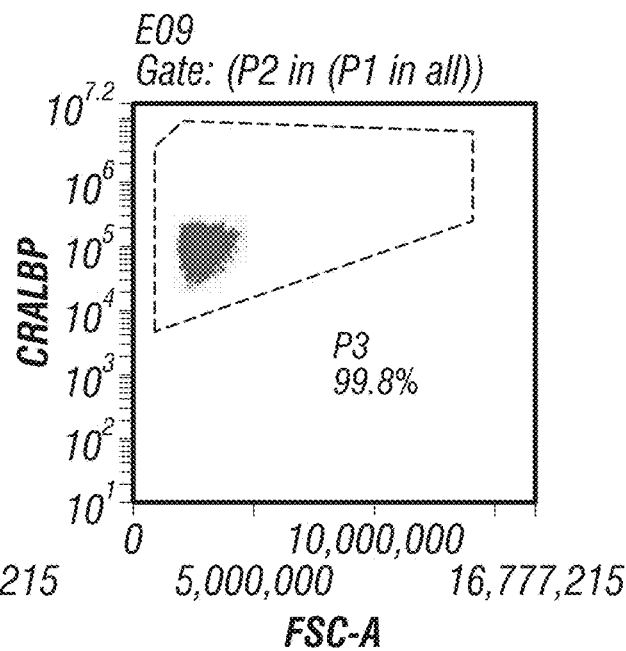
Figure 3C:
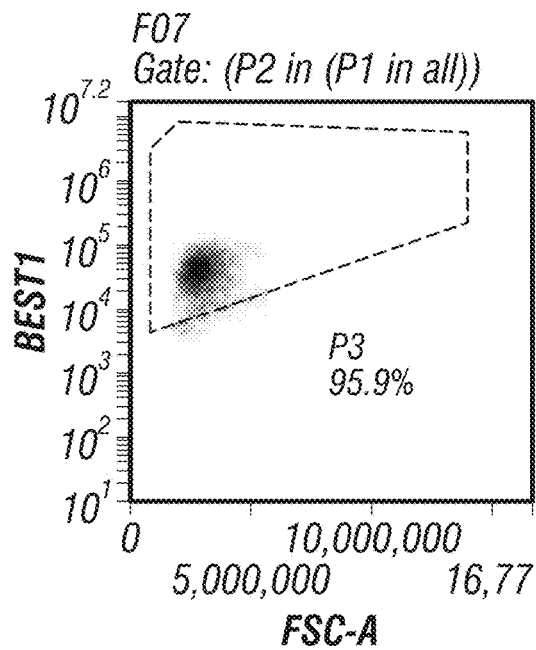
Figure 3C:
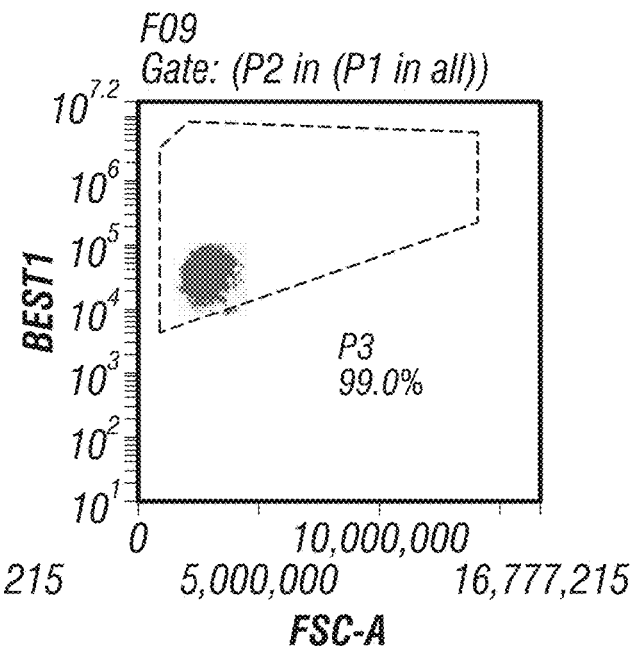

Example 6—Flow Cytometry Purity Assay for the Characterization of the RPE-Enriched Cell Population Before and after MACS sorting was performed, characterization of the RPE cells by a panel of relevant markers including BEST1, CRALBP, TYRP1, PMEL17, MAP2, NES, and MITF was performed (e.g. pre-sorting and post-sorting). The flow cytometry purity assay was performed to obtain a measurement of the percentages (Table 1) of cells positive for each marker before and after removal of CD24 positive cells, CD56 positive cells, and/or CD90 positive cells by MACS (FIGS. 2 and 3).

The flow cytometry purity assay was performed to determine the percentage of RPE cells obtained by a sorting method of the present disclosure. An aliquot of the cell suspension collected from the MACS assay (2×10$^6$ cells in a 5 mL FACS tube per sample) was centrifuged at 400×g for 3 min. The cell pellet was resuspended in 1 mL of a stain (e.g., Live-Dead Red stain) and incubated in the dark at room temperature for 15 min. After incubation, 2 mL of wash buffer was added and the cells were centrifuged at 400×g for 3 min to remove any unbound stain. The cell pellet was resuspended in fixation buffer and incubated in the dark at room temperature for 15 min. After incubation, 2 mL of wash buffer were added and the cells were centrifuged at 400×g for 3 min and the supernatant was decanted. The cell pellet was resuspended in 2 mL of wash buffer to make a 1×10$^6$ cells/mL suspension and 200 µL of the cell suspension was transferred to a FACS tube. To each tube, 2 mL of perm buffer was added and cells were centrifuged at 400×g for 3 min. Primary antibodies for the RPE-specific markers were diluted in perm buffer and 100 µL diluted antibody solution was added to each tube. After incubation overnight at 4° C. in the dark, the cells were washed in 2 mL Penn Buffer two times. Secondary antibody solution was added to each of the tubes and cells were incubated at room temperature in the dark for 1-2 hours. After incubation, the cells were washed twice with Penn Buffer, centrifuged (400×g for 3 min) and resuspended in 100 µL wash buffer for flow cytometry analysis. Flow cytometry analysis was performed by methods known to those in the art, such as in U.S. Pat. No. 8,682,810 and Herzenberg et al., 2006, incorporated herein by reference, to obtain percentages of cells positive for each of the markers tested (Table 1). The flow cytometry purity assay showed that the MACS sorting to deplete the contaminating cells positive for CD24, CD56, and/or CD90 resulted in a RPE cell-enriched population (95-99%) as compared to the starting cell population (78.6%) as determined by the BEST1 marker.

Example 7—Alternate Method for Differentiation of RPE Cells

With regard to the methods described in Examples 2 and 3, the inclusion of PD0325901 at a concentration of 1 µM in media for certain windows of time beginning on Day 2 post iPSC plating through the end of the differentiation process, including post-MACS culture, may improve both purity of the RPE population (meaning a decrease in contaminating cells) as well as maturity of the resulting RPE population. Inclusion of 1 µM PD 0325901 has been shown to improve both purity and maturity of the RPE population when included in RDM as well as in RPE-MM (approximately Days 42 through 50) of the RPE process described herein.

Example 8—Alternate Method for Differentiation of RPE Cells

With regard to the methods described in Examples 2 and 3, a decrease in the percentage of fetal bovine serum from 5 percent to 0.5-1 percent in RPE-MM and RPE-MM Plating Medium may improve both purity of the RPE population (meaning a decrease in contaminating cells) as well as maturity of the resulting RPE population.

Example 9—Functionality of Mature RPE Cells

Figure 4C:
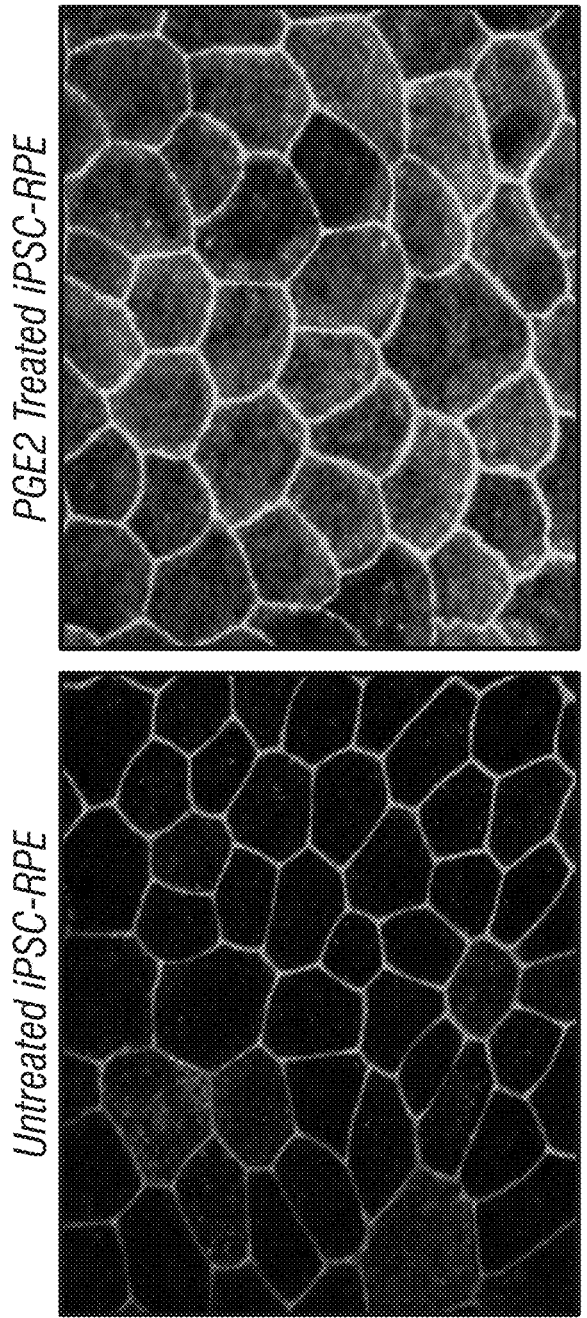
Figure 5D:
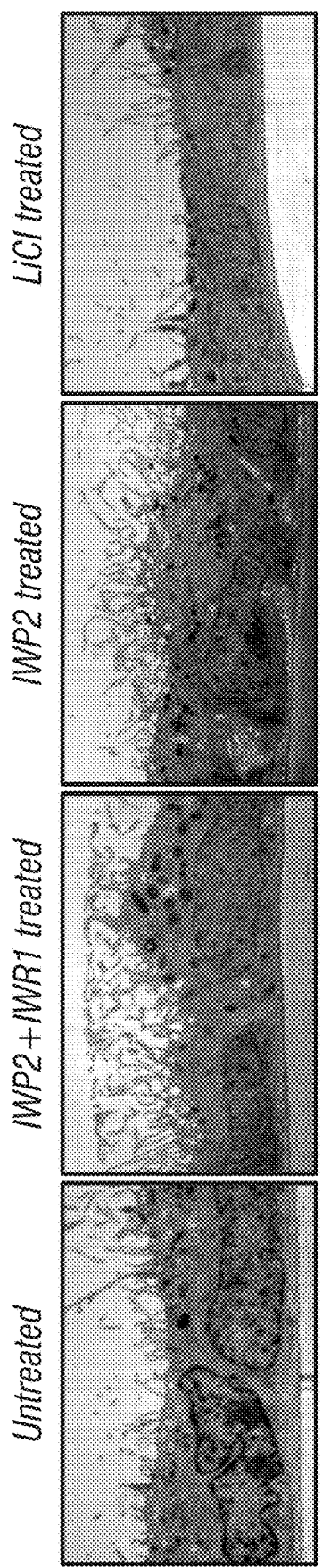

For analysis of the mature RPE cells produced from treatment with PGE2, immunostaining of the RPE monolayer was performed to confirm the hexagonal architecture (FIGS. 4A-4C) of tight junctions by ZO1 staining as well as transmission electron microscopy of the iPSC-RPE cells (FIG. 4D). The staining showed that PGE2 treated RPE cells have decreased beta catenin and increased RPE65. In addition, treatment with IWP2+endo-IWR1 or IWP2 results also results in decreased beta catenin (FIG. 5A) and increased RPE65 (FIG. 5C). The combination of IWP2+endo-IWR1 was found to be more effective as compared to IWP2 alone or endo-IWR1 alone. Thus, treatment with PGE2, IWP2, or IWP2+endo-IWR1 produces mature RPE cells.

Figure 7A:
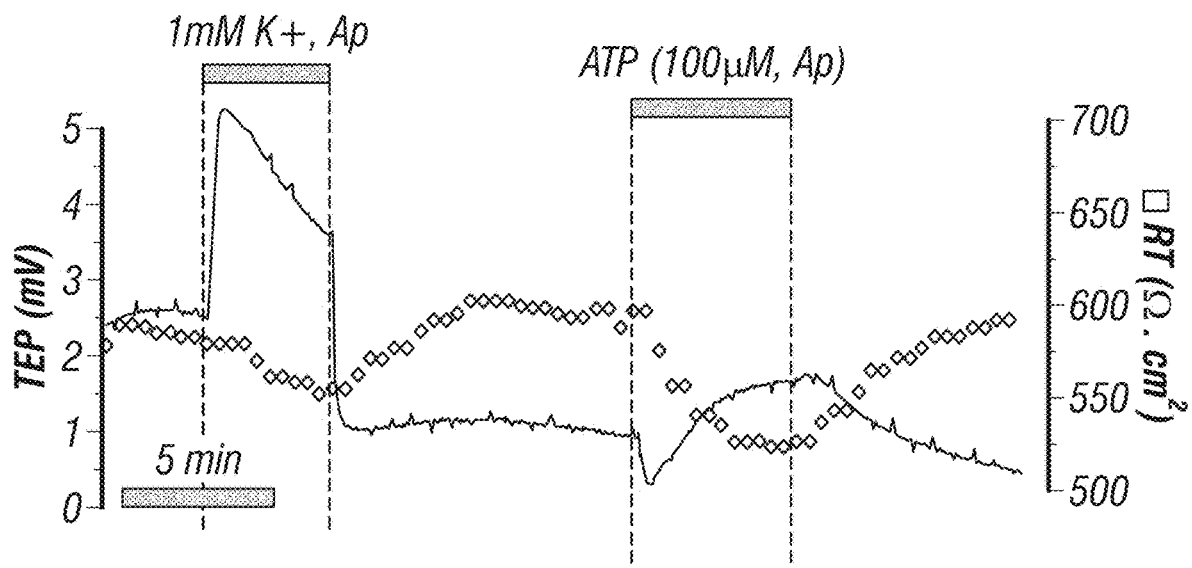
FIGS. 7A-7G: A) Functionality of the barrier function of RPE cells generated using the RPE differentiation protocol is shown by transepithelial electric potential (TEP) measurement of the ion gradient across the monolayer. B) Functionality of RPE cells treated with IWP2 or IWP2+endo-IWR2. C-E) Transepithelial electric resistance (TER) and TEP (lighter line) of untreated cells, PGE2 treated cells and IWP2+endo-IWR1 treated cells. F) Functional response (TER) from cells matured with 50 µM vs. 100 µM PGE2 in the RPE-MM+PGE2 medium from Day 54 to Day 75 of iPSC-derived differentiation protocol. There was a progressive increase in the measure of the TER during the course of their differentiation with 100 µM as compared to the iPSC-derived RPE cultured using 50 µM PGE2 in RPE-MM+ PGE2 medium from day 54 to day 75 of the differentiation protocol. This demonstrates that an increase in the concentration of PGE2 promotes the maturity and functional efficiency of the iPSC-derived RPE cultures. G) iPSC-derived RPE purity by percent expression of mature RPE markers at day 75 in cultures with 50 µM vs 100 µM PGE2 started at day 54 to day 75 of iPSC-derived RPE differentiation protocol. There is comparable expression of Pmel17, Tryp1 and Cralbp (RPE-specific markers) to the iPSC-derived RPE cultured using 50 µM PGE2. This shows that PGE2 promotes iPSC-derived RPE differentiation over a range of concentrations. The expression of Best 1 marker (late maturity RPE marker) is much higher in the cells treated with 100 µM PGE2 as compared to the cells treated with 50 µM PGE2 showing that increasing the concentration of PGE2 enhances the purity and maturity of the iPSC-derived RPE.
Figure 7B:
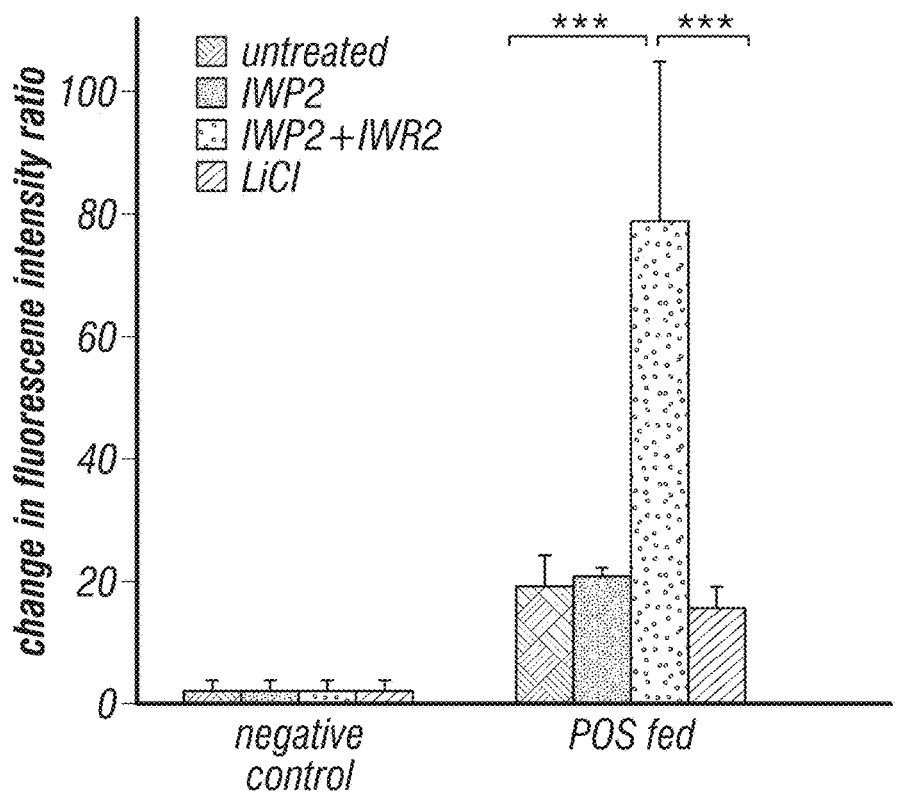

To measure the barrier function of the RPE cells generated by the present methods, transepithelial electrical potential (TEP) was measured the ion gradient across the monolayer generated by energy-driven ion pumps that regulate passage across the cells, and transepithelial electrical resistance (TER) measures resistance of substances through the paracellular space mainly through the fine structure of the tight junction structure (FIG. 7A).

Figure 7C:
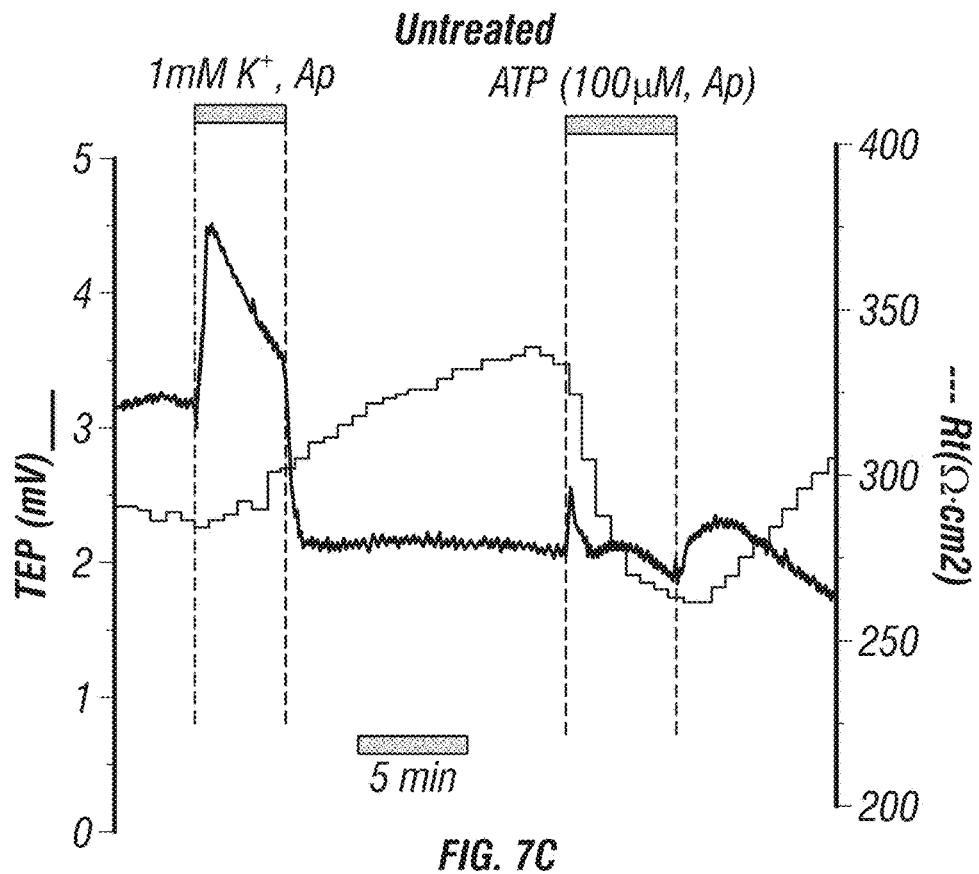
Figure 7D:
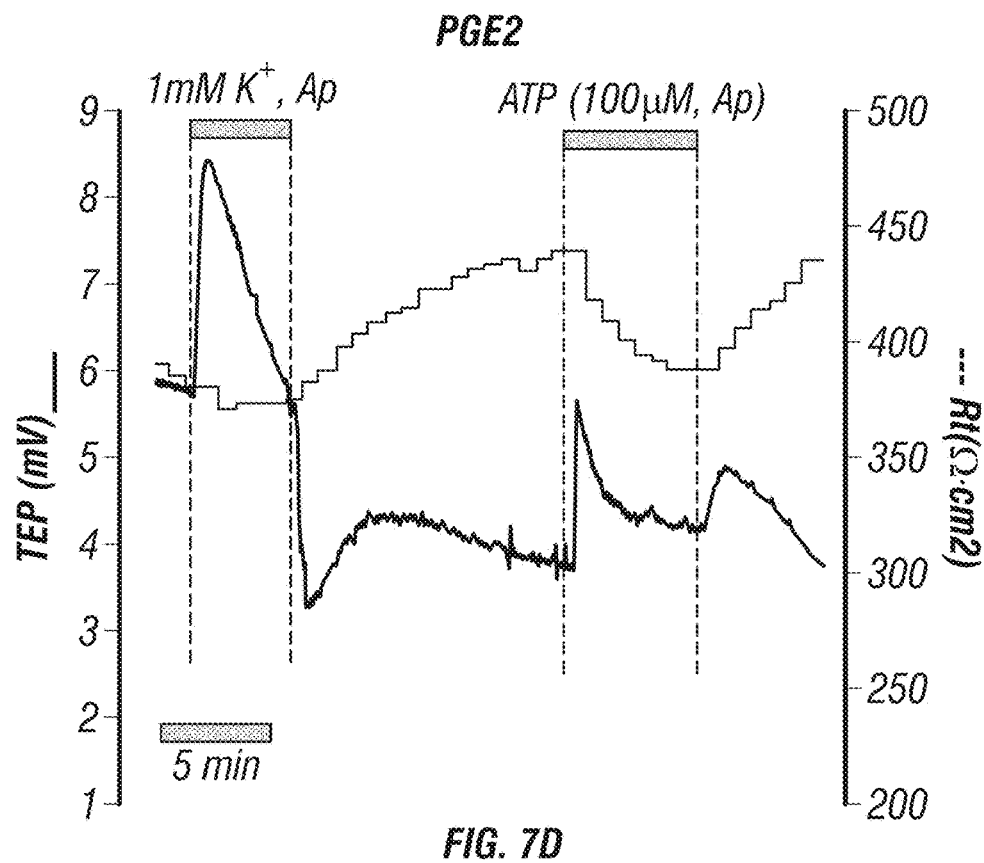
Figure 7E:
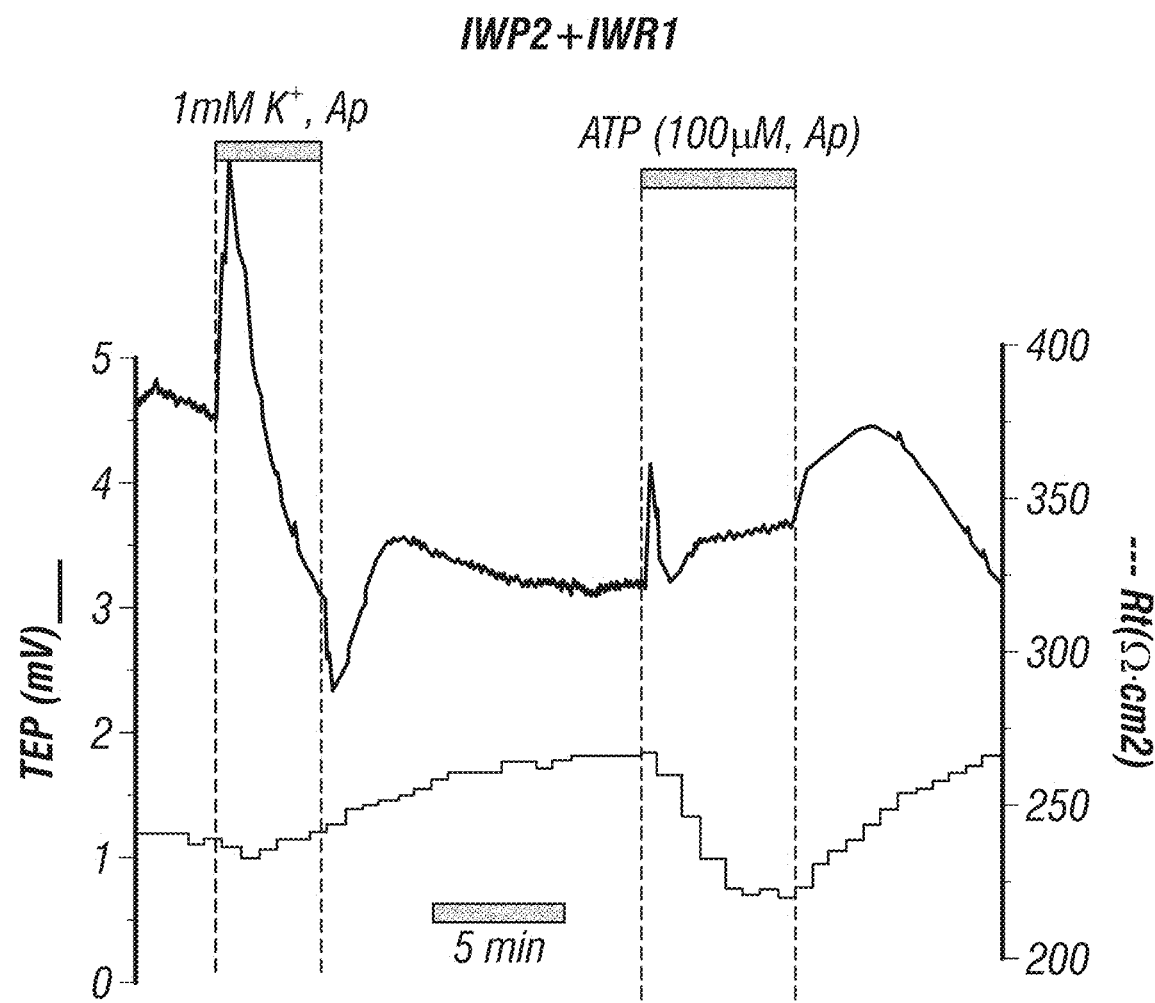

Functionality of the mature RPE cells treated with IWP2 or endo-IWR1 was also characterized. TEP and TER measurements of untreated RPE cells versus RPE cells treated with PGE2 or IWP2+endo-IWR1 show increased functionality of the treated, mature RPE cells (FIGS. 7C-7E).

Figure 7F:
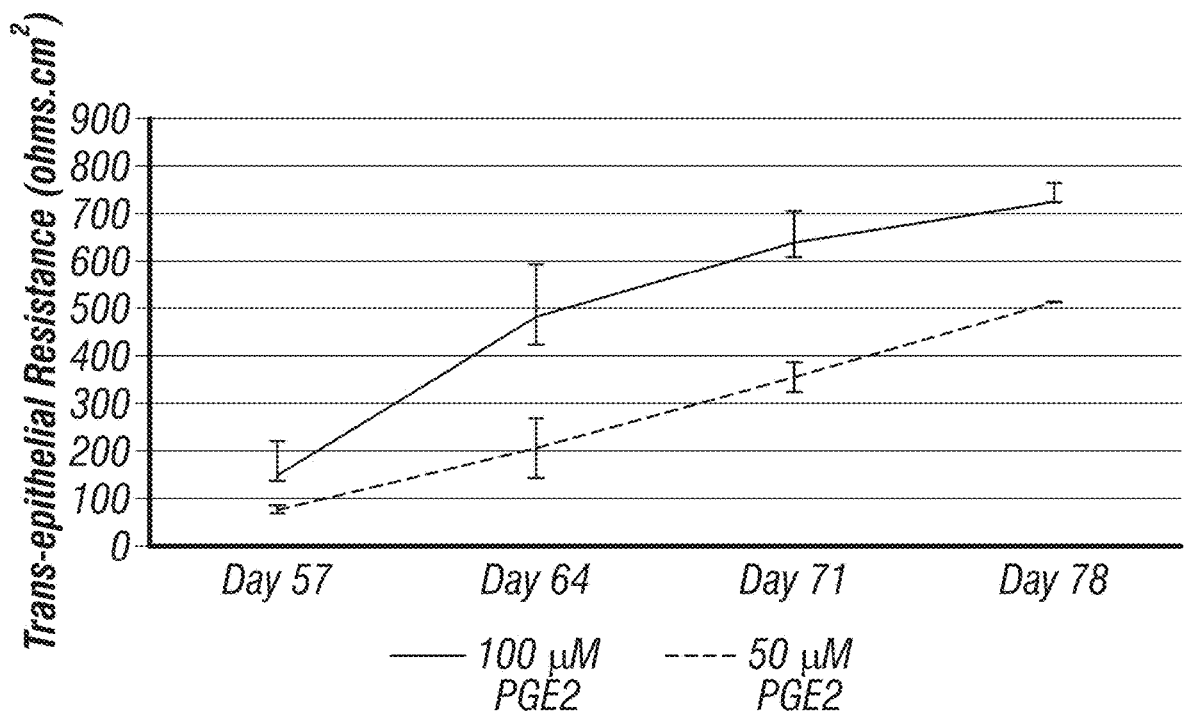
Figure 7G:
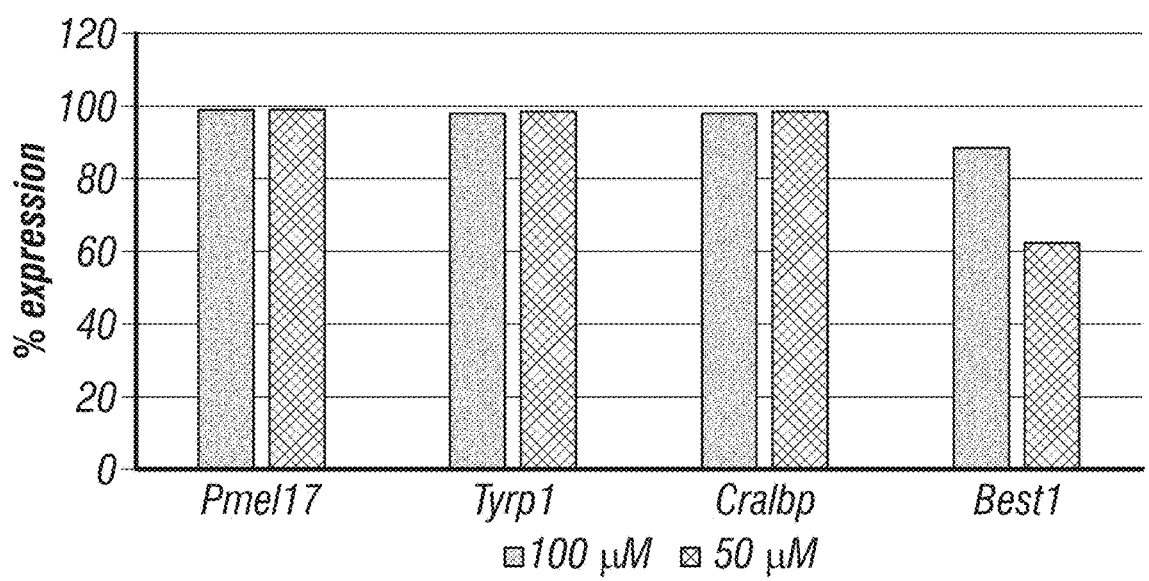

Next, it was tested whether an increase in the concentration of PGE2 from 50 µM to 100 µM in the RPE-MM+PGE2 medium would improve both purity of the RPE population (i.e., a decrease in contaminating cells) as well as maturity of the resulting RPE population. To determine the maturity and functionality of the 50 µM versus 100 µM PGE2 treated cultures, the barrier function in terms of transepithelial electrical resistance (TER) was measured (FIG. 7F) to compare the resistance of substances through the paracellular space as explained in Example 9. To determine the percentage of pure RPE cells obtained after treatment of the iPSC-derived RPE cultures with 50 µM or 100 µM in the RPE-MM+PGE2 medium, flow cytometry purity assay was performed for RPE-specific markers (FIG. 7G) as described in Example 6. The results showed that a higher concentration of the primary cilium inducer PGE2 promotes both the purity and maturity of the RPE population in the process of iPSC-derived RPE differentiation.

Example 10—Reproducibility of RPE Differentiation Method

Figure 6A:
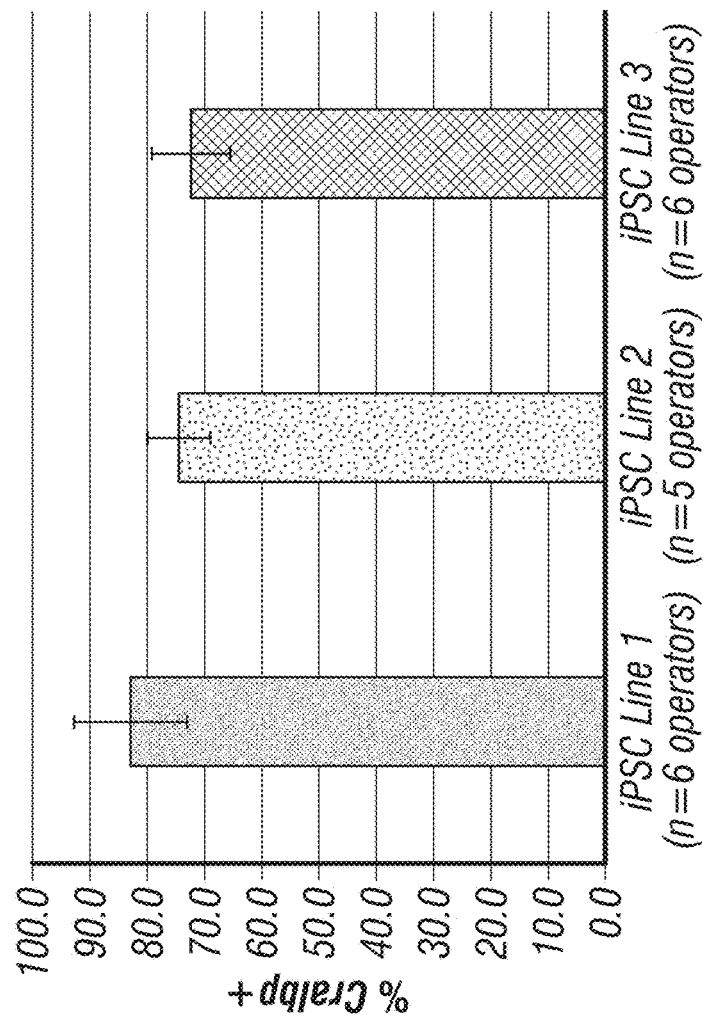
FIGS. 6A-6D: A) Multi-operator RPE Differentiation. Data shown represent RPE differentiations set-up using the optimized protocol across three lines with multiple operators as measured by flow cytometry for the RPE marker Retinaldehyde-binding protein 1 (Cralbp). B) Reproducibility of the RPE differentiation protocol is shown among different starting cell line populations including 3D1, AMD1B, BEST1L, BEST3A, BEST8A, AMD Donor3D, AMD Donor3C and HLA Line A. C-D) Reproducibility of the RPE differentiation protocol is shown among different starting cell line populations. Data represent 109 differentiations performed by five operators on 28 iPSC lines derived from 13 donors. The percentage of Cralbp-positive cells increased to between 90-100% as compared to the varied purity of the pre-purification cell population.
Figure 6B:
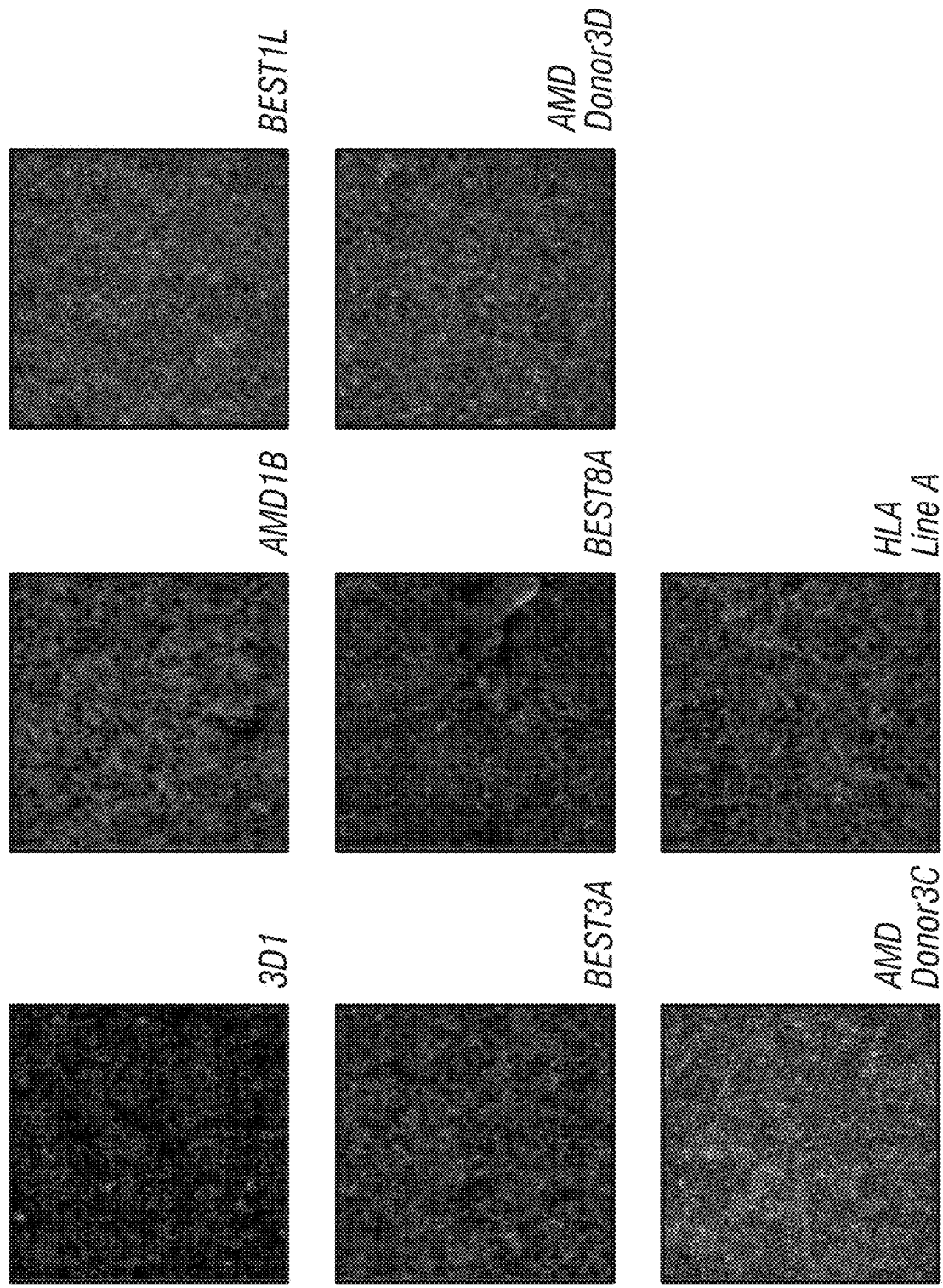
Figure 6C:
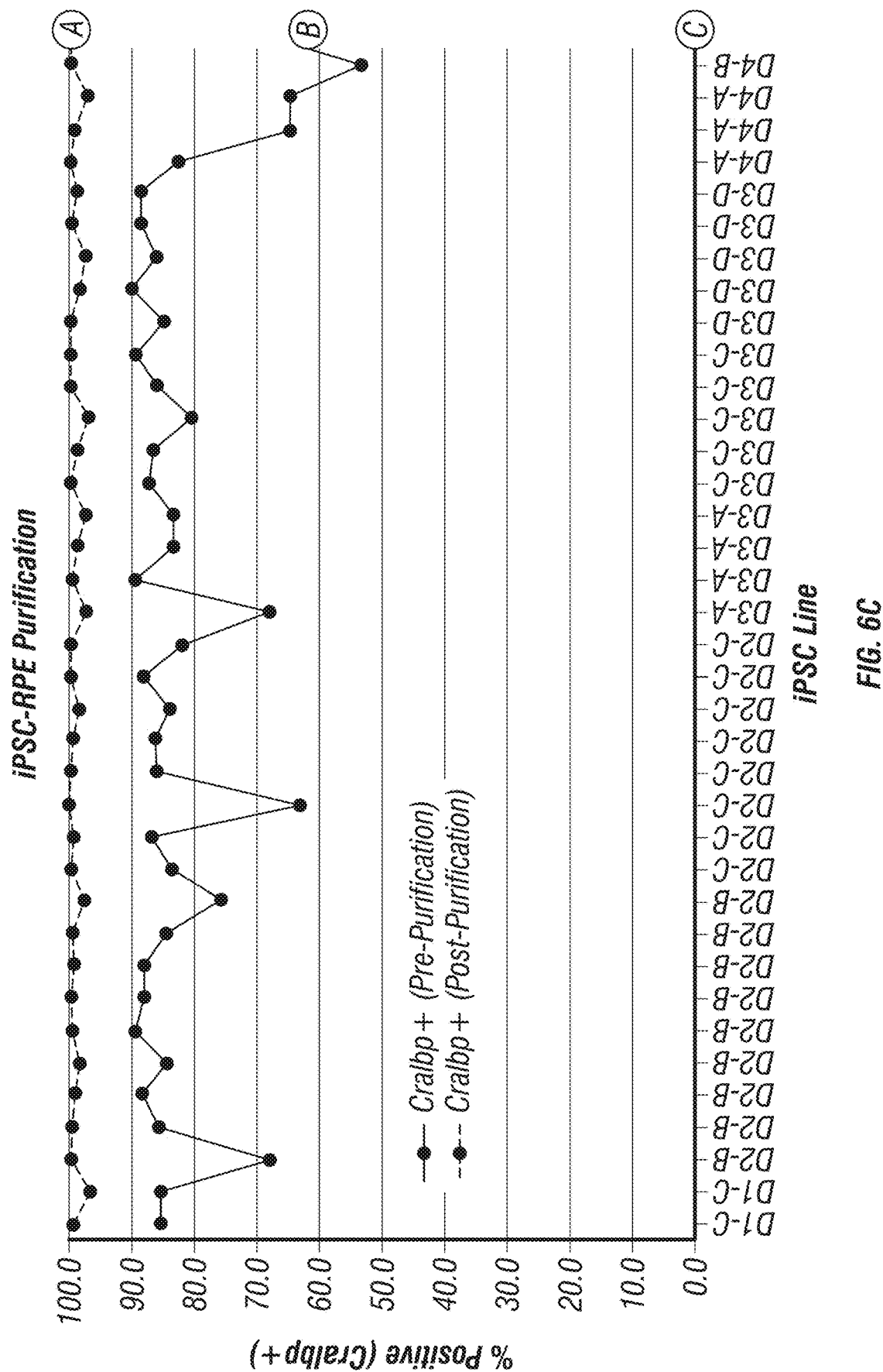
Figure 6C:
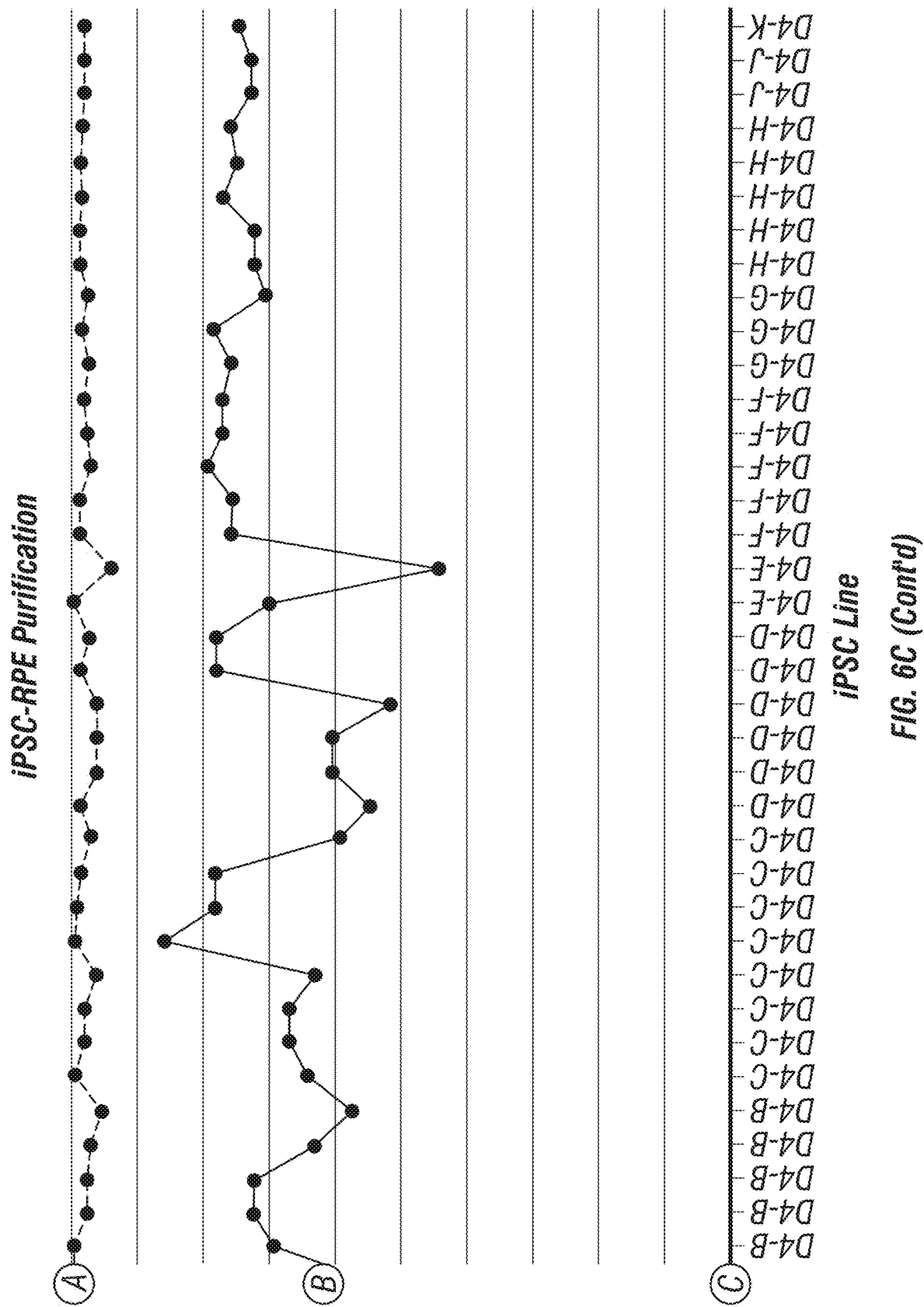
Figure 6D:
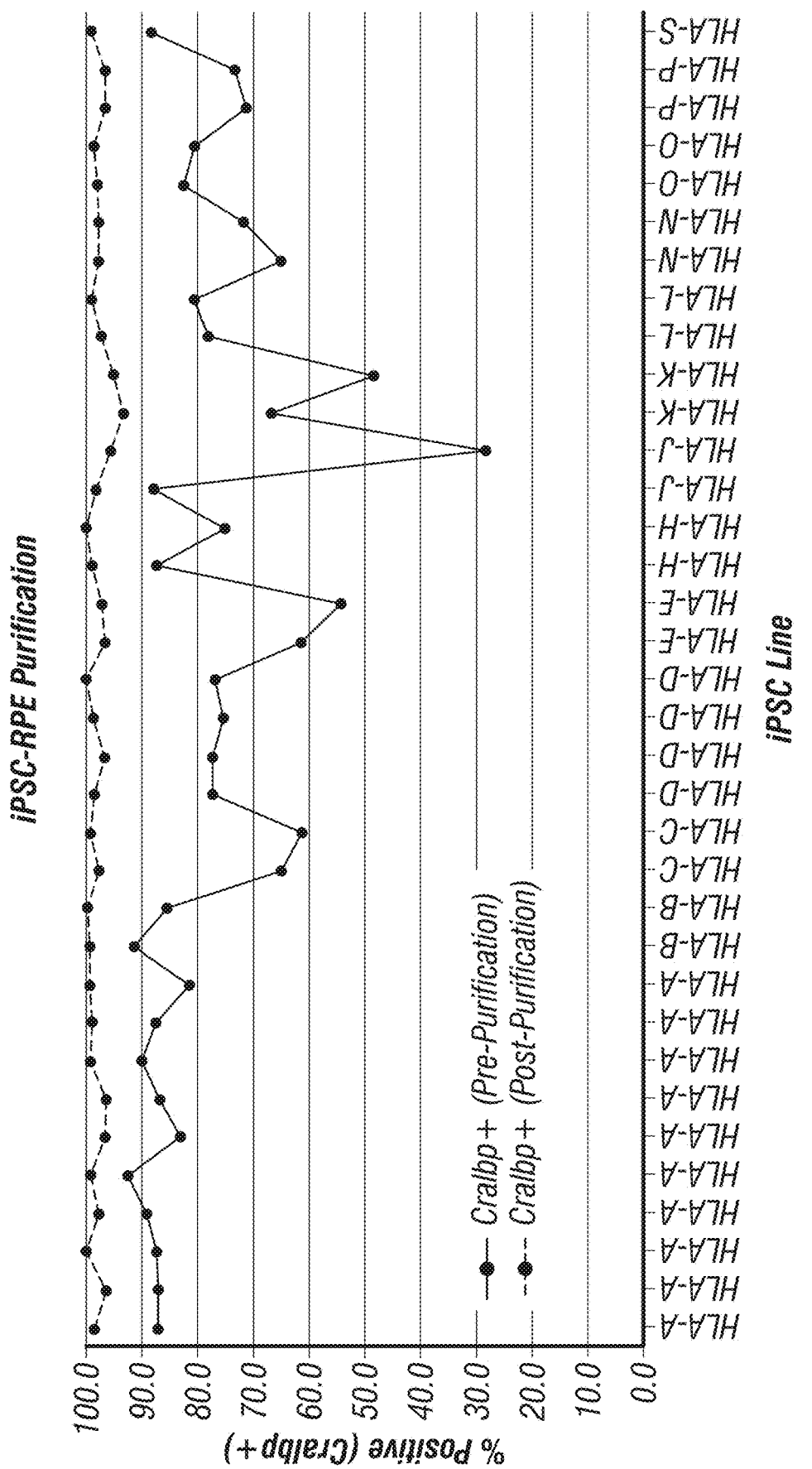

To test the reproducibility of the RPE differentiation process, three iPSC lines were differentiated to RPE cells by multiple operators (FIG. 6A). The average purity of the resultant RPE cells was characterized by measurement of the RPE marker Retinaldehyde-binding protein 1 (Cralbp) by flow cytometry (Table 2). The RPE differentiation process was found to be highly reproducible between different starting cell populations as well as different operators. In addition, the reproducibility was confirmed by RPE differentiation from different starting cell lines including 3D1, AMD1B, BEST1L, BEST3A, BEST8A, AMD Donor3D and HLA Line A (FIG. 6B). HLA Line A (21525.102) is an iPSC line produced from a donor homozygous for HLA-A*01 and HLA-B*08 that could provide a beneficial match to 11.38% of the US population. Furthermore, RPE has also been successfully produced using this process using an iPSC line produced from a donor homozygous for HLA-A*03 and HLA-B*07 called HLA Line C (21526.101) that could potentially provide a beneficial match to 7.63% of the US population. HLA Line A (21525.102) and HLA Line C (21526.101) homozygous at HLA-A and HLA-B as described above are the property of Cellular Dynamics International, Inc. In addition, the reproducibility was further confirmed in 109 RPE differentiations performed on 28 iPSC lines derived from 13 donors by measuring the percentage of Cralbp-positive cells before and after purification (FIG. 6C-D). While the percentage of Cralbp-positive cells after RPE differentiation varied, the MACS purification consistently resulted in more than 95 percent purity and in most cases near 100 percent purity. Thus, the present method of RPE differentiation has a distinct advantage over any methods that produce RPE cells from embryoid bodies as it provides more consistent and reproducible results across donor genotypes and when performed by different operators.

TABLE 2

Multi-operator RPE Differentiation

| Operator | iPSC Line | Day of Analysis | % Cralbp+ | Avg. | St Dev. |
|---|---|---|---|---|---|
| 1 | Line 1 | 40 | 81.8 | 82.9 | 9.6 |
| 2 | Line 1 | 47 | 68.0 | | |
| 3 | Line 1 | 40 | 86.2 | | |
| 4 | Line 1 | 41 | 76.7 | | |
| 5 | Line 1 | 40 | 91.6 | | |
| 6 | Line 1 | 40 | 93.3 | | |
| 1 | Line 2 | 42 | 71.8 | 74.6 | 5.5 |
| 2 | Line 2 | 46 | 72.2 | | |
| 3 | Line 2 | 40 | 79.6 | | |
| 4 | Line 2 | 40 | 68.2 | | |
| 5 | Line 2 | 40 | 81.1 | | |
| 1 | Line 3 | 42 | 72.5 | 72.3 | 7.0 |
| 2 | Line 3 | 46 | 75.3 | | |
| 3 | Line 3 | 40 | 80.5 | | |
| 4 | Line 3 | 40 | 67.2 | | |
| 5 | Line 3 | 40 | 77.1 | | |
| 6 | Line 3 | 40 | 61.3 | | |

Example 11—Materials and Methods

Materials used in Examples 1-10 are shown in Table 3.

TABLE 3

Exemplary Medium Components

| Component | Vendor | Cat# | Final Conc. |
|---|---|---|---|
| Essential 8 Medium | | | |
| Essential 8 ™ Basal Medium | Life Technologies | A1517001 | 98% |
| Essential 8 ™ Supplement | Life Technologies | | 2% |
| Essential 8 Plating Medium | | | |
| Complete Essential 8 ™ Medium | Life Technologies | As prepared above | 100% |
| Blebbistatin | Sigma | B0560 | 2.5 μM |
| Retinal Induction Medium (RIM) | | | |
| DMEM/F12 | Life Technologies | 11330-032 | 99% |
| CTS ™ KnockOut ™ SR XenoFree | Life Technologies | A1099201 | 1.5% |
| MEM non-essential AA | Life Technologies | 11140 | 0.1 mM |
| Sodium Pyruvate | Life Technologies | 11360-070 | 1 mM |
| CTS ™ N-2 Supplement | Life Technologies | A13707-01 | 1% |
| B-27 ® Supplement (+VitA) | Life Technologies | 17504-044 | 2% |
| Ascorbic Acid | Sigma | A4544 | 200 μM |
| LDN-193189 | Stemgent | 04-0074 | 10 nM |
| SB 431542 | R&D Systems | 1614/10 | 1.0 μM |
| CKI-7 Dihydrochloride | Sigma | C0742 | 0.5 μM |
| AF-IGF-1 | R&D Systems | AFL291 | 1 ng/ml |
| Retinal Differentiation Medium (RDM) | | | |
| DMEM/F12 | Life Technologies | 11330-032 | 99% |
| CTS ™ KnockOut ™ SR XenoFree | Life Technologies | A1099201 | 1.5% |
| MEM non-essential AA | Life Technologies | 11140 | 0.1 mM |
| Sodium Pyruvate | Life Technologies | 11360-070 | 1 mM |
| N-2 Supplement | Life Technologies | A13707-01 | 1% |
| B-27 ® Supplement (+VitA) | Life Technologies | 17504-044 | 2% |
| Ascorbic Acid | Sigma | A4544 | 200 μM |
| LDN-193189 | Stemgent | 04-0074 | 100 nM |
| SB 431542 | R&D Systems | 1614/10 | 10 μM |
| CKI-7 Dihydrochloride | Sigma | C0742 | 5 μM |
| AF-IGF-1 | R&D Systems | AFL291 | 10 ng/ml |
| PD0325901 | Stemgent | 04-0006 | 1 μM |
| Retinal Medium (RM) + Nicotinamide and Activin | | | |
| DMEM/F12 | Life Technologies | 11330-032 | 99% |
| CTS ™ KnockOut ™ SR XenoFree Kit | Life Technologies | A1099201 | 1.5% |
| MEM non-essential AA | Life Technologies | 11140 | 0.1 mM |
| Sodium Pyruvate | Life Technologies | 11360-070 | 1 mM |
| CTS ™ N-2 Supplement | Life Technologies | A13707-01 | 1% |
| B-27 ® Supplement (+VitA) | Life Technologies | 17504-044 | 2% |
| Ascorbic Acid | Sigma | A4544 | 200 μM |
| Nicotinamide | Sigma | N0636 | 10 mM |
| Activin A | R&D Systems | 338-AC | 100 ng/ml |
| RPE-Maturation Medium (RPE-MM) | | | |
| MEM Alpha | Life Technologies | 12571-063 | 99% |

TABLE 3-continued

Exemplary Medium Components

| Component | Vendor | Cat# | Final Conc. |
|---|---|---|---|
| Fetal Bovine Serum | Hyclone | SH30071.03 | 5% |
| CTS ™ N-2 Supplement | Life Technologies | A13707-01 | 1% |
| MEM non-essential AA | Life Technologies | 11140 | 0.1 mM |
| Sodium Pyruvate | Life Technologies | 11360-070 | 1 mM |
| Taurine | Sigma | T4571 | 250 µg/ml |
| Hydrocortisone | Sigma | H6909 | 20 µg/L |
| 3,3',5-Triiodo-L-thyronine | Sigma | T-5516 | 0.013 µg/L |
| RPE-MM + PD0325901 | | | |
| MEM Alpha | Life Technologies | 12571-063 | 99% |
| Fetal Bovine Serum | Hyclone | SH30071.03 | 5% |
| CTS ™ N-2 Supplement | Life Technologies | A13707-01 | 1% |
| MEM non-essential AA | Life Technologies | 11140 | 0.1 mM |
| Sodium Pyruvate | Life Technologies | 11360-070 | 1 mM |
| Taurine | Sigma | T4571 | 250 µg/ml |
| Hydrocortisone | Sigma | H6909 | 20 µg/L |
| 3,3',5-Triiodo-L-thyronine | Sigma | T-5516 | 0.013 µg/L |
| PD0325901 | Stemgent | 04-0006 | 1 µM |
| RPE-MM + PGE2 | | | |
| MEM Alpha | Life Technologies | 12571-063 | 99% |
| Fetal Bovine Serum | Hyclone | SH30071.03 | 5% |
| CTS ™ N-2 Supplement | Life Technologies | A13707-01 | 1% |
| MEM non-essential AA | Life Technologies | 11140 | 0.1 mM |
| Sodium Pyruvate | Life Technologies | 11360-070 | 1 mM |
| Taurine | Sigma | T4571 | 250 µg/ml |
| Hydrocortisone | Sigma | H6909 | 20 µg/L |
| 3,3',5-Triiodo-L-thyronine | Sigma | T-5516 | 0.013 µg/L |
| PGE2 | R&D Systems | 2296 | 50 µM |
| RPE-MM Plating Medium | | | |
| MEM Alpha | Life Technologies | 12571-063 | 99% |
| Fetal Bovine Serum | Hyclone | SH30071.03 | 5% |
| CTS ™ N-2 Supplement | Life Technologies | A13707-01 | 1% |
| MEM non-essential AA | Life Technologies | 11140 | 0.1 mM |
| Sodium Pyruvate | Life Technologies | 11360-070 | 1 mM |
| Taurine | Sigma | T4571 | 250 µg/ml |
| Hydrocortisone | Sigma | H6909 | 20 µg/L |
| 3,3',5-Triiodo-L-thyronine | Sigma | T-5516 | 0.013 µg/L |
| Y-27632 | R&D Systems | 1254/10 | 10 µM |
| MACS Buffer | | | |
| DPBS (without calcium and magnesium) | Life Technologies | 14190-144 | 98% |
| Fetal Bovine Serum | Hyclone | SH30071.03 | 2% |
| UltraPure ™ EDTA Solution | Life Technologies | 15575-020 | 2 mM |
| Essential 8 Medium | | | |
| Essential 8 ™ Basal Medium | Life Technologies | A1517001 | 98% |
| Essential 8 ™ Supplement | Life Technologies | | 2% |
| Essential 8 Plating Medium | | | |
| Complete Essential 8 ™ Medium | Life Technologies | As prepared above | 100% |
| Blebbistatin | Sigma | B0560 | 2.5 µM |
| Retinal Induction Medium (RIM) | | | |
| DMEM/F12 | Life Technologies | 11330-032 | 99% |
| CTS ™ KnockOut ™ SR XenoFree | Life Technologies | A1099201 | 1.5% |
| MEM non-essential AA | Life Technologies | 11140 | 0.1 mM |
| Sodium Pyruvate | Life Technologies | 11360-070 | 1 mM |
| CTS ™ N-2 Supplement | Life Technologies | A13707-01 | 1% |
| B-27 ® Supplement (+VitA) | Life Technologies | 17504-044 | 2% |
| Ascorbic Acid | Sigma | A4544 | 200 µM |
| LDN-193189 | Stemgent | 04-0074 | 10 nM |
| SB 431542 | R&D Systems | 1614/10 | 1.0 µM |
| CKI-7 Dihydrochloride | Sigma | C0742 | 0.5 µM |
| AF-IGF-1 | R&D Systems | AFL291 | 1 ng/ml |
| Retinal Differentiation Medium (RDM) | | | |
| DMEM/F12 | Life Technologies | 11330-032 | 99% |
| CTS ™ KnockOut ™ SR XenoFree | Life Technologies | A1099201 | 1.5% |
| MEM non-essential AA | Life Technologies | 11140 | 0.1 mM |
| Sodium Pyruvate | Life Technologies | 11360-070 | 1 mM |
| N-2 Supplement | Life Technologies | A13707-01 | 1% |
| B-27 ® Supplement (+VitA) | Life Technologies | 17504-044 | 2% |
| Ascorbic Acid | Sigma | A4544 | 200 µM |
| LDN-193189 | Stemgent | 04-0074 | 100 nM |
| SB 431542 | R&D Systems | 1614/10 | 10 µM |
| CKI-7 Dihydrochloride | Sigma | C0742 | 5 µM |
| AF-IGF-1 | R&D Systems | AFL291 | 10 ng/ml |
| PD0325901 | Stemgent | 04-0006 | 1 µM |
| Retinal Medium (RM) + Nicotinamide and Activin | | | |
| DMEM/F12 | Life Technologies | 11330-032 | 99% |
| CTS ™ KnockOut ™ SR XenoFree Kit | Life Technologies | A1099201 | 1.5% |
| MEM non-essential AA | Life Technologies | 11140 | 0.1 mM |
| Sodium Pyruvate | Life Technologies | 11360-070 | 1 mM |
| CTS ™ N-2 Supplement | Life Technologies | A13707-01 | 1% |
| B-27 ® Supplement (+VitA) | Life Technologies | 17504-044 | 2% |
| Ascorbic Acid | Sigma | A4544 | 200 µM |
| Nicotinamide | Sigma | N0636 | 10 mM |
| Activin A | R&D Systems | 338-AC | 100 ng/ml |
| RPE-Maturation Medium (RPE-MM) | | | |
| MEM Alpha | Life Technologies | 12571-063 | 99% |
| Fetal Bovine Serum | Hyclone | SH30071.03 | 5% |
| CTS ™ N-2 Supplement | Life Technologies | A13707-01 | 1% |
| MEM non-essential AA | Life Technologies | 11140 | 0.1 mM |
| Sodium Pyruvate | Life Technologies | 11360-070 | 1 mM |
| Taurine | Sigma | T4571 | 250 µg/ml |
| Hydrocortisone | Sigma | H6909 | 20 µg/L |
| 3,3',5-Triiodo-L-thyronine | Sigma | T-5516 | 0.013 µg/L |
| RPE-MM + PD0325901 | | | |
| MEM Alpha | Life Technologies | 12571-063 | 99% |
| Fetal Bovine Serum | Hyclone | SH30071.03 | 5% |

TABLE 3-continued

Exemplary Medium Components

| Component | Vendor | Cat# | Final Conc. |
|---|---|---|---|
| CTS ™ N-2 Supplement | Life Technologies | A13707-01 | 1% |
| MEM non-essential AA | Life Technologies | 11140 | 0.1 mM |
| Sodium Pyruvate | Life Technologies | 11360-070 | 1 mM |
| Taurine | Sigma | T4571 | 250 µg/ml |
| Hydrocortisone | Sigma | H6909 | 20 µg/L |
| 3,3',5-Triiodo-L-thyronine | Sigma | T-5516 | 0.013 µg/L |
| PD0325901 | Stemgent | 04-0006 | 1 µM |

RPE-MM + PGE2

| Component | Vendor | Cat# | Final Conc. |
|---|---|---|---|
| MEM Alpha | Life Technologies | 12571-063 | 99% |
| Fetal Bovine Serum | Hyclone | SH30071.03 | 5% |
| CTS ™ N-2 Supplement | Life Technologies | A13707-01 | 1% |
| MEM non-essential AA | Life Technologies | 11140 | 0.1 mM |
| Sodium Pyruvate | Life Technologies | 11360-070 | 1 mM |
| Taurine | Sigma | T4571 | 250 µg/ml |
| Hydrocortisone | Sigma | H6909 | 20 µg/L |
| 3,3',5-Triiodo-L-thyronine | Sigma | T-5516 | 0.013 µg/L |
| PGE2 | R&D Systems | 2296 | 50 µM |

RPE-MM Plating Medium

| Component | Vendor | Cat# | Final Conc. |
|---|---|---|---|
| MEM Alpha | Life Technologies | 12571-063 | 99% |
| Fetal Bovine Serum | Hyclone | SH30071.03 | 5% |
| CTS ™ N-2 Supplement | Life Technologies | A13707-01 | 1% |
| MEM non-essential AA | Life Technologies | 11140 | 0.1 mM |
| Sodium Pyruvate | Life Technologies | 11360-070 | 1 mM |
| Taurine | Sigma | T4571 | 250 µg/ml |
| Hydrocortisone | Sigma | H6909 | 20 µg/L |
| 3,3',5-Triiodo-L-thyronine | Sigma | T-5516 | 0.013 µg/L |
| Y-27632 | R&D Systems | 1254/10 | 10 µM |

MACS Buffer

| Component | Vendor | Cat# | Final Conc. |
|---|---|---|---|
| DPBS (without calcium and magnesium) | Life Technologies | 14190-144 | 98% |
| Fetal Bovine Serum | Hyclone | SH30071.03 | 2% |
| UltraPure ™ EDTA Solution | Life Technologies | 15575-020 | 2 mM |

Essential 8 Medium

| Component | Vendor | Cat# | Final Conc. |
|---|---|---|---|
| Essential 8 ™ Basal Medium | Life Technologies | A1517001 | 98% |
| Essential 8 ™ Supplement | Life Technologies |  | 2% |

Essential 8 Plating Medium

| Component | Vendor | Cat# | Final Conc. |
|---|---|---|---|
| Complete Essential 8 ™ Medium | Life Technologies | As prepared above | 100% |
| Blebbistatin | Sigma | B0560 | 2.5 µM |

Retinal Induction Medium (RIM)

| Component | Vendor | Cat# | Final Conc. |
|---|---|---|---|
| DMEM/F12 | Life Technologies | 11330-032 | 99% |
| CTS ™ KnockOut ™ SR XenoFree | Life Technologies | A1099201 | 1.5% |
| MEM non-essential AA | Life Technologies | 11140 | 0.1 mM |
| Sodium Pyruvate | Life Technologies | 11360-070 | 1 mM |
| CTS ™ N-2 Supplement | Life Technologies | A13707-01 | 1% |
| B-27 ® Supplement (+VitA) | Life Technologies | 17504-044 | 2% |
| Ascorbic Acid | Sigma | A4544 | 200 µM |
| LDN-193189 | Stemgent | 04-0074 | 10 nM |
| SB 431542 | R&D Systems | 1614/10 | 1.0 µM |
| CKI-7 Dihydrochloride | Sigma | C0742 | 0.5 µM |
| AF-IGF-1 | R&D Systems | AFL291 | 1 ng/ml |

Retinal Differentiation Medium (RDM)

| Component | Vendor | Cat# | Final Conc. |
|---|---|---|---|
| DMEM/F12 | Life Technologies | 11330-032 | 99% |
| CTS ™ KnockOut ™ SR XenoFree | Life Technologies | A1099201 | 1.5% |
| MEM non-essential AA | Life Technologies | 11140 | 0.1 mM |
| Sodium Pyruvate | Life Technologies | 11360-070 | 1 mM |
| N-2 Supplement | Life Technologies | A13707-01 | 1% |
| B-27 ® Supplement (+VitA) | Life Technologies | 17504-044 | 2% |
| Ascorbic Acid | Sigma | A4544 | 200 µM |
| LDN-193189 | Stemgent | 04-0074 | 100 nM |
| SB 431542 | R&D Systems | 1614/10 | 10 µM |
| CKI-7 Dihydrochloride | Sigma | C0742 | 5 µM |
| AF-IGF-1 | R&D Systems | AFL291 | 10 ng/ml |
| PD0325901 | Stemgent | 04-0006 | 1 µM |

Retinal Medium (RM) + Nicotinamide and Activin

| Component | Vendor | Cat# | Final Conc. |
|---|---|---|---|
| DMEM/F12 | Life Technologies | 11330-032 | 99% |
| CTS ™ KnockOut ™ SR XenoFree Kit | Life Technologies | A1099201 | 1.5% |
| MEM non-essential AA | Life Technologies | 11140 | 0.1 mM |
| Sodium Pyruvate | Life Technologies | 11360-070 | 1 mM |
| CTS ™ N-2 Supplement | Life Technologies | A13707-01 | 1% |
| B-27 ® Supplement (+VitA) | Life Technologies | 17504-044 | 2% |
| Ascorbic Acid | Sigma | A4544 | 200 µM |
| Nicotinamide | Sigma | N0636 | 10 mM |
| Activin A | R&D Systems | 338-AC | 100 ng/ml |

RPE-Maturation Medium (RPE-MM)

| Component | Vendor | Cat# | Final Conc. |
|---|---|---|---|
| MEM Alpha | Life Technologies | 12571-063 | 99% |
| Fetal Bovine Serum | Hyclone | SH30071.03 | 5% |
| CTS ™ N-2 Supplement | Life Technologies | A13707-01 | 1% |
| MEM non-essential AA | Life Technologies | 11140 | 0.1 mM |
| Sodium Pyruvate | Life Technologies | 11360-070 | 1 mM |
| Taurine | Sigma | T4571 | 250 µg/ml |
| Hydrocortisone | Sigma | H6909 | 20 µg/L |
| 3,3',5-Triiodo-L-thyronine | Sigma | T-5516 | 0.013 µg/L |

RPE-MM + PD0325901

| Component | Vendor | Cat# | Final Conc. |
|---|---|---|---|
| MEM Alpha | Life Technologies | 12571-063 | 99% |
| Fetal Bovine Serum | Hyclone | SH30071.03 | 5% |
| CTS ™ N-2 Supplement | Life Technologies | A13707-01 | 1% |
| MEM non-essential AA | Life Technologies | 11140 | 0.1 mM |
| Sodium Pyruvate | Life Technologies | 11360-070 | 1 mM |
| Taurine | Sigma | T4571 | 250 µg/ml |
| Hydrocortisone | Sigma | H6909 | 20 µg/L |
| 3,3',5-Triiodo-L-thyronine | Sigma | T-5516 | 0.013 µg/L |
| PD0325901 | Stemgent | 04-0006 | 1 µM |

RPE-MM + PGE2

| Component | Vendor | Cat# | Final Conc. |
|---|---|---|---|
| MEM Alpha | Life Technologies | 12571-063 | 99% |
| Fetal Bovine Serum | Hyclone | SH30071.03 | 5% |
| CTS ™ N-2 Supplement | Life Technologies | A13707-01 | 1% |

TABLE 3-continued

Exemplary Medium Components

| Component | Vendor | Cat# | Final Conc. |
|---|---|---|---|
| MEM non-essential AA | Life Technologies | 11140 | 0.1 mM |
| Sodium Pyruvate | Life Technologies | 11360-070 | 1 mM |
| Taurine | Sigma | T4571 | 250 μg/ml |
| Hydrocortisone | Sigma | H6909 | 20 μg/L |
| 3,3',5-Triiodo-L-thyronine | Sigma | T-5516 | 0.013 μg/L |
| PGE2 | R&D Systems | 2296 | 50 μM |
| RPE-MM Plating Medium | | | |
| MEM Alpha | Life Technologies | 12571-063 | 99% |
| Fetal Bovine Serum | Hyclone | SH30071.03 | 5% |
| CTS ™ N-2 Supplement | Life Technologies | A13707-01 | 1% |
| MEM non-essential AA | Life Technologies | 11140 | 0.1 mM |
| Sodium Pyruvate | Life Technologies | 11360-070 | 1 mM |
| Taurine | Sigma | T4571 | 250 μg/ml |
| Hydrocortisone | Sigma | H6909 | 20 μg/L |
| 3,3',5-Triiodo-L-thyronine | Sigma | T-5516 | 0.013 μg/L |
| Y-27632 | R&D Systems | 1254/10 | 10 μM |
| MACS Buffer | | | |
| DPBS (without calcium and magnesium) | Life Technologies | 14190-144 | 98% |
| Fetal Bovine Serum | Hyclone | SH30071.03 | 2% |
| UltraPure ™ EDTA Solution | Life Technologies | 15575-020 | 2 mM |

The flow cytometry wash buffer was prepared by adding 20 mL FBS to 1000 mL of DPBS (i.e. without calcium and magnesium). The buffer was filter sterilized and can be stored at 4° C. for up to 4 weeks.

The flow cytometry perm buffer was prepared by adding 20 mL FBS to 1000 mL DPBS (i.e. without calcium and magnesium). One gram of Saponin was added and mixed well. The buffer was filter sterilized and can be stored at 4° C. for up to 4 weeks.

The flow cytometry Live-Dead Red stain was prepared by diluting Live-Dead Stain 1:1000 in DPBS (i.e. without calcium and magnesium). One mL of the stain was prepared per $1 \times 10^6$ cells being assayed. The stain was prepared fresh before use.

The flow cytometry fixation buffer was prepared by adding 1 mL of 36.5% Formaldehyde to 8.1 mL of DPBS (i.e. without calcium and magnesium). One mL of stain was prepared per $1 \times 10^6$ cells being assayed. The buffer was prepared fresh before use.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Amit et al., Dev. Bio., 227:271-278, 2000.
Buchholz et al., Stem Cells, 27: 2427-2434, 2009.
Byrne et al., Nature, 450(7169):497-502, 2007.
Hirami et al., Neurosci. Lett., 48: 126-131, 2009.
Kanemura et al., PLoS One, 9, 2014.
Ludwig et al., Nat. Biotechnol., 24:185-187, 2006b.
Ludwig et al., Nat. Methods, 3:637-646, 2006a.
PCT Publication No. WO 2007/069666 A1.
PCT Publication No. WO 2014/121077.
Smith, In: Origins and Properties of Mouse Embryonic Stem Cells, 2000.
Strauss et al., Physiological Reviews, 85:845-881, 2005.
Takahashi et al., Cell, 126, 663-676, 2006.
Takahashi et al., Cell, 131, 861-872, 2007.
Thomson and Marshall, Curr. Top. Dev. Biol., 38:133-165, 1998.
Thomson and Odorico, Trends Biotechnol., 18(2):53-57, 2000.
Thomson et al. Proc. Natl. Acad. Scie. USA, 92:7844-7848, 1995.
U.S. Pat. No. 8,546,140.
U.S. Patent Application No. 2002/0076747.
U.S. Patent Application No. 2009/0246875.
U.S. Patent Application No. 2010/0210014.
U.S. Patent Application No. 2012/0196360.
U.S. Patent Application No. 2012/0276636.
U.S. Pat. No. 5,843,780.
U.S. Pat. No. 6,103,470.
U.S. Pat. No. 6,200,806.
U.S. Pat. No. 6,416,998.
U.S. Pat. No. 6,833,269.
U.S. Pat. No. 7,029,913.
U.S. Pat. No. 7,442,548.
U.S. Pat. No. 7,598,364.
U.S. Pat. No. 7,682,828.
U.S. Pat. No. 7,989,425.
U.S. Pat. No. 8,058,065.
U.S. Pat. No. 8,071,369.
U.S. Pat. No. 8,129,187.
U.S. Pat. No. 8,268,620.
U.S. Pat. No. 8,278,620.
U.S. Pat. No. 8,546,140.
U.S. Pat. No. 8,741,648.
U.S. Patent Publication No. 2003/0211603.
U.S. Patent Publication No. 2010/0003757.
Xu et al., Nat. Biotechnol., 19:971-974, 2001.
Ying et al., Cell, 115:281-292, 2003.
Yu et al., Science, 318: 1917-1920, 2007.

What is claimed is:

1. A method for enriching for RPE cells from a starting population of RPE cells, the method comprising depleting CD56+ cells from the starting RPE cell population to provide the RPE-enriched cell population, wherein at least 90% of the cells in the RPE-enriched cell population are PMEL17+ and at least 90% of the cells in the RPE-enriched population are TYRP1+.

2. The method of claim 1, wherein at least 95% of the cells in the RPE-enriched cell population are PMEL17+ and at least 95% of the cells in the RPE-enriched population are TYRP1+.

3. The method of claim 1, wherein the starting cell population is prepared from pluripotent stem cells.

4. The method of claim 3, wherein the pluripotent stem cells are induced pluripotent stem cells.

5. The method of claim 1, wherein CD56+ cells are depleted by magnetic bead-based sorting or fluorescence-based sorting.

6. The method of claim 1, wherein CD56+ cells are depleted using an antibody or an aptamer.

7. The method of claim 1, wherein the RPE-enriched cell population is not genetically modified.

8. The method of claim 1, wherein the method is carried out without genetically engineering the starting cell population.

9. The method of claim 1, wherein the method comprises enriching said starting cell population for RPE-enriched cells by further depleting therefrom CD24+ cells.

10. The method of claim 1, wherein the method comprises enriching said starting cell population for RPE cells by further depleting therefrom CD90+ cells.

11. The method of claim 1, wherein the method comprises enriching said starting cell population for RPE cells by depleting therefrom CD24+ cells, CD56+ cells and CD90+ cells.

12. The method of claim 1, wherein the human RPEs are prepared from embryonic stem cells.

13. The method of claim 1, wherein the human RPEs comprise an exogenous nucleic acid.

14. The method of claim 1, wherein the human RPEs comprise an exogenous gene.

15. The method of claim 1, wherein the RPE-enriched population is at least 95% RPE cells.

16. The method of claim 1, wherein the RPE-enriched population is at least 99% RPE cells.

17. The method of claim 1, wherein the RPE-enriched population is essentially pure RPE cells.

18. The method of claim 1, wherein the RPE-enriched cell population is not genetically modified.

19. The method of claim 1, wherein the RPE-enriched cell population does not comprise exogenous nucleic acid.

* * * * *